United States Patent
Butora

(10) Patent No.: US 9,624,249 B2
(45) Date of Patent: Apr. 18, 2017

(54) NUCLEOSIDE KINASE BYPASS COMPOSITIONS AND METHODS

(71) Applicant: Merck Sharp & Dohme Corp., Rahway, NJ (US)

(72) Inventor: Gabor Butora, Martinsville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/648,726

(22) PCT Filed: Dec. 2, 2013

(86) PCT No.: PCT/US2013/072540
§ 371 (c)(1),
(2) Date: Jun. 1, 2015

(87) PCT Pub. No.: WO2014/088923
PCT Pub. Date: Jun. 12, 2014

(65) Prior Publication Data
US 2015/0315221 A1 Nov. 5, 2015

Related U.S. Application Data

(60) Provisional application No. 61/787,377, filed on Mar. 15, 2013, provisional application No. 61/734,049, filed on Dec. 6, 2013.

(51) Int. Cl.
C07D 339/08 (2006.01)
C07D 407/04 (2006.01)
(Continued)

(52) U.S. Cl.
CPC ...... *C07F 9/655363* (2013.01); *C07D 339/08* (2013.01); *C07D 407/04* (2013.01);
(Continued)

(58) Field of Classification Search
CPC .. C07D 339/08; C07D 407/04; C07D 409/12; C07D 409/14; C07D 487/04;
(Continued)

(56) References Cited

U.S. PATENT DOCUMENTS 7,601,848 B2 10/2009 Hartwich et al.
2007/0099211 A1 5/2007 Aivazachvili et al.

FOREIGN PATENT DOCUMENTS

EP WO 2008/141799 * 11/2008
WO WO9801440 A2 1/1998
(Continued)

OTHER PUBLICATIONS

Stomach cancer—Mayoclinic.com—Apr. 9, 2011.*
(Continued)

*Primary Examiner* — Valerie Rodriguez-Garcia
(74) *Attorney, Agent, or Firm* — Yong Zhao; John C. Todaro

(57) ABSTRACT

The present invention relates to disulfide masked prodrug compounds of Formula (I), nucleoside kinase bypass compositions thereof and methods that are amenable to bioactivation by a reducing agent such as glutathione:

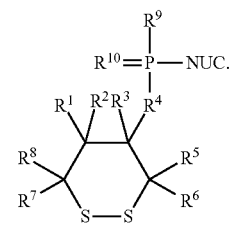

(Continued)

- Non-enzymatic, chemically driven release
- Trigger mechanism:
    1) pH – dependent disulfide reduction *followed by*
    2) charge-dissipation driven cyclodeesterification *followed by*
    3) intramolecular thiirane rearrangement Such disulfide based compounds, compositions, and methods can be useful, for example, in providing prodrugs for use as therapeutics.

16 Claims, 2 Drawing Sheets

(51) Int. Cl.
| | | |
|---|---|---|
| *C07D 409/12* | (2006.01) | |
| *C07D 409/14* | (2006.01) | |
| *C07D 487/04* | (2006.01) | |
| *C07F 9/6561* | (2006.01) | |
| *C07F 9/6553* | (2006.01) | |
| *C07F 9/6558* | (2006.01) | |
| *C07F 9/6571* | (2006.01) | |
| *C07F 9/6574* | (2006.01) | |

(52) U.S. Cl.
CPC ......... *C07D 409/12* (2013.01); *C07D 409/14* (2013.01); *C07D 487/04* (2013.01); *C07F 9/6561* (2013.01); *C07F 9/65586* (2013.01); *C07F 9/65616* (2013.01); *C07F 9/65744* (2013.01); *C07F 9/657127* (2013.01); *C07F 9/657154* (2013.01)

(58) Field of Classification Search
CPC ............ C07F 9/655363; C07F 9/65586; C07F 9/6561; C07F 9/65616; C07F 9/657127; C07F 9/657154; C07F 9/65744
See application file for complete search history.

(56) References Cited

FOREIGN PATENT DOCUMENTS

| WO | WO2008141289 A1 | 11/2008 |
|---|---|---|
| WO | WO2008141799 A8 | 11/2009 |

OTHER PUBLICATIONS

GastricMALTLymphoma—LymphomaAssociation—2011.*
"Adult Brain Tumors Treatment", National Cancer Institute, pp. 1-21 (Jan. 24, 2013) and "Types of Brain Cancer" at http://www.cancercenter.com/brain-cancer/types-of-brain-cancer.cfm (Mar. 12, 2013).*
"Colorectal Cancer" at cancer.net (published Sep. 2012), pp. 1-2.*
"Types of Breast Cancer", published in breastcancer.org (Sep. 30, 2012); p. 1.*
Schafer et al. Drug discovery Today 2008, 13 (21/22), 913-916.*
Luo et al. (Cell 136, Mar. 6, 2009; 823-837).*
Wolff (Medicinal Chemistry) summarizes the state of the prodrug art (Wolff, Manfred E. "Burger's Medicinal Chemistry, 5ed, Part I", John Wiley & Sons, 1995, pp. 975-977).*
Banker et al, "Modern Pharmaceutics, 3ed.", Marcel Dekker, New York, 1996, pp. 451 and 596.*
Jordan, V. C. Nature Reviews: Drug Discovery, 2, 2003, pp. 205-213.*

* cited by examiner

NUCLEOSIDE KINASE BYPASS COMPOSITIONS AND METHODS

CROSS REFERENCE TO RELATED APPLICATIONS

This application is a U.S. National Phase application under 35 U.S.C. §371 of PCT Application No. PCT/US2013/072540 filed Dec. 2, 2013, which claims priority from U.S. Provisional Application Ser. No. 61/787,377, filed Mar. 15, 2013 and U.S. Provisional Application Ser. No. 61/734,049, filed Dec. 6, 2012.

FIELD OF THE INVENTION

The present invention relates to disulfide masked prodrug compounds, compositions and methods that are amenable to bioactivation by a reducing agent such as glutathione. Such disulfide based compounds, compositions, and methods can be useful, for example, in providing novel prodrugs for use as therapeutics.

BACKGROUND OF THE INVENTION

The following is a discussion of relevant art pertaining to certain prodrug compositions. The discussion is provided only for understanding of the invention that follows. The summary is not an admission that any of the work described below is prior art to the claimed invention.

The fields of medicinal chemistry and biotechnology have yielded a multitude of biologically active compounds having well demonstrated in vitro activity. These compounds, however, need to be effectively delivered to target cells and tissues of interest in order to be useful as research tools or as therapeutic agents in vivo. Many biologically active molecules have in vivo activity profiles that are compromised by virtue of their net negative (anionic) charge, their size, or a combination of both anionic charge and size. Various strategies have been developed in an attempt to overcome these barriers. In the case of oligonucleotide delivery, both viral and non-viral delivery strategies have yielded mixed results, with most having dose limiting toxicity or other safety issues. Such safety issues are representative of the challenge faced in effectively delivering other charged molecules to cells and tissues of interest. These challenges have driven innovation in a divergent approach, that of the prodrug.

A prodrug is a pharmacological substance administered in an inactive or significantly less active form. Once administered, the prodrug is metabolised in vivo into an active metabolite in a process termed bioactivation. The rationale behind the use of a prodrug is generally for absorption, distribution, metabolism, and excretion (ADME) optimization. Anion masking produgs represent a new platform of compounds that provide the advantage of improving ADME properties through a variety of mechanisms. First, the anion masking prodrug neutralizes anionic charge, and therefore overcomes barriers of cellular adsorption and tissue distribution. Second, because certain nucleases rely upon anionic charge to identify their substrates, the anion masking prodrug can circumvent metabolism. Furthermore, the charge masking moiety of the prodrug can also serve as a scaffold for various chemical entities that can confer improved targeting, immunosuppression, or solubility profiles. All of these factors can lead to improved pharmacokinetic and pharmacodynamic properties of a compound or molecule of interest.

Examples of anion masking phosphotriester protecting groups have been disclosed, see for example Lebleu et al., (2000), Russ. J. Bioorg. Chem., 26, 174-182. However, this approach utilizes ultraviolet radiation for deprotection and thus is not amenable to use in vivo. Beaucage et al. (2007), J. Org. Chem., 72, 805-815 describes in vivo bioactivation of certain phosphotriester oligonucleotide prodrugs. However, this approach generates THF as a byproduct upon bioconversion. WO 2010/039543 describes certain anion masking disulfide phosphotriester oligonucleotide prodrugs. Nevertheless, cyclodeesterification of these disulfide prodrugs results in the release of a reactive thiirane species, which can limit the use of such prodrugs due to dose limiting toxicity.

Glutathione (GSH) is a tripeptide that contains an unusual peptide linkage between the amine group of cysteine, which is attached by normal peptide linkage, to a glycine and the carboxyl group of the glutamate side-chain. Glutathione is an important antioxidant, preventing damage to cellular components caused by reactive oxygen species such as free radicals and peroxides. Glutathione thiol groups are reducing agents, existing at a concentration of approximately 5 mM in cells. Glutathione reduces disulfide bonds formed within cytoplasmic proteins to cysteines by serving as an electron donor. In the process, glutathione is converted to its oxidized form glutathione disulfide (GSSG), which is also called L(−)-Glutathione. Once oxidized, glutathione can be reduced back by glutathione reductase, using NADPH as an electron donor. Glutathione is therefore an attractive bioconversion reducing agent for prodrugs.

Certain examples of glutathione activated prodrugs are disclosed in, for example, Gunnarsdottir et al., (2003), Drug Metabolism and Disposition, 32, 321-327 and Tirouvanziam et al., (2006), PNAS, 103, 12, 4628-4633. These glutathione activated prodrugs, however, do not offer any anionic charge masking capabilities. Accordingly, there exists a need for improved anion masking prodrugs that are amenable to bioconversion in vivo.

SUMMARY OF THE INVENTION

The invention provides a solution to the problem of providing glutathione activated prodrug compositions and methods that are capable of masking anionic charge and that do not result in the formation of a reactive species upon bioconversion.

Disclosed herein are prodrug compounds and compositions and methods of making and using the same. The prodrug compounds, compositions and methods of the invention feature a conformationally restricted disulfide phosphotriester moiety to mask anionic charge. The conformationally restricted disulfide phosphotriester moiety can also serve as a scaffold to attach a helper molecule, such as targeting moieties, immunosuppression moieties, solubility enhancing moieties etc. The conformationally restricted disulfide phosphotriester moiety undergoes charge dissipation driven cyclodeesterification via glutathione mediated reduction/bioconversion to release the active anionic molecule of interest and eject any helper moiety during the bioconversion process. During bioconversion, the reactive thiirane species is internally quenched via a intramolecular 1,5-exo-tet ring closure to produce stable tetrahydrothiophenes. The disulfide phosphotriester moiety of the invention can provide charge masked prodrug analogs of nucleic acids, polynucleotides, oligonucleotides, peptides, polypeptides, proteins, antibodies, hormones, small molecules, antivirals and other biologically active molecules as are known in the art.

DETAILED DESCRIPTION OF THE INVENTION

Terms and Definitions

Figure 1:
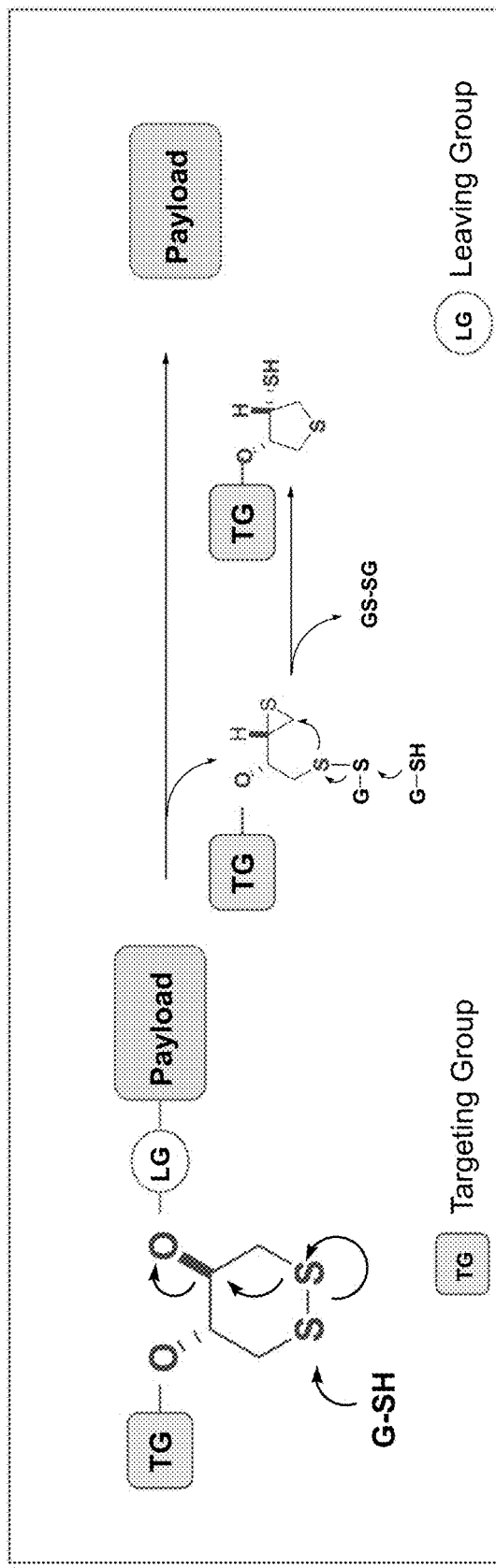
FIG. 1 shows a non-limiting example of a proposed mechanism comprising non-enzymatic, chemically driven release for disulfide masked prodrugs of the invention. While not wishing to be bound by theory, this mechanism comprises (1) pH-dependent disulfide reduction followed by (2) charge-dissipation driven cyclodeesterification followed by (3) intramolecular thiirane rearrangement. The Targeting Group (TG) can be any targeting group or moiety (e.g., a ligand, peptide, antibody, etc.) as is generally known in the art and is optionally present. The leaving group is preferably a pentavalent phosphorus leaving group as is generally known in the art, but can include other suitable leaving groups as are readily appreciated by one of skill in the art (e.g., triflates, fluorosulphonates, tosylates, mesylates, carbonylates, nitrates, phosphates, etc.). The payload is a compound that is preferably to be administered to a subject, such as any therapeutic or prophylactic compound as is generally known in the art including nucleic acids, nucleotides, nucleosides, polynucleotides, oligonucleotides, peptides, polypeptides, proteins, antibodies, hormones, small molecules, antivirals and other biologically active molecules.

The following terminology and definitions apply as used in the present application.

As used in this specification and the appended claims, the singular forms "a," "an," and "the" include plural referents unless the content clearly dictates otherwise. Thus, for example, reference to "a cell" includes a combination of two or more cells, and the like.

Any concentration range, percentage range, ratio range or integer range is to be understood to include the value of any integer within the recited range, and when appropriate, fractions thereof (such as one tenth and one hundredth of an integer), unless otherwise indicated.

"About" or "approximately," as used herein, in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

The term "alkyl" as used herein refers to its meaning as is generally accepted in the art. The term generally refers to a saturated or unsaturated hydrocarbon, including straight-chain, branched-chain, alkenyl, alkynyl groups and cyclic groups, but excludes aromatic groups. Notwithstanding the foregoing, alkyl also refers to non-aromatic heterocyclic groups. Preferably, the alkyl group has 1 to 12 carbons. More preferably, it is a lower alkyl of from 1 to 4 carbons, more preferably 1 to 4 carbons. The alkyl group can be substituted or unsubstituted. When substituted, the substituted group(s) is preferably, hydroxyl, halogen, cyano, C1-C4 alkoxy, $=$O, $=$S, $NO_2$, SH, $NH_2$, or $NR_1R_2$, where $R_1$ and $R_2$ independently are H or C1-C4 alkyl.

The term "aryl" as used herein refers to its meaning as is generally accepted in the art. The term generally refers to an aromatic group that has at least one ring having a conjugated pi electron system and includes carbocyclic aryl, heterocyclic aryl and biaryl groups, all of which can be optionally substituted. The preferred substituent(s) of aryl groups are halogen, trihalomethyl, hydroxyl, SH, OH, cyano, C1-C4 alkoxy, C1-C4 alkyl, C2-C4 alkenyl, C2-C4 alkynyl, $NH_2$, and $NR_1R_2$ groups, where $R_1$ and $R_2$ independently are H or C1-C4 alkyl.

The term "alkylaryl" as used herein refers to its meaning as is generally accepted in the art. The term generally refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and examples of heterocyclic aryl groups having such heteroatoms include furanyl, thienyl, pyridyl, pyrrolyl, N-lower alkyl pyrrolo, pyrimidyl, pyrazinyl, imidazolyl and the like, all optionally substituted. Preferably, the alkyl group is a C1-C4 alkyl group.

The term "amide" as used herein refers to its meaning as is generally accepted in the art. The term generally refers to an —C(O)—NH—R, where R is either alkyl, aryl, alkylaryl or hydrogen.

The phrase "biological system" as used herein refers to its meaning as is generally accepted in the art. The term generally refers to material, in a purified or unpurified form, from biological sources including, but not limited to, human or animal, wherein the system comprises the components required for RNAi activity. Thus, the phrase includes, for example, a cell, tissue, subject, or organism, or extract thereof. The term also includes reconstituted material from a biological source.

The term "cell" as used herein refers to its meaning as is generally accepted in the art. With reference to exemplary nucleic acid molecules of the invention, the term is used in its usual biological sense, and does not refer to an entire multicellular organism, e.g., specifically does not refer to a human being. The cell can be present in an organism, e.g., birds, plants and mammals, such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The terms "composition" or "formulation" as used herein refer to their generally accepted meaning in the art. These terms generally refer to a composition or formulation, such as in a pharmaceutically acceptable carrier or diluent, in a form suitable for administration, e.g., systemic or local administration, into a cell or subject, including, for example, a human. Suitable forms, in part, depend upon the use or the route of entry, for example oral, transdermal, inhalation, or by injection. Such forms should not prevent the composition or formulation from reaching a target cell. For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use.

The term "folate moiety" as used herein refers to its meaning as is generally accepted in the art. The term generally refers to a moiety comprising the following chemical group:

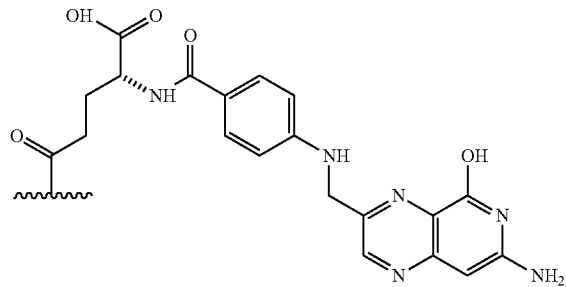 [SMILES: *C(=O)CC[C@@H](NC(=O)c1ccc(NCc2cnc3cc(N)nc(O)c3n2)cc1)C(=O)O]

The term "including" (and any form thereof, such as "includes" and "include"), "comprising" (and any form thereof, such as "has" or "have") or "containing" (and any form thereof such as "contains" or "contain") are inclusive and open-ended and do not exclude additional, unrecited elements or method steps.

The term "ligand" refers to such compounds and compositions as are generally known in the art. Non-limiting examples of such ligands are described herein including in the documents specifically incorporated by reference herein. Non-limiting, examples of such ligands are described in U.S. Publication Nos. US2008/0152661 A1 and US 2004/0162260 A1 (e.g., CDM-LBA, CDM-Pip-LBA, CDM-PEG, CDM-NAG, etc.) and U.S. patent application Ser. Nos. 10/427,160 10/201,394, 61/322,422, 61/378,609, and 61/315,223; and U.S. Pat. Nos. 6,528,631; 6,335,434; 6,235,886; 6,153,737; 5,214,136; and 5,138,045. See also Manoharan, ANTISENSE & NUCLEIC ACID DRUG DEVELOPMENT 12:103-128 (2002). A prodrug molecule of the invention can be formulated or administered with any covalently linked ligand as described herein or otherwise known in the art.

The term "linker" as used herein refers to its meaning as is generally known in the art. Non-limiting examples of linkers are described herein, for example in Table 1 and including in the documents specifically incorporated by reference herein.

TABLE 1

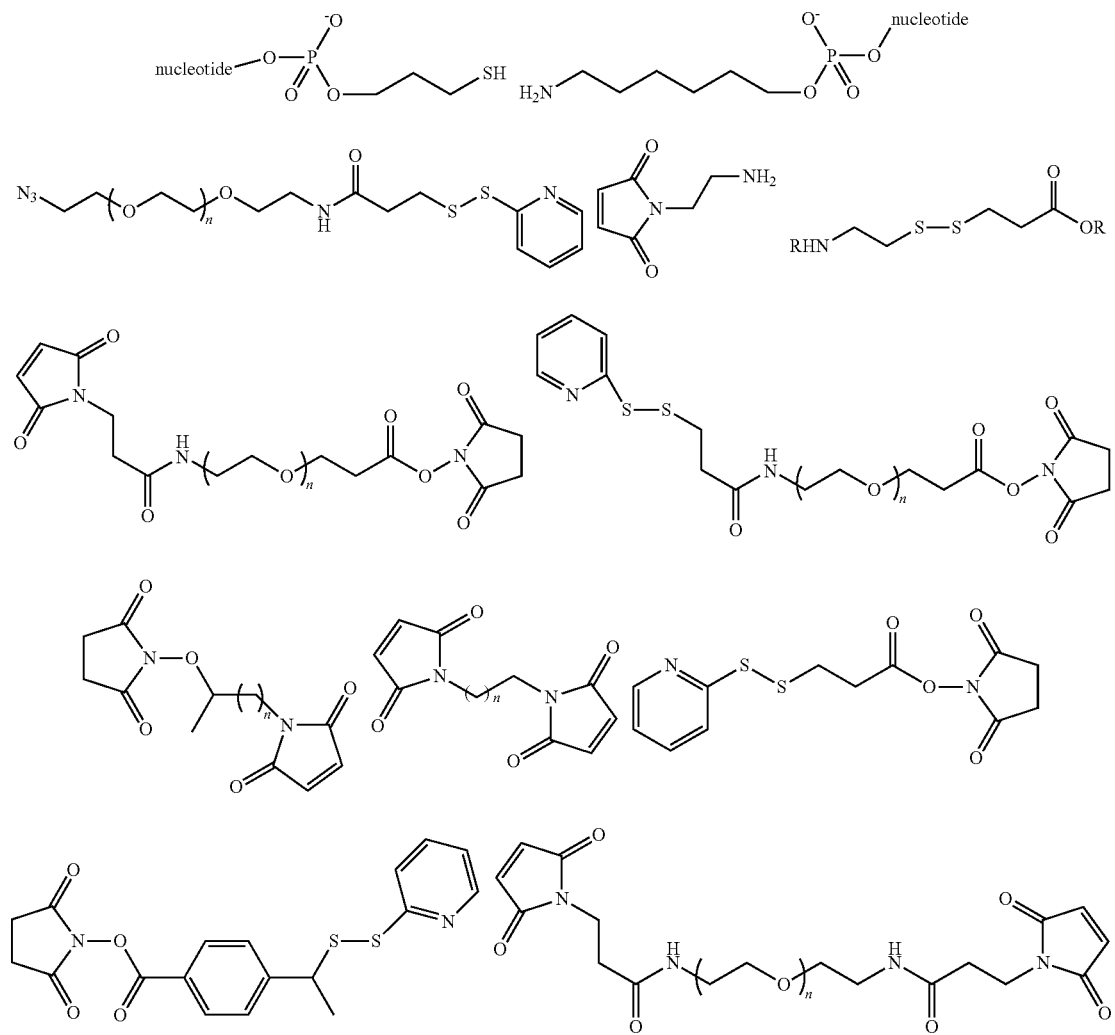

TABLE 1-continued

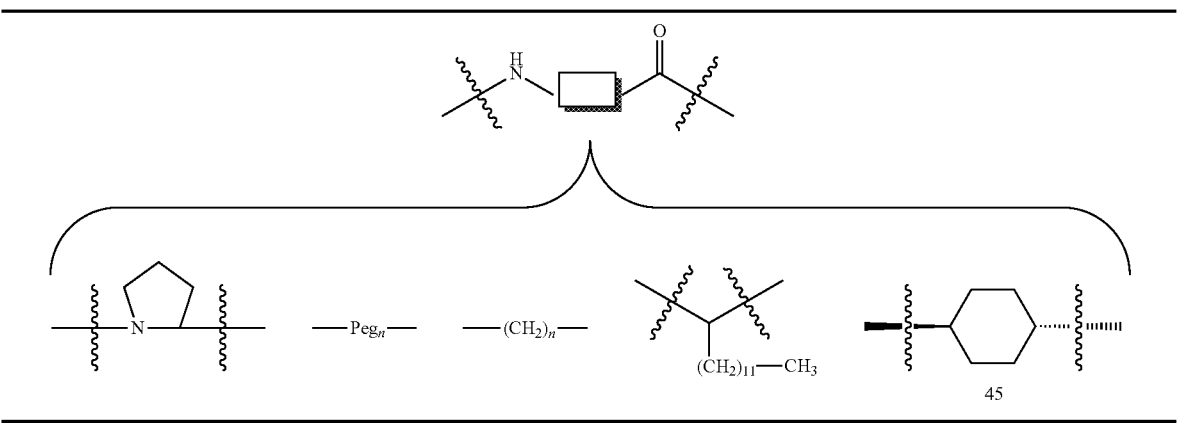

R = H, Boc, Cbz, Ac, PEG, lipid, targeting ligand, linker(s) and/or peptide(s).
"nucleotide" can be substituted with non-nucleotide moiety such as abasic or linkers as are generally known in the art.
n = 0 to 750.

The terms "mammalian" or "mammal" as used herein refers to its meaning as is generally accepted in the art. The term generally refers to any warm blooded vertebrate species, such as a human, mouse, rat, dog, cat, hamster, guinea pig, rabbit, livestock, and the like.

The term "N-Acetyl Galactosamine moiety" as used herein refers to its meaning as is generally accepted in the art. The term generally refers to a moiety comprising the following chemical group:

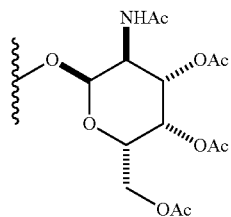 [SMILES: *O[C@@H]1O[C@@H](COC(C)=O)[C@@H](OC(C)=O)[C@@H](OC(C)=O)[C@@H]1NC(C)=O]

The term "nucleoside" as used herein refers to its meaning as is generally accepted in the art and includes nucleoside analogs, or nucleobase analogs thereof as are generally known to those of skill in the art. Non-limiting examples of nucleoside based therapeutic compounds (and corresponding indications) that may be amenable to pro-drug applications of the instant invention include that described in Table 2 below, see for example Errasti-Murugarren and Pastor-Anglada (2010), *Pharmacogenomics*, 11(6), 809-841.

TABLE 2

| | |
|---|---|
| 5-Fluoro-5'-deoxyuridine | Solid tumors including colon, breast and gastric carcinomas |
| 5-Fluoro-2'-deoxyuridine | Solid tumors including colon, breast and gastric carcinomas |
| 5-Fluorouracil | Solid tumors including gastric carcinomas, non-small-cell lung cancer and colorectal carcinomas |
| Cytarabine | Colon carcinomas, acute myeloid leukemia and non-Hodgkin's lymphoma |
| Gemcitabine | Solid tumors, including pancreatic, bladder, breast, ovarian, head, neck and non-small-cell lung cancer, hematologic malignancies, leukemia and relapsed non-Hodgkin's lymphoma |
| 5-Azacytidine | Myelodysplastic syndromes |
| 5-Aza-2'-deoxycytidine | Myelodysplastic syndromes |

TABLE 2-continued

| | |
|---|---|
| Zebularine | Under clinical trials |
| Fludarabine | Chronic lymphocytic leukemia, low grade B- and T-cell non-Hodgkin's lymphomas, Waldenström macroglobulinemia and cutaneous T-cell lymphoma |
| Cladribine | Hairy cell leukemia, chronic lymphocytic leukemia, low-grade B- and T-cell non-Hodgkin's lymphomas, Waldenström macroglobulinemia, cutaneous T-cell lymphoma and hormone-refractory prostate cancer |
| Forodesine (immucillin H) | Active in experimental tumors in mice. Under clinical trials for the treatment of B- and T-cell non-Hodgkin's lymphomas |
| Clofarabine | Acute myeloblastic leukemia, acute lymphoblastic leukemia, blast crisis of chronic myelogenous leukemia and myelodysplastic syndrome |
| AraG | Selectively toxic to mature T cells and immature T lymphoblasts |
| Mizoribine (bredinin) | Immunosuppressive agent in human renal transplantation and hepatitis C virus infections |
| 6-Mercaptopurine 6-Thioguanine Azathioprine | Pediatric acute lymphocytic leukemias, acute lymphocytic and nonlymphocytic leukemias in adults, childhood acute myeloid leukemia and non-Hodgkin's lymphoma, Crohn's disease, ulcerative colitis, solid organ transplantation, autoimmune hepatitis, rheumatoid arthritis, systemic lupus erythematosus, psoriasis, childhood severe atopic eczema and inflammatory bowel disease |
| Zidovudine | HIV infections |
| Zalcitabine | HIV infections |
| Didanosine | HIV infections |
| Stavudine | HIV infections |
| Lamivudine | Hepatitis B virus and HIV infections |
| Ribavirin | Broad spectrum of viral infections |
| Acyclovir | Cytomegalovirus infection |
| Valacyclovir | Herpes simplex and cytomegalovirus infections |
| Ganciclovir | Cytomegalovirus infection |
| Adefovir | Hepatitis B virus and HIV infections |
| Cidofovir | Herpes viruses and pox viruses infections |
| Entecavir | Hepatitis B virus and HIV infections |
| Tenofovir | Hepatitis B virus and HIV infections |
| Abacavir | HIV infections |
| Clevudine | Hepatitis B virus and Epstein-Barr virus infections |
| Emtricitabine | Hepatitis B virus and HIV infections |
| GS-9148 | HIV infections |
| R1479 | Hepatitis C virus infections |

The term "peptide moiety" as used herein refers to its meaning as is generally accepted in the art. The term generally refers to a moiety having one or more peptide functionalities.

The term "polymer" refers to polymeric compounds, compositions and formulations as are generally known in the art. Non-limiting examples of such polymers, including polymeric delivery systems are described herein including in the documents specifically incorporated by reference herein. A molecule or compound of the invention can be formulated or administered with any polymer as described herein or otherwise known in the art.

The term "steroid moiety" as used herein refers to its meaning as is generally accepted in the art. The term generally refers to a moiety having one or more steroid functionalities, such as cholesterol.

The term "subject" as used herein refers to its meaning as is generally accepted in the art. The term generally refers an organism to which the nucleic acid molecules of the invention can be administered. A subject can be a mammal or mammalian cells, including a human or human cells. The term also refers to an organism, which is a donor or recipient of explanted cells or the cells themselves.

The phrase "systemic administration" as used herein refers to its meaning as is generally accepted in the art. The phrase generally refers in vivo systemic absorption or accumulation of drugs in the blood stream followed by distribution throughout the entire body.

The term "targeting agent" as used herein refers to its meaning as is generally accepted in the art. The term generally refers to a moiety that confers some degree of target specificity to one or more cells, tissues, or organs, such as in a subject or organism and thus the ability to target such cells, tissues, or organs with a compound or composition of interest.

The phrase "therapeutically effective amount" as used herein refers to its meaning as is generally accepted in the art. The term generally refers to the amount of the compound or composition that will elicit the biological or medical response of a cell, tissue, system, animal or human that is be sought by the researcher, veterinarian, medical doctor or other clinician. For example, if a given clinical treatment is considered effective when there is at least a 25% reduction in a measurable parameter associated with a disease or disorder, a therapeutically effective amount of a drug for the treatment of that disease or disorder is that amount necessary to effect at least a 25% reduction in that parameter.

The term "vitamin moiety" as used herein refers to its meaning as is generally accepted in the art. The term generally refers to a moiety having one or more vitamin functionalities, such as folic acid, vitamin C, vitamin E, vitamin D, vitamin B5, vitamin B12 and the like.

B. Compounds

Provided herein are compounds having Formula I:

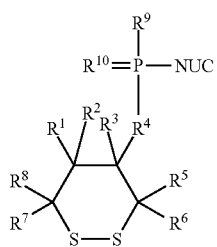

(Formula I)

wherein, $R^1$ is H, OH, $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —$NHC_{1-6}$ alkyl, $arylC_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl, or X-L-Y;

wherein X is O, S, NH, C(O), S(O), $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —$NHC_{1-6}$ alkyl, $arylC_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl;

L is a linker that is optionally present; and

Y is a targeting agent, ligand and/or polymer that is optionally present;

$R^4$ is S or O;

each $R^2$, $R^3$, $R^5$, $R^6$, $R^7$ and $R^8$ is independently halo or $R^1$ as above;

$R^9$ is O-aryl, O-phenyl, O-naphthyl, O-alkyl-aryl, or O-benzyl any of which can be substituted with one or more halo groups; or an amine, substituted amine, NH-benzyl, $NHR^{12}$ or $N(R^{12})_2$, wherein each $R^{12}$ is independently H, $C_{1-10}$ alkyl, or $C_{1-10}$ alkyl substituted with one or more halo groups;

$R^{10}$ is S or O; and

NUC is a nucleoside, nucleoside analog, nucleotide, nucleotide analog, or nucleobase analog thereof.

In certain embodiments, with reference to a compound having Formula I, $R^9$ is:

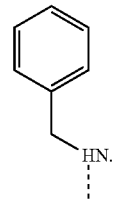

In certain embodiments, with reference to a compound having Formula I, $R^9$ is:

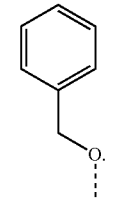

In certain embodiments, with reference to a compound having Formula I, $R^9$ is:

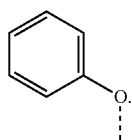

In certain embodiments, with reference to a compound having Formula I, $R^9$ is:

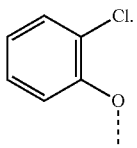

In certain embodiments, with reference to a compound having Formula I, $R^9$ is:

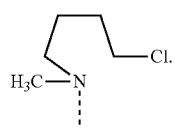

In certain embodiments, a compound having Formula I is:

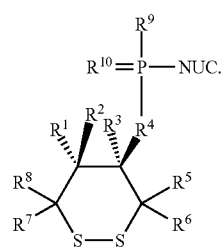

In certain embodiments, a compound having Formula I is:

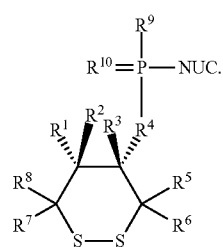

In certain embodiments, a compound having Formula I is:

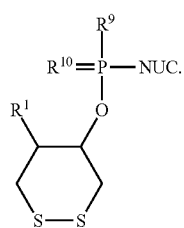

In certain embodiments, a compound having Formula I is:

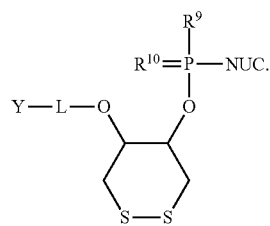

wherein L is a linker that is optionally present; and Y is a ligand and/or polymer.

In certain embodiments, a compound having Formula I is:

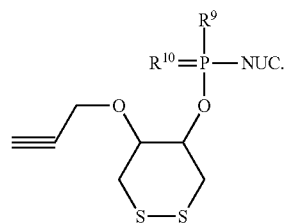

In certain embodiments, with reference to a compound having Formula I, NUC is:

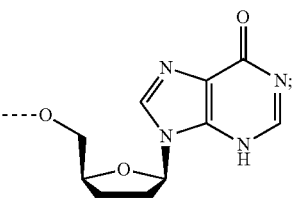

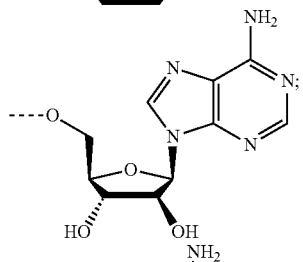

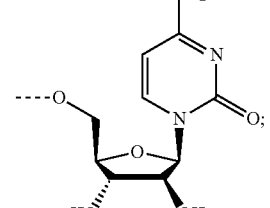

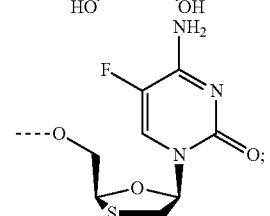

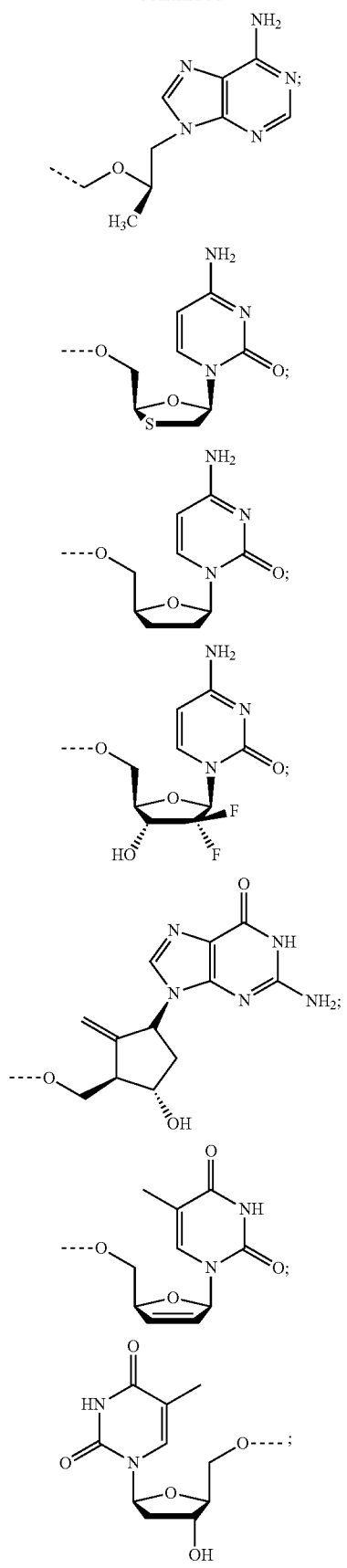
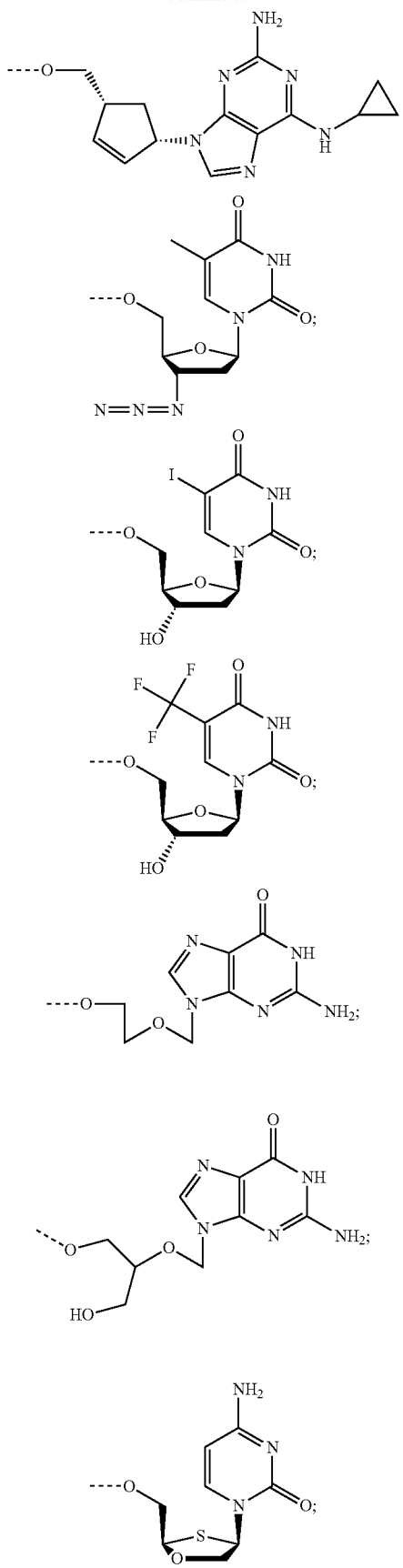

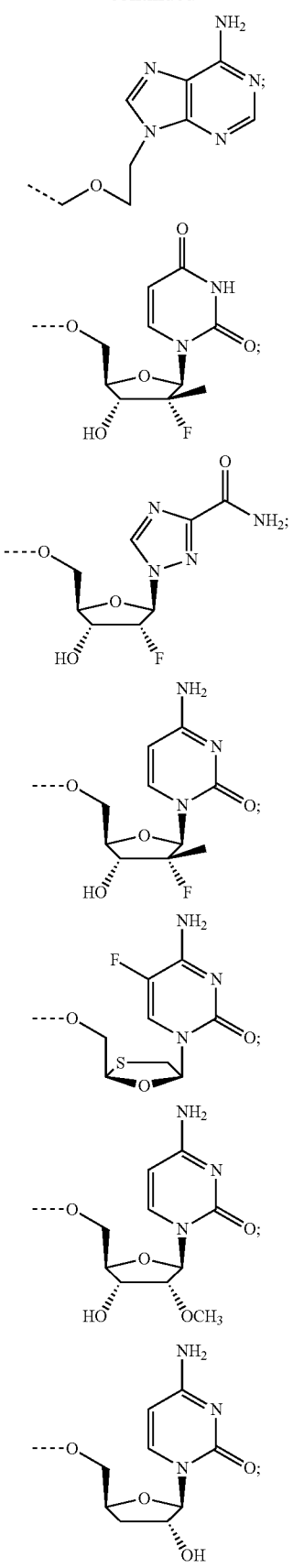
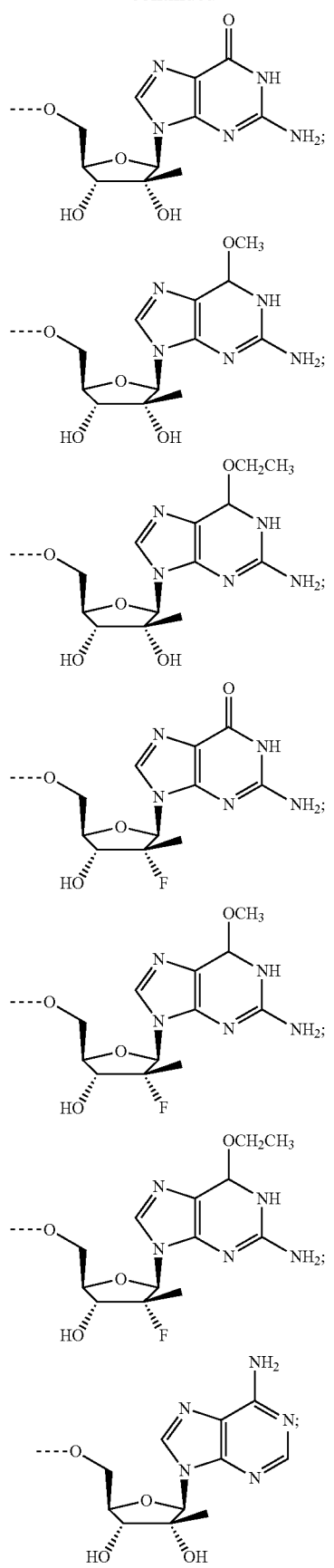

-continued
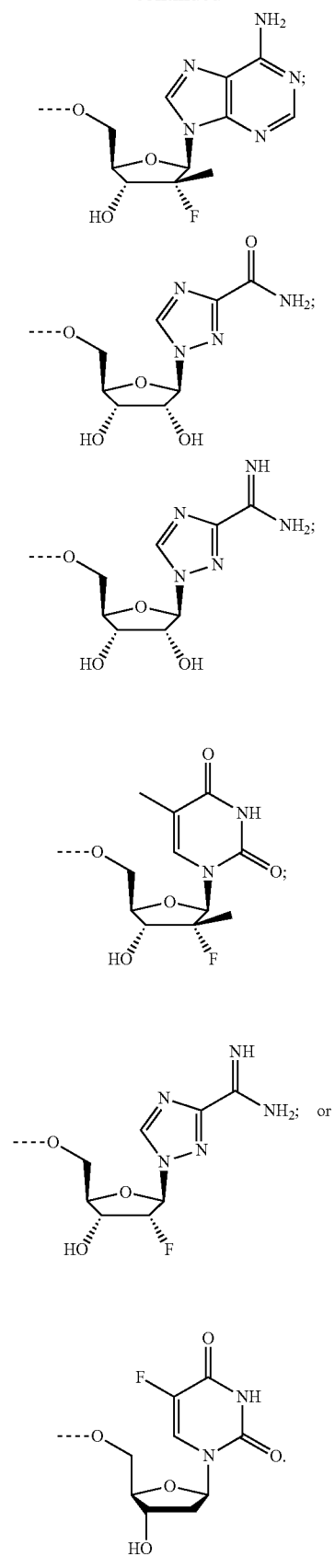
In certain embodiments, a compound having Formula I is:
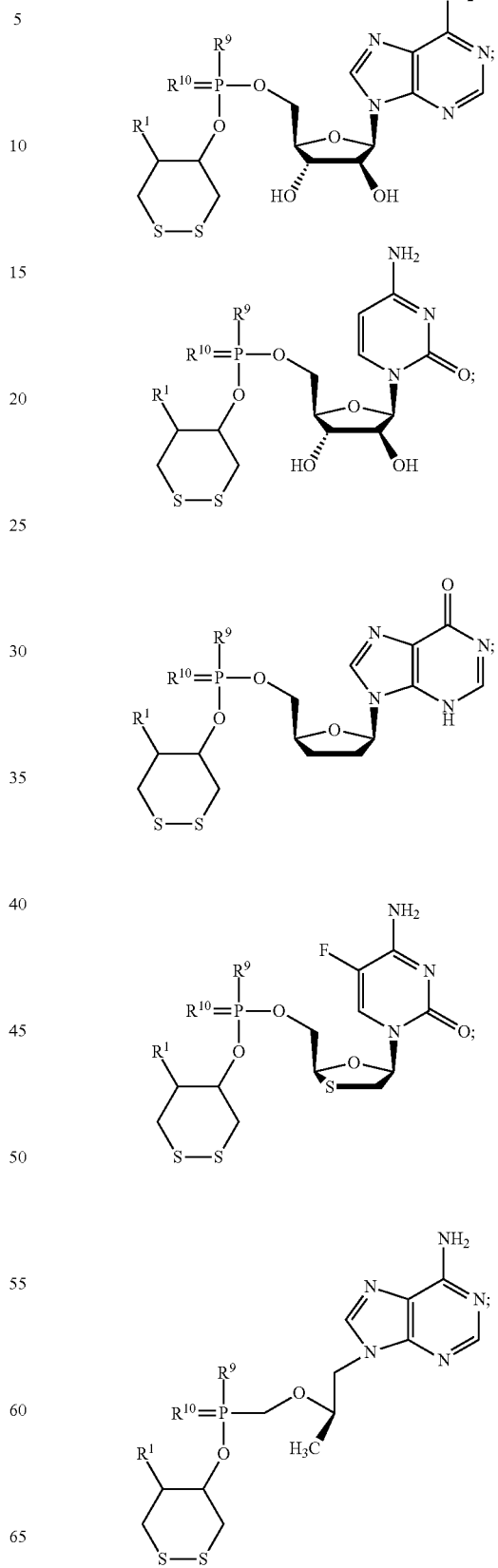

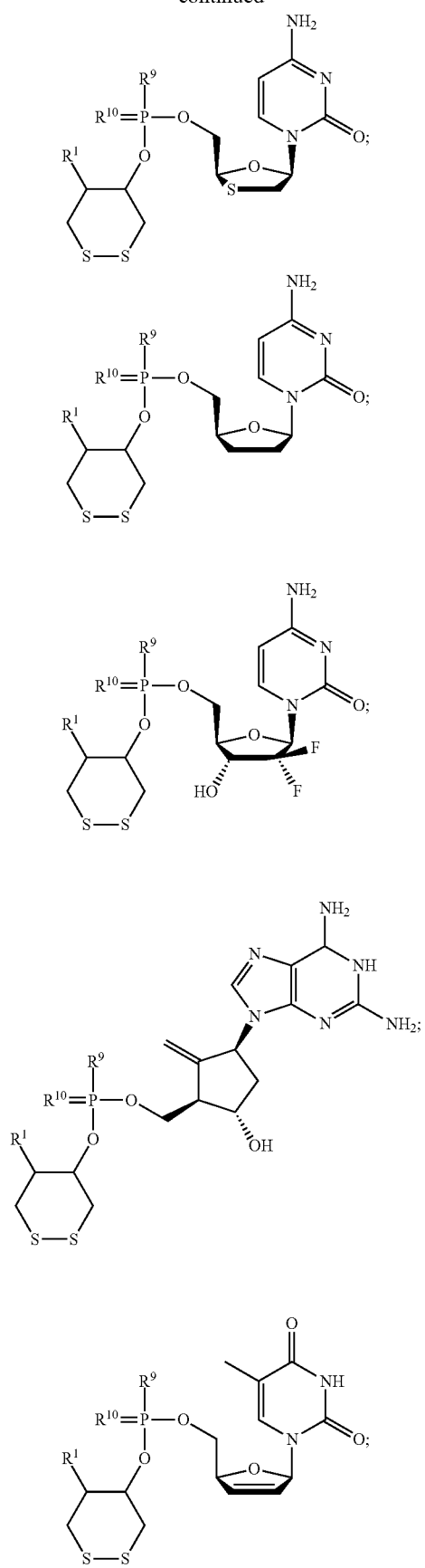
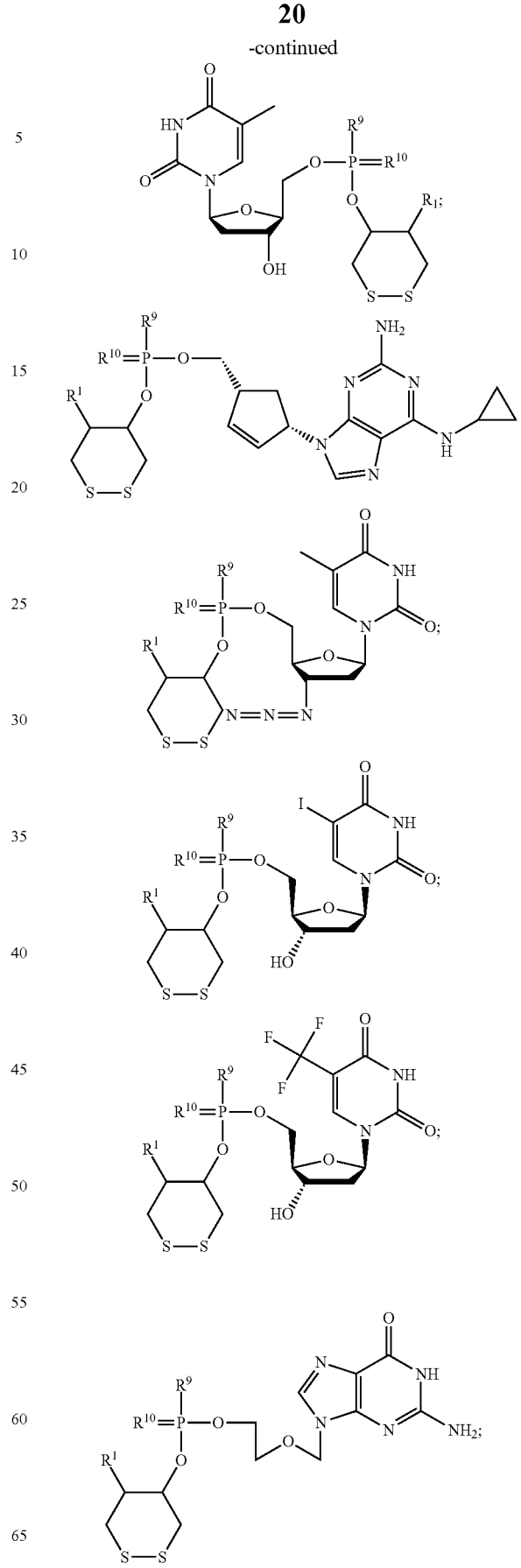

-continued
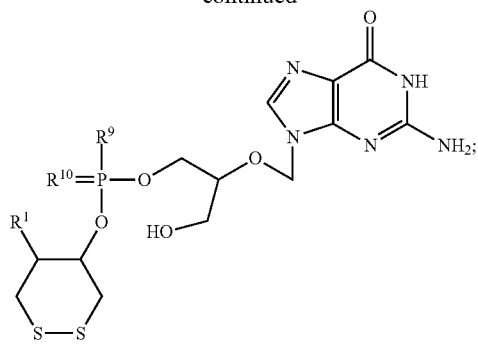
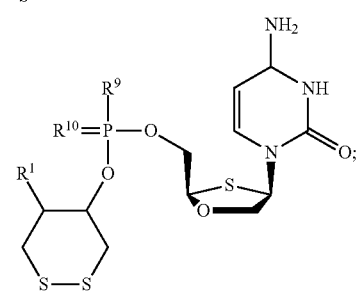
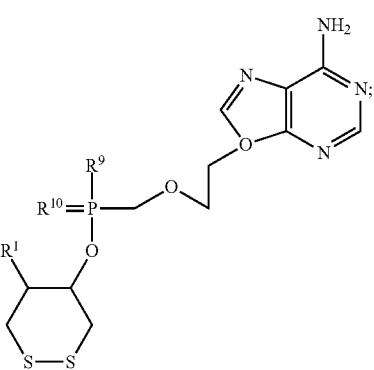
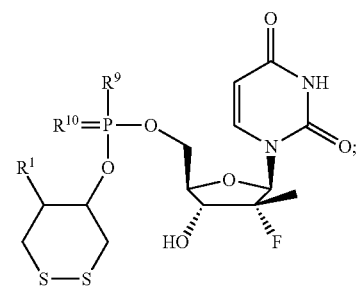
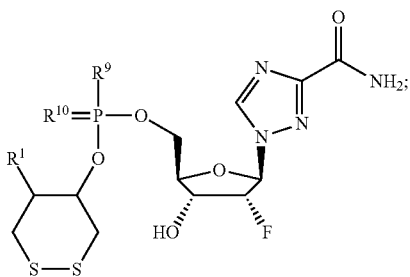
-continued
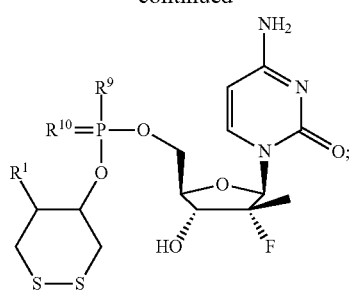
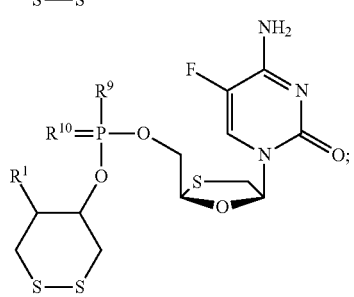
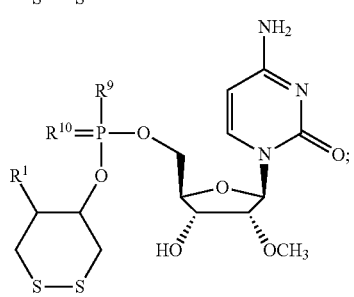
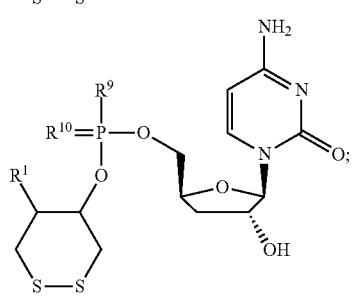
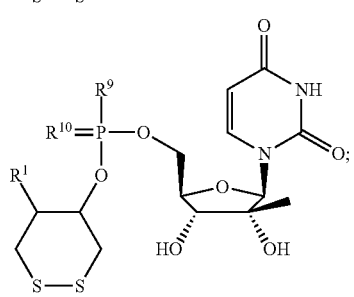
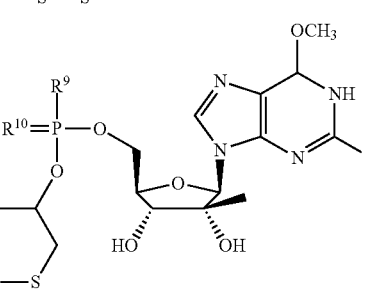

23
-continued
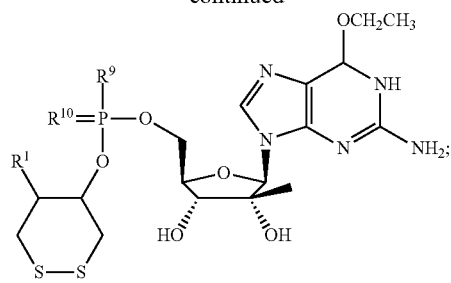
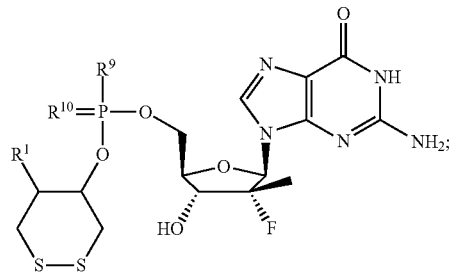
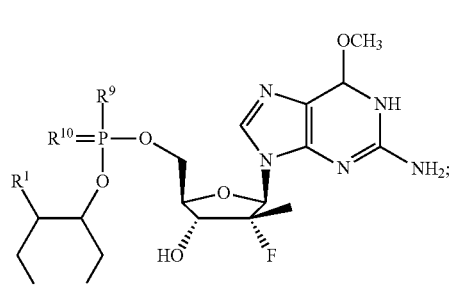
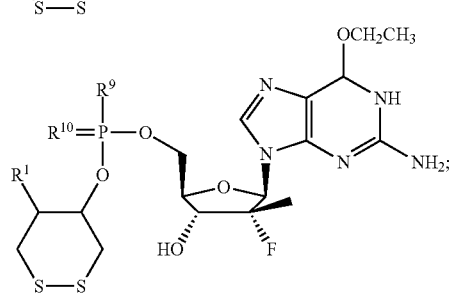
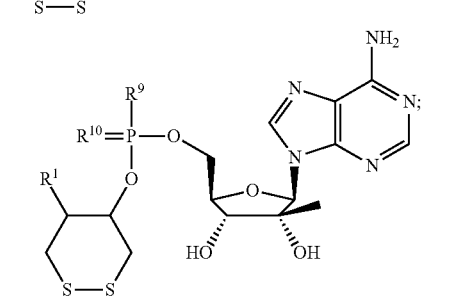
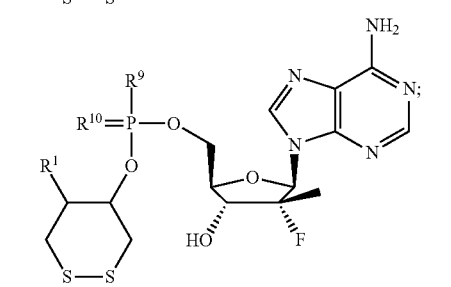
24
-continued
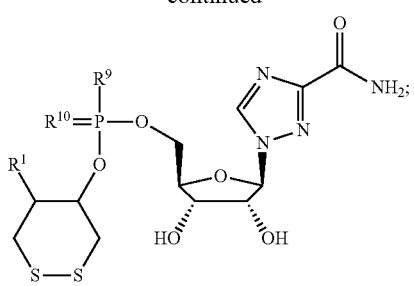
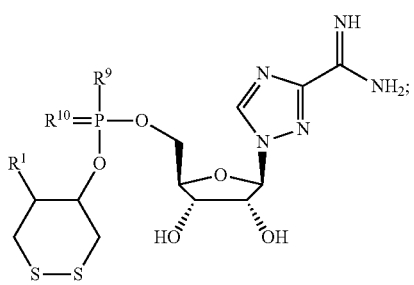
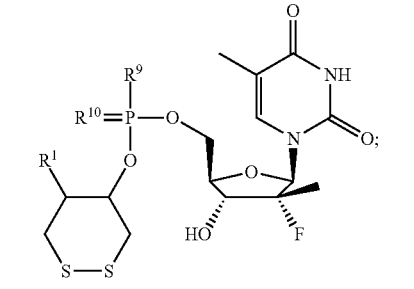
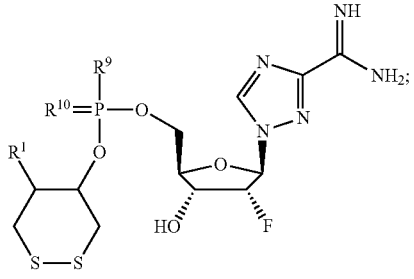
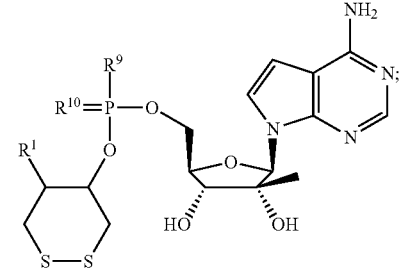
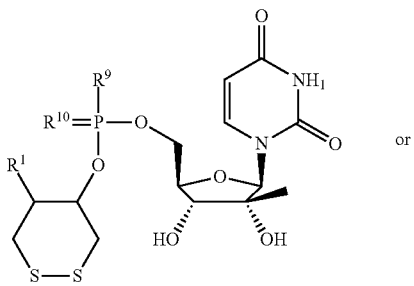 or -continued

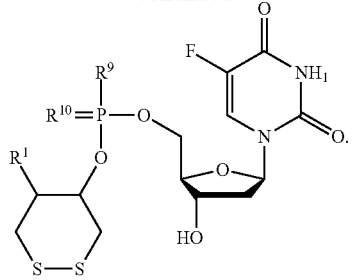

In one embodiment, a compound having Formula I is:

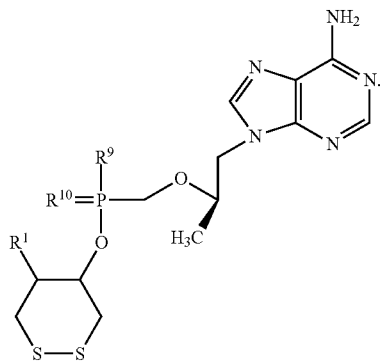

In certain embodiments, with reference to any compound having Formula I above, $R^9$ is:

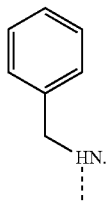

In certain embodiments, with reference to any compound having Formula I above, $R^9$ is:

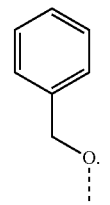

In certain embodiments, with reference to any compound having Formula I above, $R^9$ is:

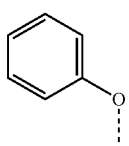

In certain embodiments, with reference to any compound having Formula I above, $R^9$ is:

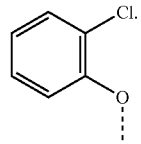

In certain embodiments, with reference to any compound having Formula I above, $R^9$ is:

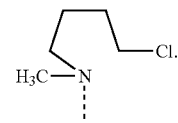

In certain embodiments, with reference to any compound having Formula I above, $R^{10}$ is O.

In certain embodiments, with reference to any compound having Formula I above, $R^{10}$ is S.

In certain embodiments, with reference to any compound having Formula I above, $R^1$ is X-L-Y; wherein X is O, S, NH, C(O), S(O), $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —$NHC_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl; L is a linker that is optionally present; and Y is a targeting agent, ligand and/or polymer that is optionally present.

Also provided herein are compounds having Formula II:

(Formula II)

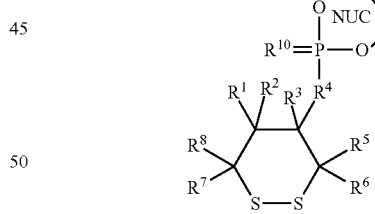

wherein,
$R^1$ is H, OH, $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —$NHC_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl, or X-L-Y;

wherein X is O, S, NH, C(O), S(O), $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —$NHC_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl; L is a linker that is optionally present; and Y is a targeting agent, ligand and/or polymer that is optionally present;

$R^4$ is S or O;

each $R^2$, $R^3$, $R^5$, $R^6$, $R^7$ and $R^8$ is independently halo or $R^1$ as above;

$R^{10}$ is S or O; and

NUC is a nucleoside, nucleoside analog, nucleotide, nucleotide analog, or nucleobase analog thereof.

In certain embodiments, a compound having Formula II is:

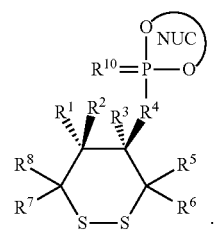

In certain embodiments, a compound having Formula II is:

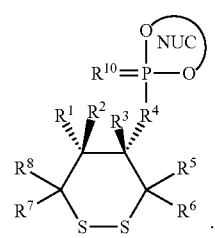

In certain embodiments, a compound having Formula II is:

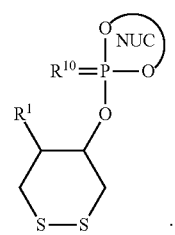

In certain embodiments, a compound having Formula II is:

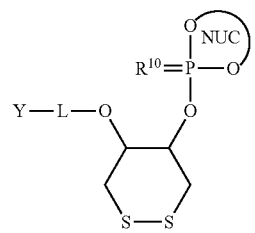

wherein L is a linker that is optionally present; and Y is a ligand and/or polymer.

In certain embodiments, a compound having Formula II is:

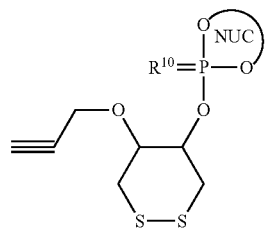

In certain embodiments, with reference to a compound having Formula II,

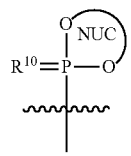

is:

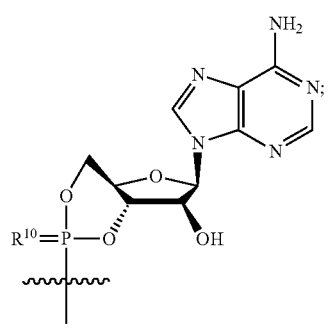

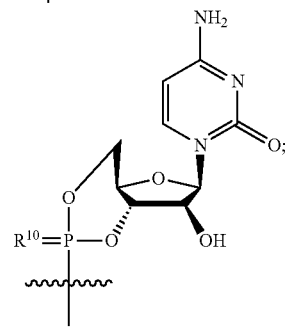

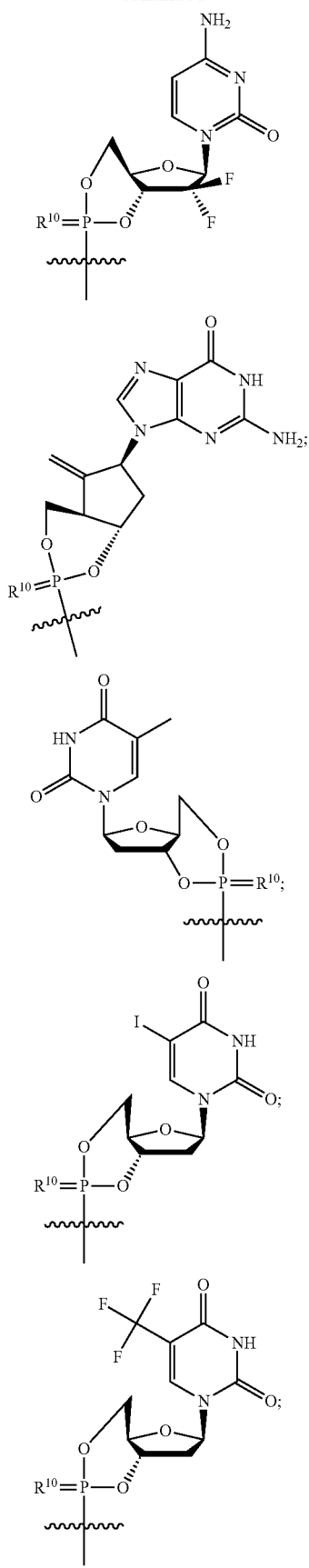
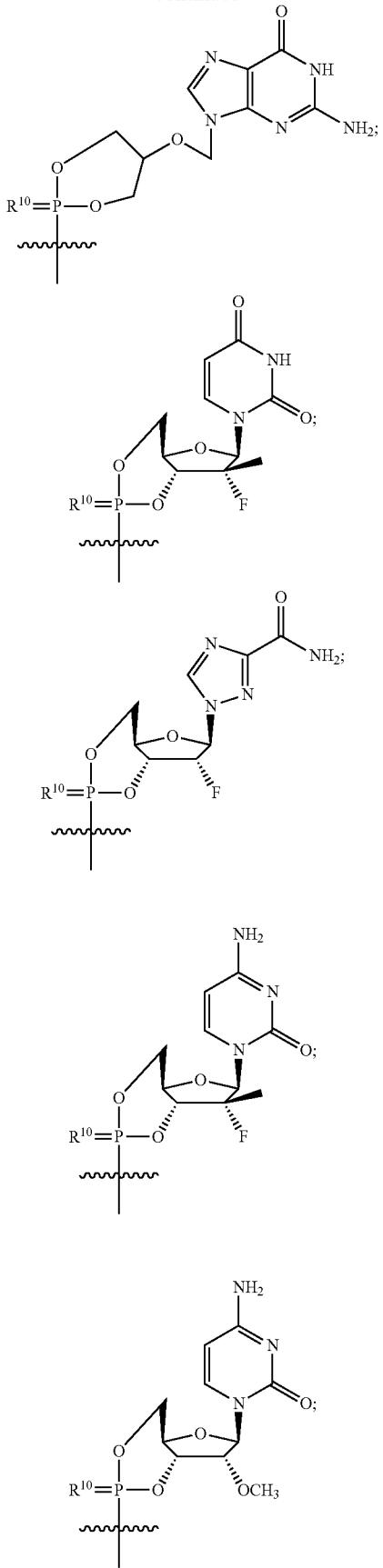

31
-continued
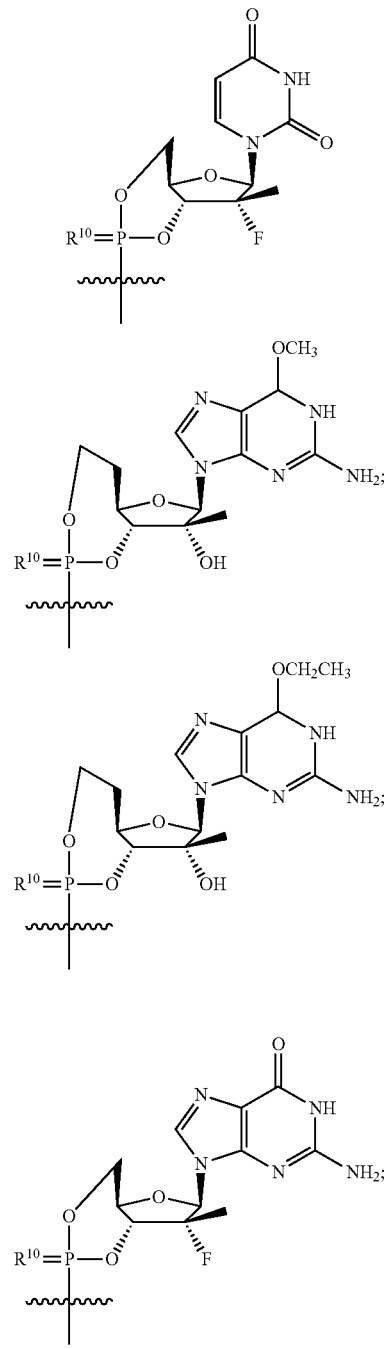
32
-continued
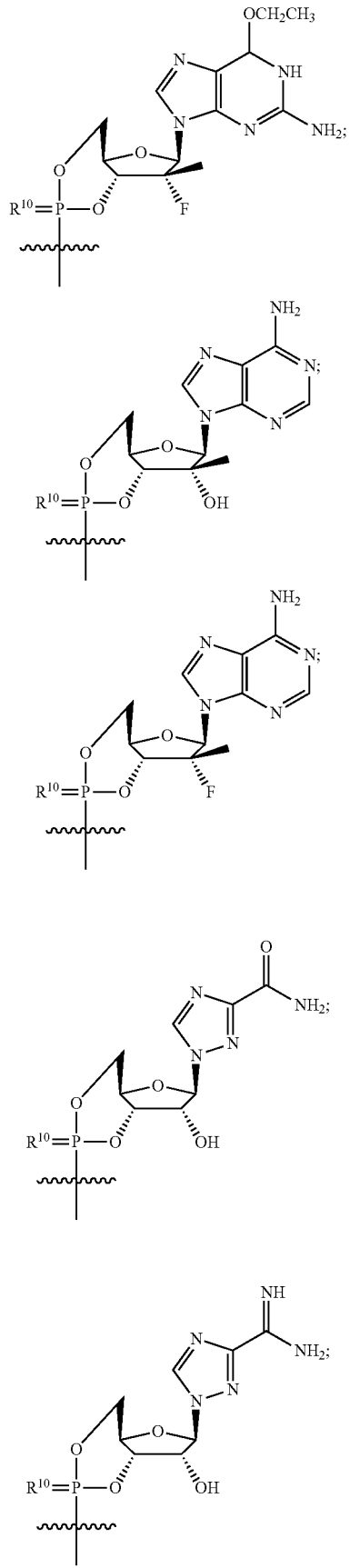

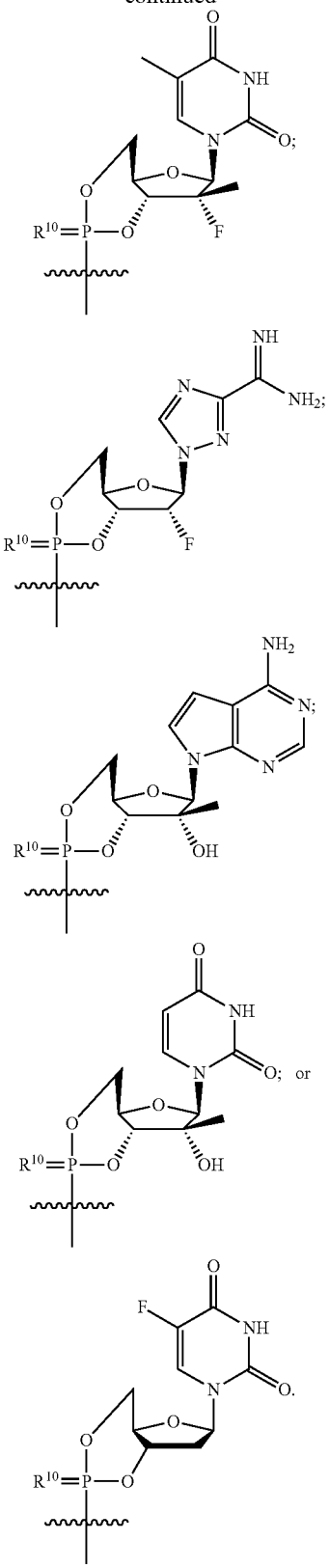
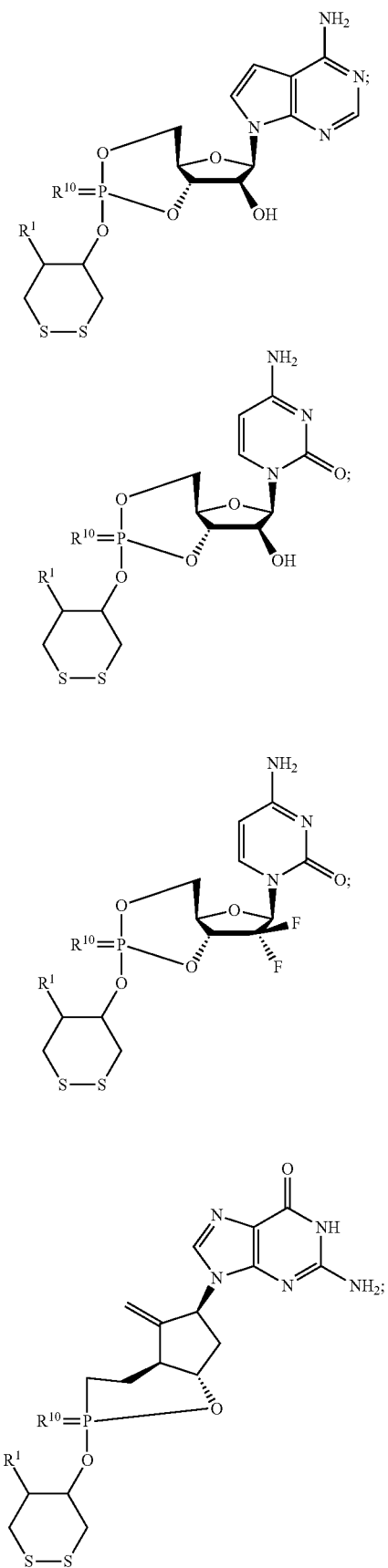
In certain embodiments, a compound having Formula II is:

35
-continued
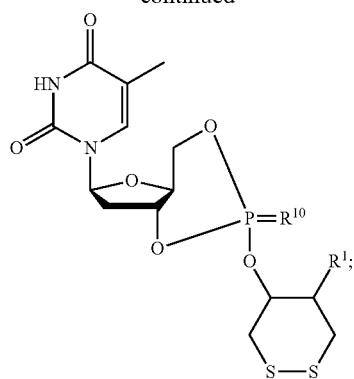
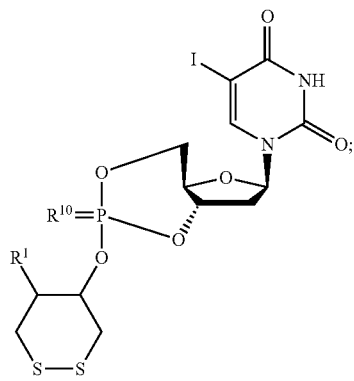
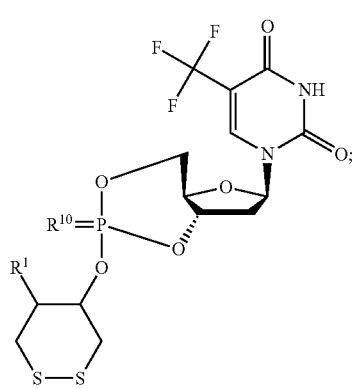
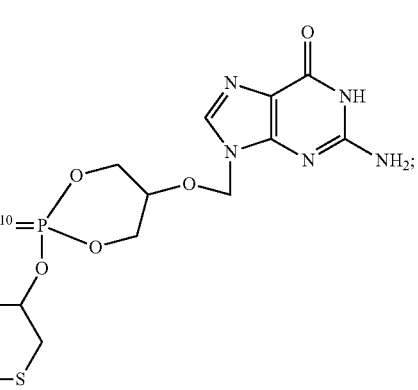
36
-continued
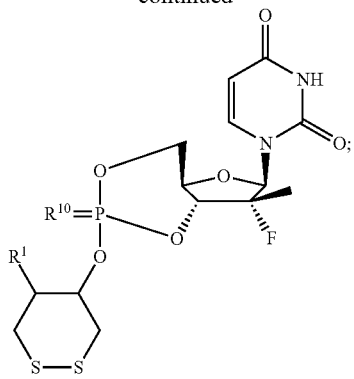
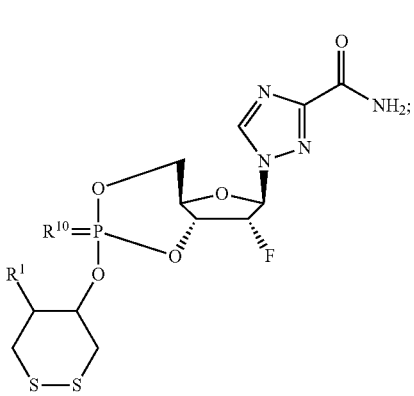
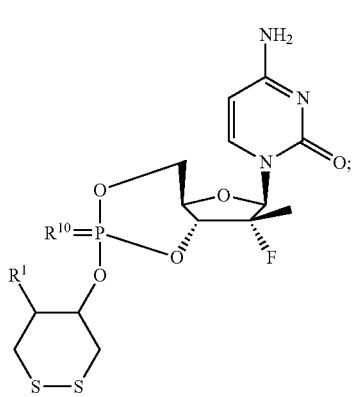
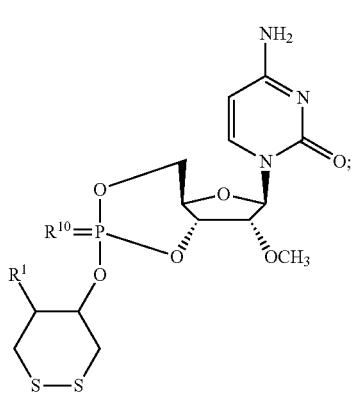

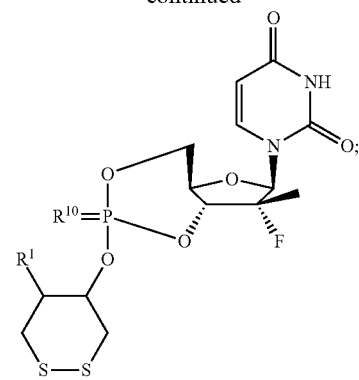
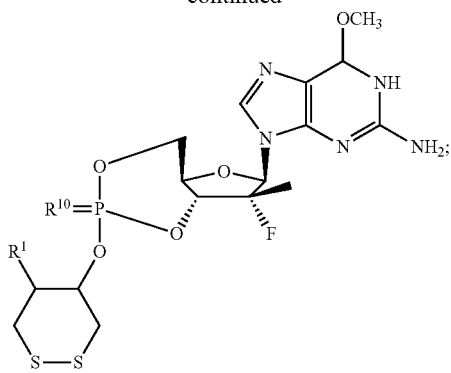
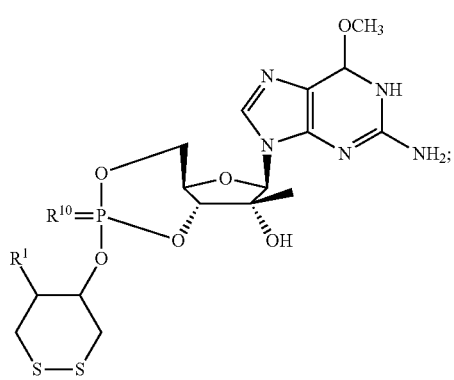
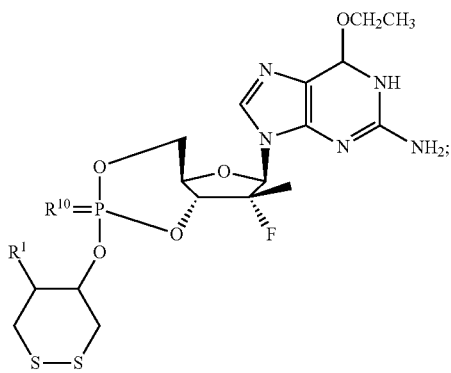
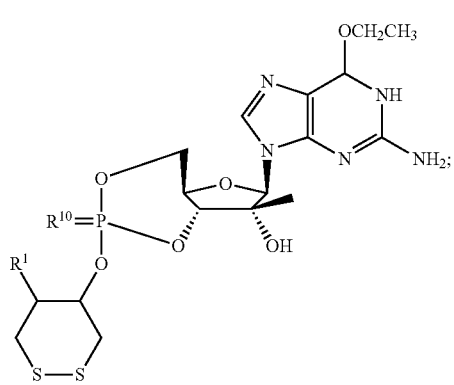
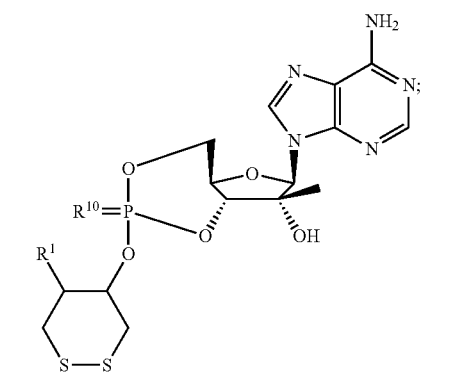
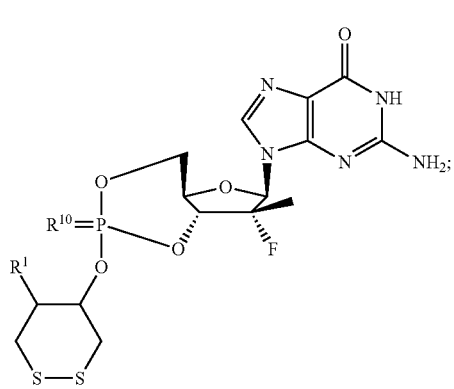
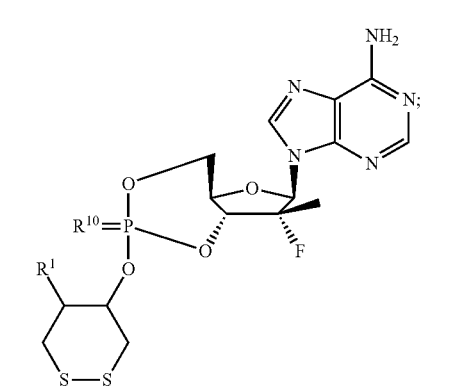

-continued

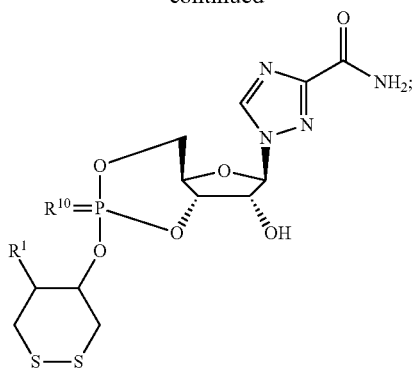

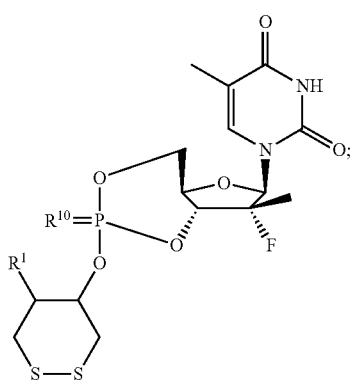

-continued

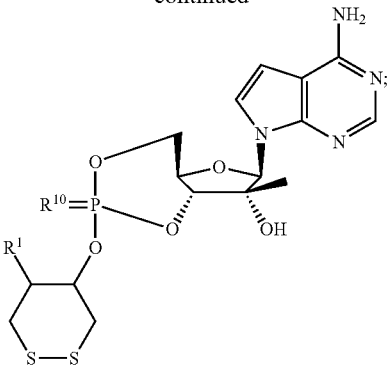

In certain embodiments, with reference to any compound having Formula II above, $R^{10}$ is O.

In certain embodiments, with reference to any compound having Formula II above, $R^{10}$ is S.

In certain embodiments, with reference to any compound having Formula I or II above, $R^1$ is X-L-Y; wherein X is O, S, NH, C(O), S(O), $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NH$C_{1-6}$ alkyl, aryl$C_{1-6}$ alkyl, heteroaryl$C_{1-6}$ alkyl, heterocyclyl$C_{1-6}$ alkyl, guanidinyl, $C_{1-6}$alkylC(O)O—, arylC(O)O—, heterocyclylC(O)O—, O-propargyl, S-propargyl, O-allyl, S-allyl; L is a linker that is optionally present; and Y is a targeting agent, ligand and/or polymer that is optionally present.

In certain embodiments, with reference to any compound having Formula I or II above, Y comprises one or more N-Acetyl Galactosamine moieties.

In certain embodiments, with reference to any compound having Formula I or II above, Y comprises one or more folate moieties.

In certain embodiments, with reference to any compound having Formula I or II above, Y comprises one or more peptide moieties.

In certain embodiments, with reference to any compound having Formula I or II above, Y comprises one or more steroid moieties.

In certain embodiments, with reference to any compound having Formula I or II above, Y comprises one or more vitamin or co-factor moieties.

In certain embodiments, with reference to any compound having Formula I or II above, Y comprises:

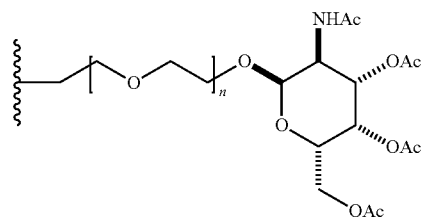

wherein n is an integer between 1 and 100.

In certain embodiments, with reference to any compound having Formula I or II above, Y comprises:

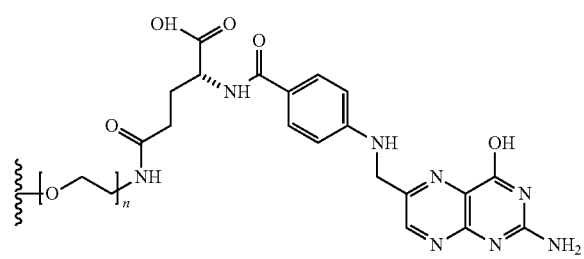

wherein n is an integer between 1 and 100.

In certain embodiments, with reference to any compound having Formula I or II above, Y comprises:

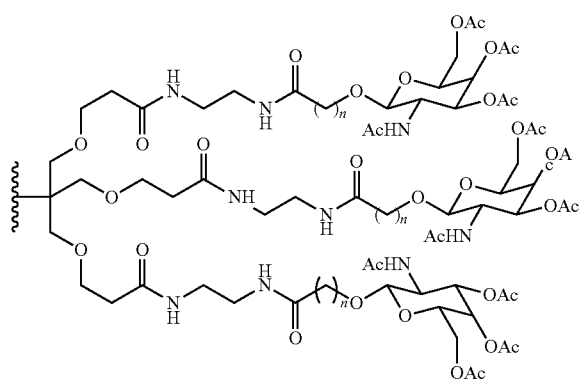

wherein each n is independently an integer from 1 to 20.

In certain embodiments, with reference to any compound having Formula I or II above, Y comprises:

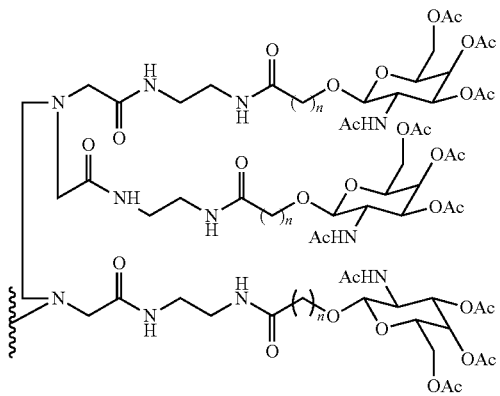

wherein each n is independently an integer from 1 to 20.

In certain embodiments, with reference to any compound having Formula I or II above, Y comprises:

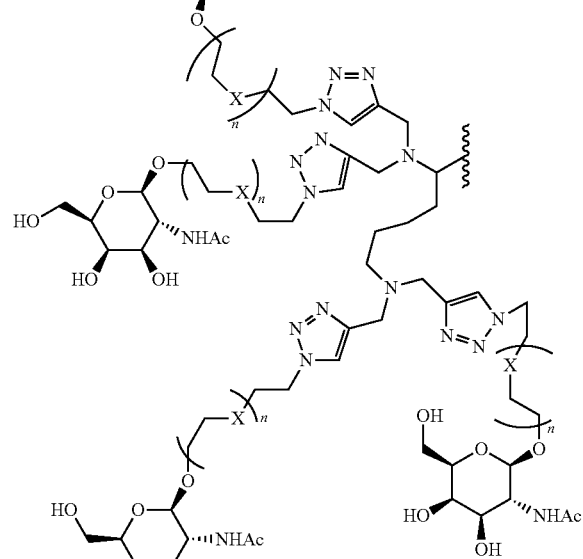

wherein X is —O—, —S—, —$CR^{11}R^{12}$— or —$NR^{11}$—, wherein $R^{11}$ and $R^{12}$ are each independently selected from the group consisting of hydrogen and C1-C6alkyl; n is 1, 2, 3, or 4.

In certain embodiments, with reference to any compound having Formula I or II above, Y comprises:

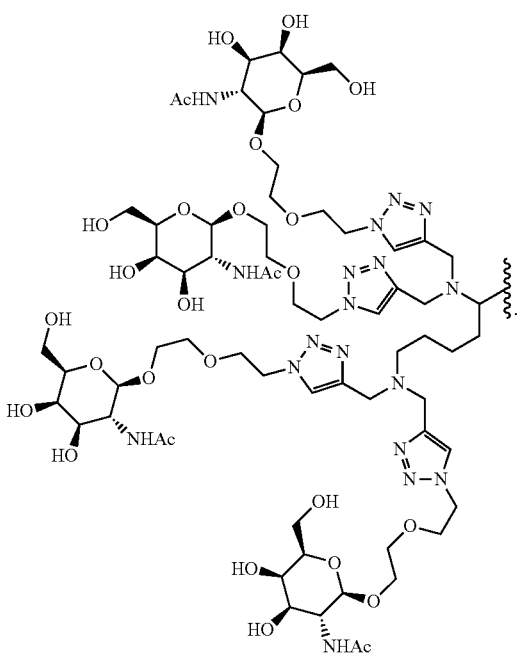 [SMILES: *C(CCCCN(Cc1cn(CCOCCO[C@@H]2O[C@H](CO)[C@H](O)[C@H](O)[C@H]2NC(C)=O)nn1)Cc1cn(CCOCCO[C@@H]2O[C@H](CO)[C@H](O)[C@H](O)[C@H]2NC(C)=O)nn1)N(Cc1cn(CCOCCO[C@@H]2O[C@H](CO)[C@H](O)[C@H](O)[C@H]2NC(C)=O)nn1)Cc1cn(CCOCCO[C@@H]2O[C@H](CO)[C@H](O)[C@H](O)[C@H]2NC(C)=O)nn1]

In certain embodiments, with reference to any compound having Formula I or II above, L is a linker comprising an alkyl, carbonyl, amide, phosphate, phosphate ester, phosphoramidate, thiophosphate ester, disulfide, or polyalklene glycol linkage.

In certain embodiments, the invention features a composition comprising any compound having Formula I or II above or a pharmaceutically acceptable salt, solvate, ester, or prodrug thereof.

In certain embodiments, the invention features a composition comprising any compound having Formula I or II above and a pharmaceutically acceptable carrier or diluent.

C. Therapeutic Applications

In certain applications, the compounds and compositions of the invention are applied for therapeutic use.

Thus, one aspect of the invention comprises a method of treating a subject including, but not limited to, a human suffering from a disease or a condition, which method comprises administering to said subject an effective amount of a compound or composition of the invention. In one embodiment of this aspect, the compound comprises any of Formula I or II herein.

In certain embodiments, the invention features the use of a therapeutically effective amount of at least one compound having Formula I or II above, or a pharmaceutically acceptable salt, solvate, ester or prodrug thereof, for the manufacture of a medicament for treatment of a patient in need thereof.

In certain embodiments, the invention features the use of a therapeutically effective amount of at least one compound having Formula I or II above, or a pharmaceutically acceptable salt, solvate, ester or prodrug thereof, for the treatment of a patient in need thereof.

In certain embodiments, the invention features the use of a therapeutically effective amount of at least one compound having Formula I or II above, or a pharmaceutically acceptable salt, solvate, ester or prodrug thereof, for the treatment of viral infection in a patient in need thereof. Non-limiting examples of such viral infections include HCV, HBV, HPV, HSV or HIV infection.

In certain embodiments, the invention features the use of a therapeutically effective amount of at least one compound having Formula I or II above, or a pharmaceutically acceptable salt, solvate, ester or prodrug thereof, for the treatment of cancer in a patient in need thereof. Non-limiting examples of such cancers include bilary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, wilms tumor, leukemia, acute lymocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T-cell lymphomas, non-Hodgkin lymphoma, precursor T-lymphoblastic lymphoma/leukemia, peripheral T-cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas, Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

In some embodiments of this aspect, therapeutic use is for treatment of a disease or condition. The disease or condition may be cancer, a proliferative, inflammatory, autoimmune, neurologic, ocular, respiratory, metabolic, dermatological, auditory, liver, kidney, or infectious disease as described herein or otherwise known in the art. Thus, in certain embodiments the compounds and compositions of the instant invention may be useful in a method for treating cancer, proliferative, inflammatory, autoimmune, neurologic, ocular, respiratory, metabolic, dermatological, auditory, liver, kidney, or infectious diseases.

In certain embodiments, the administration of the compound or composition may be via local administration or systemic administration. In other embodiments, the invention features contacting the subject or organism with a compound or composition of the invention via local administration to relevant tissues or cells, such as lung cells and tissues, such as via pulmonary delivery. In yet other embodiments, the invention features contacting the subject or organism with a compound or composition of the invention via systemic administration (such as via intravenous or subcutaneous administration) to relevant tissues or cells in a subject or organism.

Compounds and compositions of the invention may also used as reagents in ex vivo applications. For example, a compound or composition may be introduced into tissue or cells that are transplanted into a subject for therapeutic effect. The cells and/or tissue may be derived from an organism or subject that later receives the explant, or may be derived from another organism or subject prior to transplantation. The compound or composition may be used to modulate the expression of one or more genes in the cells or tissue, such that the cells or tissue obtain a desired phenotype or are able to perform a function when transplanted in vivo. In one embodiment, certain target cells from a patient are extracted. These extracted cells are contacted with compounds of the invention targeting a specific nucleotide sequence within the cells under conditions suitable for uptake of the compounds by these cells (e.g., using delivery reagents such as cationic lipids, liposomes and the like or using techniques such as electroporation to facilitate the delivery of compounds into cells). The cells are then reintroduced back into the same patient or other patients.

For therapeutic applications, a pharmaceutically effective dose of the compound or pharmaceutical composition of the invention is administered to the subject. A pharmaceutically effective dose is that dose required to prevent, inhibit the occurrence, or treat (alleviate a symptom to some extent, preferably all of the symptoms) a disease state. One skilled in the art may readily determine a therapeutically effective dose of the compound or composition of the invention to be administered to a given subject, by taking into account factors, such as the size and weight of the subject, the extent of the disease progression or penetration, the age, health, and sex of the subject, the route of administration, and whether the administration is regional or systemic. Generally, an amount between 0.1 μg/kg and 140 mg/kg body weight/day of active ingredients is administered dependent upon potency of the compounds of the disclosure. The amount of active ingredient that may be combined with the carrier materials to produce a single dosage form varies depending upon the host treated and the particular mode of administration. Optimal dosing schedules may be calculated from measurements of drug accumulation in the body of the patient. The compounds and compositions of the invention may be administered in a single dose or in multiple doses.

A compound or composition of the instant invention may be administered once monthly, once weekly, once daily (QD), or divided into multiple monthly, weekly, or daily doses, such as, for example, but not limitation, twice daily (BID), three times daily (TID), once every two weeks. Persons of ordinary skill in the art may easily estimate repetition rates for dosing based on measured residence times and concentrations of the drug in bodily fluids or tissues.

In addition, the administration may be continuous, i.e., every day, or intermittently. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

D. Administration

Compositions or formulations of the invention may be administered in a variety of ways. Non-limiting examples of administration methods of the invention include oral, buccal, sublingual, parenteral (i.e., intraarticularly, intravenously, intraperitoneally, subcutaneously, or intramuscularly), local rectal administration or other local administration. In one embodiment, the composition of the invention may be administered by insufflation and inhalation. Administration may be accomplished via single or divided doses. In some embodiments, the pharmaceutical compositions are administered intravenously or intraperitoneally by a bolus injection (see, e.g., U.S. Pat. No. 5,286,634).

A composition of the invention with or without a vehicle may be locally delivered by direct injection or by use of an infusion pump. Direct injection of the compounds and compositions of this disclosure, whether subcutaneous, intramuscular, or intradermal, may take place using standard needle and syringe methodologies, or by needle free technologies, such as those described in Conroy et al, (1999, Clin. Cancer Res. 5:2330) and PCT Publication No. WO 99/31262. For example, but not by limitation, lipid particles comprising the compounds of the invention may be administered by direct injection at the site of disease or by injection at a site distal from the site of disease (see, e.g., Culver, HUMAN GENE THERAPY, MaryAnn Liebert, Inc., Publishers, New York. pp. 70-71(1994)). In one embodiment, the compounds of the invention and formulations or compositions thereof are administered to a cell, subject, or organism as is described herein and as is generally known in the art.

In Vivo Administration

In any of the methods of treatment of the invention, the compounds may be administered to the subject systemically as described herein or otherwise known in the art, either alone as a monotherapy or in combination with additional therapies described herein or as are known in the art. Systemic administration may include, for example, pulmonary (inhalation, nebulization etc.) intravenous, subcutaneous, intramuscular, catheterization, nasopharyngeal, transdermal, or oral/gastrointestinal administration as is generally known in the art.

In any of the methods of treatment or prevention of the invention, the compounds may be administered to the subject locally or to local tissues as described herein or otherwise known in the art, either alone as a monotherapy or in combination with additional therapies as are known in the art. Local administration may include, for example, inhalation, nebulization, catheterization, implantation, direct injection, dermal/transdermal application, patches, stenting, ear/eye drops, or portal vein administration to relevant tissues, or any other local administration technique, method or procedure, as is generally known in the art.

In one embodiment, the compounds of the invention and formulations or compositions thereof are administered to the liver as is generally known in the art (see for example Wen et al., 2004, World J Gastroenterol., 10, 244-9; Murao et al., 2002, Pharm Res., 19, 1808-14; Liu et al., 2003, gene Ther., 10, 180-7; Hong et al., 2003, J Pharm Pharmacol., 54, 51-8; Herrmann et al., 2004, Arch Virol., 149, 1611-7; and Matsuno et al., 2003, gene Ther., 10, 1559-66).

In one embodiment, the invention features the use of methods to deliver the compounds of the instant invention to hematopoietic cells, including monocytes and lymphocytes. These methods are described in detail by Hartmann et al., 1998, J. Phamacol. Exp. Ther., 285(2), 920-928; Kronenwett et al., 1998, Blood, 91(3), 852-862; Filion and Phillips, 1997, Biochim. Biophys. Acta., 1329(2), 345-356; Ma and Wei, 1996, Leuk. Res., 20(11/12), 925-930; and Bongartz et al., 1994, Nucleic Acids Research, 22(22), 4681-8.

In one embodiment, the compounds of the invention and formulations or compositions thereof are administered directly or topically (e.g., locally) to the dermis or follicles as is generally known in the art (see for example Brand, 2001, Curr. Opin. Mol. Ther., 3, 244-8; Regnier et al., 1998, J. Drug Target, 5, 275-89; Kanikkannan, 2002, BioDrugs, 16, 339-47; Wraight et al., 2001, Pharmacol. Ther., 90, 89-104; and Preat and Dujardin, 2001, STP PharmaSciences, 11, 57-68). In one embodiment, the compounds of the invention and formulations or compositions thereof are administered directly or topically using a hydroalcoholic gel formulation comprising an alcohol (e.g., ethanol or isopropanol), water, and optionally including additional agents such as isopropyl myristate and carbomer 980. In other embodiments, the compounds are formulated to be administered topically to the nasal cavity. Topical preparations may be administered by one or more applications per day to the affected area; over skin areas occlusive dressings may advantageously be used. Continuous or prolonged delivery may be achieved by an adhesive reservoir system.

In one embodiment, compounds of the invention are administered iontophoretically, for example to a particular organ or compartment (e.g., the eye, back of the eye, heart, liver, kidney, bladder, prostate, tumor, CNS etc.). Non-limiting examples of iontophoretic delivery are described in, for example, WO 03/043689 and WO 03/030989, which are incorporated by reference in their entireties herein.

In one embodiment, the compounds of the invention and formulations or compositions thereof are administered to the lung as is described herein and as is generally known in the art. In another embodiment, the siNA molecules of the invention and formulations or compositions thereof are administered to lung tissues and cells as is described in U.S. Patent Publication Nos. 2006/0062758; 2006/0014289; and 2004/0077540.

Aerosols and Delivery Devices
Aerosol Formulations

The compounds of the present invention, either alone or in combination with other suitable components, may be made into aerosol formulations (i.e., they may be "nebulized") to be administered via inhalation (e.g., intranasally or intratracheally) (see, Brigham et al., Am. J. Sci., 298:278 (1989)). Aerosol formulations may be placed into pressurized acceptable propellants, such as dichlorodifluoromethane, propane, nitrogen, and the like.

In one embodiment, the compounds of the invention and formulations thereof are administered via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized compounds may be prepared by grinding dried or lyophilized compositions, and then passing the micronized composition through, for example, a 400 mesh screen to break up or separate out large agglomerates. A solid particulate composition comprising the compounds of the invention may optionally contain a dispersant which serves to facilitate the formation of an aerosol as well as other therapeutic compounds. A suitable dispersant is lactose, which may be blended with the compound in any suitable ratio, such as a 1 to 1 ratio by weight.

Spray compositions comprising compounds or compositions of the invention may, for example, be formulated as aqueous solutions or suspensions or as aerosols delivered from pressurized packs, such as a metered dose inhaler, with the use of a suitable liquefied propellant. In one embodiment, aerosol compositions of the invention suitable for inhalation may be either a suspension or a solution and generally contain an compound of the invention and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants. Non-limiting examples include oleic acid, lecithin or an oligolactic acid or derivative such as those described in WO94/21229 and WO98/34596 and co-solvents for example ethanol. In one embodiment a pharmaceutical aerosol formulation of the invention comprising a compound of the invention and a fluorocarbon or hydrogen-containing chlorofluorocarbon or mixtures thereof as propellant, optionally in combination with a surfactant and/or a co-solvent.

The aerosol formulations of the invention may be buffered by the addition of suitable buffering agents.

Aerosol formulations may include optional additives including preservatives if the formulation is not prepared sterile. Non-limiting examples include, methyl hydroxybenzoate, anti-oxidants, flavorings, volatile oils, buffering agents and emulsifiers and other formulation surfactants. In one embodiment, fluorocarbon or perfluorocarbon carriers are used to reduce degradation and provide safer biocompatible non-liquid particulate suspension compositions of the invention. In another embodiment, a device comprising a nebulizer delivers a composition of the invention comprising fluorochemicals that are bacteriostatic thereby decreasing the potential for microbial growth in compatible devices.

Capsules and cartridges comprising the composition of the invention for use in an inhaler or insufflator, of for example gelatin, may be formulated containing a powder mix for inhalation of a compound of the invention and a suitable powder base such as lactose or starch. In one embodiment, each capsule or cartridge contains a compound of the invention and one or more excipients. In another embodiment, the compound of the invention may be presented without excipients such as lactose The aerosol compositions of the present invention may be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. In one embodiment, the particulate range may be from 1 to 5 microns. In another embodiment, the particulate range may be from 2 to 3 microns. Particles of non-respirable size which are included in the aerosol tend to deposit in the throat and be swallowed, and the quantity of non-respirable particles in the aerosol is thus minimized. For nasal administration, a particle size in the range of 10-500 um is preferred to ensure retention in the nasal cavity.

In some embodiments, compounds of the invention are administered topically to the nose for example, for the treatment of rhinitis, via pressurized aerosol formulations, aqueous formulations administered to the nose by pressurized pump or by nebulization. Suitable formulations may contain water as the diluent or carrier for this purpose. In certain embodiments, the aqueous formulations for administration of the composition of the invention to the lung or nose may be provided with conventional excipients such as buffering agents, tonicity modifying agents and the like.

Devices

The compounds of the invention may be formulated and delivered as particles and/or aerosols as discussed above and dispensed from various aerosolization devices known by those of skill in the art.

Aerosols of liquid or non-liquid particles comprising a compound or formulation of the invention may be produced by any suitable means, such as with a device comprising a nebulizer (see for example U.S. Pat. No. 4,501,729) such as ultrasonic or air jet nebulizers.

Solid particle aerosols comprising a compound or formulation of the invention and surfactant may be produced with any solid particulate aerosol generator. One type of solid particle aerosol generator used with the compounds of the invention is an insufflator. A second type of illustrative aerosol generator comprises a metered dose inhaler ("MDI"). MDIs containing compounds or formulations taught herein may be prepared by methods of the art (for example, see Byron, above and WO96/32099).

The compounds may also be formulated as a fluid formulation for delivery from a fluid dispenser, such as those described and illustrated in WO05/044354. In certain embodiments of the invention, nebulizer devices are used in applications for conscious, spontaneously breathing subjects, and for controlled ventilated subjects of all ages. The nebulizer devices may be used for targeted topical and systemic drug delivery to the lung. In one embodiment, a device comprising a nebulizer is used to deliver a compound or formulation of the invention locally to lung or pulmonary tissues. In another embodiment, a device comprising a nebulizer is used to deliver a compound or formulation of the invention systemically.

E. Examples

The invention will now be illustrated with the following non-limiting examples. Those of skill in the art will readily recognize a variety of non-critical parameters which can be changed or modified to yield essentially the same results.

Chemistry

Glutathione (1-1, GSH, Scheme 1) is a naturally occurring water soluble tripeptide, consisting of amino acids glycine, cystein and an unusually connected (γ-) glutamic acid. It can undergo a facile oxidation to form a dimer (1-2, glutathion disulfide, GSSG, Scheme 1) and hence it is a powerful reducing agent. The free thiol group present in its reduced form is an active nucleophile, therefore GSH is also effective in quenching reactive electrophiles. Both of these properties bode well for its main role of protecting cells against oxidative stress presented by free radicals, peroxides and other toxins (see Anderson, M. E., "Glutathione: an overview of biosynthesis and Modulation", Chemico-Biological Interactions 111-112, 1-14, 1998).

Scheme 1

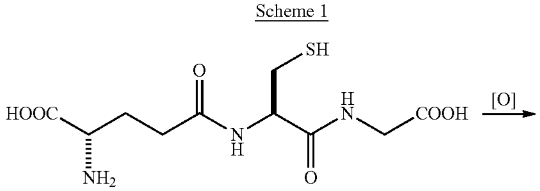

1-1

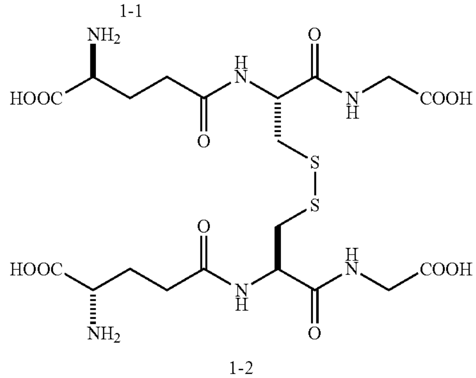

1-2

Most of glutathione present in the cell cytoplasm in the form of the reduced monomer 1-1 and the amount of dimer does not normally exceed 1%. This highly reductive intracellular environment is maintained by the action of the NADPH-dependent glutathion disulfide reductase. Glutathione itself is synthesized only inside of cells from its constituents by the ATP-dependent glutamate-cysteine ligase and glutathione synthase. Presence of the unusual γ-glutamate bond makes GSH resistant to most catabolic peptidases resulting in high intracellular stability. Its degradation is mediated by the γ-glutamyl transpeptiase (γ-GT) operating in the extracellular space. This ultimately leads to glutathione's ubiquitous intracellular presence and rather low extracellular concentration (Townsend, D. M., et al, "The Importance of Glutathione in Human Disease", Biomedicine & Pharmacology, 57, 145-155, 2003). Not surprisingly, elevated intracellular concentrations of glutathione were detected in tumor cells and this upregulation is considered to be an important component of cellular transformations leading to resistance to radiation and chemotherapy (Singh, S. et al., "Role of Glutathion in Cancer Pathophysiology and Therapeutic Interventions", Journal of Experimental Therapeutics and Oncology, 9, 303-316, 2012).

The universal intracellular presence and extracellular absence of glutathione present an potentially useful chemical trigger which can be exploited for intracellular release of active drug components from their inactive prodrug form. In addition, connecting this chemical, non-enzymatic release trigger to a targeting ligand offers an attractive approach to engage therapeutically relevant intracellular targets in a tissue-specific manner. An example of such an approach is Vintafolide, in which the targeting ligand (folic acid) is connected through a tethered, reductively cleaved disulfide to chemotherapeutically active payload (vinblastin), see Dosio, F., et al, "EC-145, a folate-targeted Vinca alkaloid conjugate for the potential treatment of folate receptor-expressing cancers", Current Opinion in Investigational Drugs, 11(12):1424-33, 2010.

Linear disulfide bonds have been used in various conjugation technologies as bioreducible linkers (Saito, G., et al, "Drug Delivery Strategy Utilizing Conjugation via Reversible Disulfide Linkages: Role and Site of Cellular Reducing Activities", Advanced Drug Delivery Reviews, 55, 199-215, 2003). For example, Traversa Therapeutics described a linear disulfide based release mechanism of prodrugging oligonucleotides in WO 2010039543 A2 (2010). According to this, a disulfide bond connected via an ethoxyethyl linker to a leaving group (phosphodiester in this instance) could be reductively unmasked with concomitant release of thiomorpholine (2-3), Scheme 2. However, the high reactivity of linear disulfides makes this approach impractical when applied to small molecules.

Scheme 2

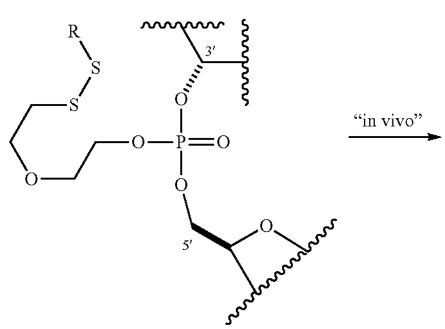

2-1

51
-continued

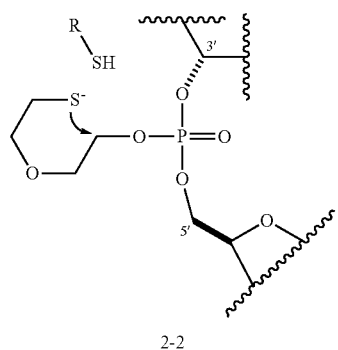

2-2

→ "spontaneous"

52
-continued

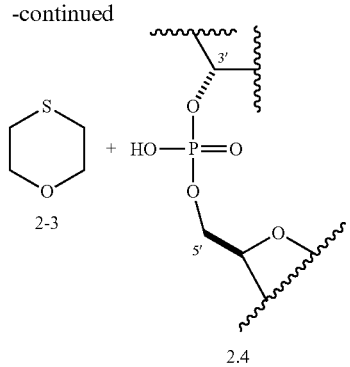

2-4

Standring, N. D et al., (Idenix Pharmaceuticals) described (Global Antivir. J., Suppl. 1:22, 2009) a similar cyclodeesterification driven release mechanism relevant to small molecules. According to this, an enzymatic ester cleavage of the nucleoside prodrug 3-1 was followed by a spontaneous cyclodeesterification of 3-2 with release of thiirane (3-3). Scheme 3.

Scheme 3

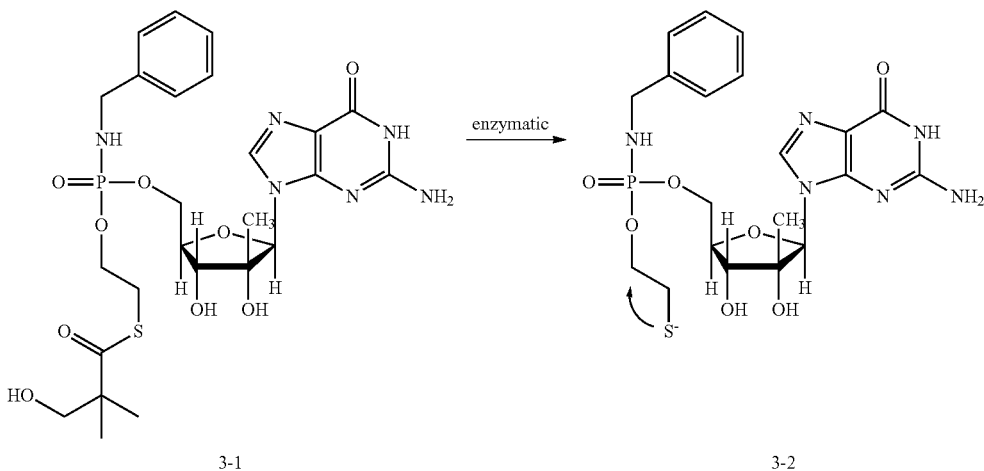

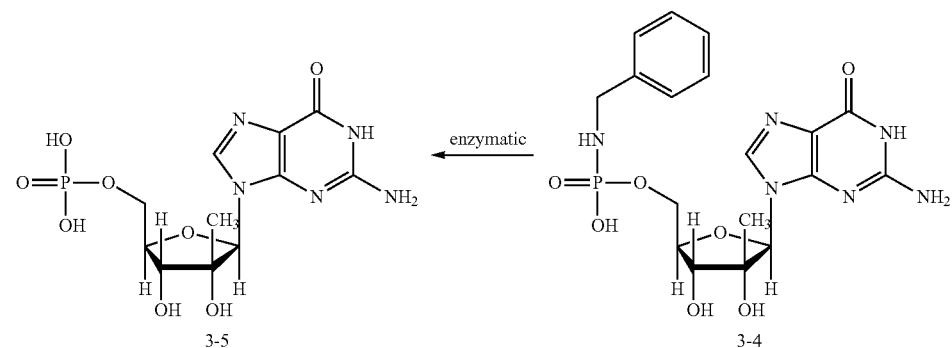

Similar deesterification was also reported by E. Gunic et al (Bioorg. Med. Chem. Lett., 17, 2452-2455, 2007). Once again, a enzyme mediated ester cleavage of nucleoside 4-1 produced the unstable phosphotriester 4-2, which spontaneously released the cyclic 3'-5'-phosphodiester 4-3 with concomitant formation of the reactive thiirane 3-3. One additional enzyme-mediated phosphodiester cleavage produced the monophosphate 4-4, Scheme 4.

Both of these procedures suggest that irrespective of the process the thioethoxy group present in examples 3-2 and 4-2 was generated, it will undergo a spontaneous ejection if connected to a leaving group (phosphate in this instance) and a reactive, potentially toxic thiirane (3-3) will be produced. In addition, the initial deesterification is mediated by ubiquitous esterases and tissue-selective release is difficult to achieve.

thiirane will self-quench via a 1,5-exo-tet ring closure to produce a stable tetrahydrothiophene derivative such as 5-3.

As opposed to linear disulfides, the cyclic disulfide contained within the dithiothreitol derivative 5-1 is chemically stable and this prodrug approach can be applied to therapeutically relevant molecules where intracellular delivery is desirable. The sharp distinction between the reductive environment of the cytoplasm and neutral milieu of the extracellular space bode well for site-specific drug release only after crossing the cell membrane.

Phosphate Prodrugs

We have chosen to demonstrate the utility of the present technology as it applies to phosphate leaving group using a nucleoside with well-established antiviral (HCV) properties: 2'-C-methyl-7-deaza adenosine (6-1a, Scheme 6, see Olsen, D. B. et al., Antimicrobial Agents and Chemotherapy "A

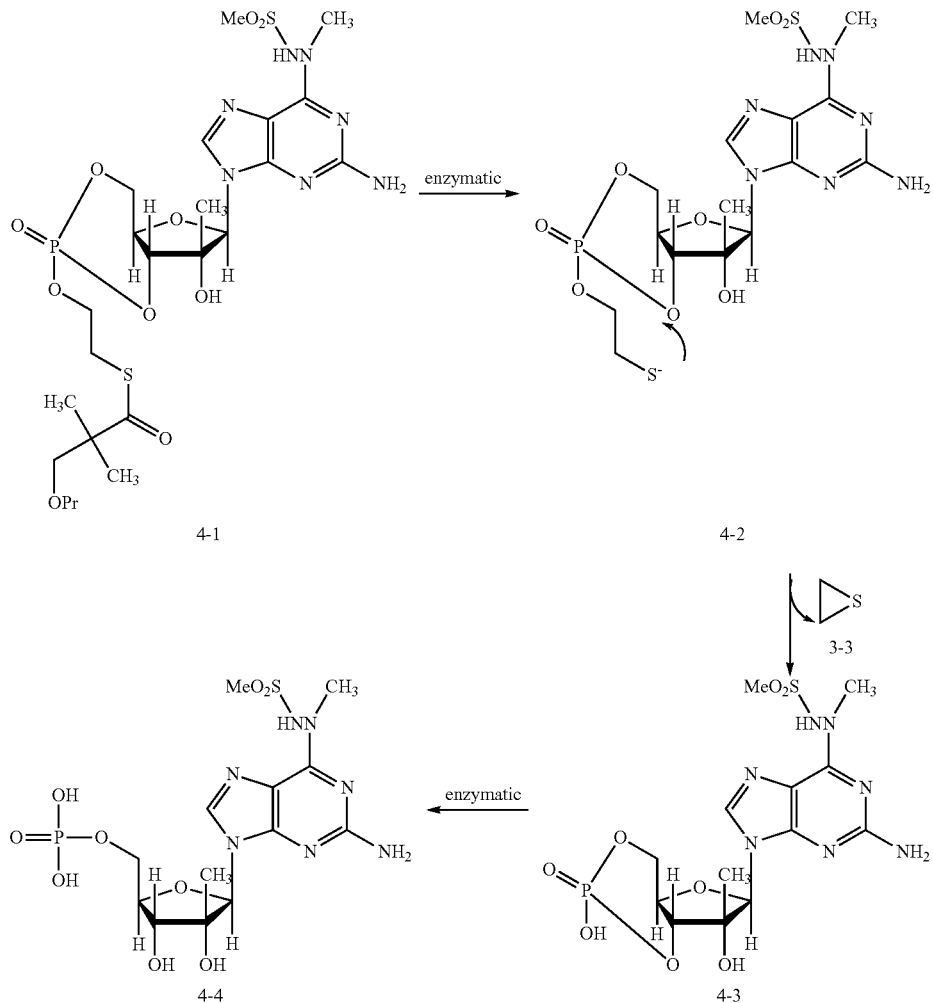

Scheme 4

The prodrugs disclosed herein have great advantages over known prodrugs such as those discussed above. As shown in FIG. 1, a negatively charged sulfur containing species, such as that generated from 5-1 by a glutathione mediated reduction will behave similarly and undergo a charge-dissipation driven cyclodeesterification. This will lead to ejection of a therapeutically relevant drug ("payload", 5-4) and a reactive 7-Deaza-Adenosine Analog Is a Potent and Selective Inhibitor of Hepatitis C Virus Replication with Excellent Pharmacokinetic Properties", 48(10), 3944, 2004 and Eldrup, A. B.; et al., "Structure-activity relationship of purine ribonucleosides for inhibition of hepatitis C virus RNA-dependent RNA polymerase", Journal of Medicinal Chemistry, 47(21), 5284, 2004) as well as 2'-C-methyl-uridine (6-1b, Scheme 6). The advantage of the latter lies in its diminished ability to undergo kinase-mediated conversion to the respective monophosphate (A. Cho et al. "Synthesis and characterization of 2'-C-Me branched C-nucleosides as HCV Polymerase Inhibitors", Bioorganic and Medicinal Chemistry Letters, 22 (2012) 4127-4132, see Table 1, 2'-C-Me-U GT1b $EC_{50}$=15.2 μM, while the respective triphosphate 2'-C-Me-U GT1b $EC_{50}$=1.32 μM). Its nucleoside triphosphate mediated antiviral potency is hence a more reliable indicator of the prodrug's ability to deliver the monophosphate, bypassing the first kinase. According to this, the commercially available dithiothreitol disulfide (6-6) was alkylated with a suitable alkyl halide such as propargyl or benzyl bromide under phase transfer conditions to yield monosubstituted dithiothreitol disulfide (6-7c,d). Its reaction with bis(diisopropylamino)chlorophosphine afforded the intermediate 6-8c,d, which was in turn, without isolation, reacted with nucleoside 6-1a or 6-1b. The purified phosphorous intermediate 6-2 was exposed to thioethyl tetrazole in aqueous acetonitrile to yield the H-phosphonate 6-4a,b. This was converted to the final product 6-5a or 6-5b using the Todd-Atherton reaction (see Georgiev, E. M., et al "An ab Initio Study of the Mechanism of the Atherton-Todd Reaction between Dimethyl Phosphonate and Chloro- and Fluoro-Substituted Methanes", Journal of the American Chemical Society, 115, 10964-10973, 1993) as shown in Scheme 6. It is relevant to note, that the phase transfer reaction yielding intermediate 6-7 is not limited to propargyl bromide and substituted or unsubstituted dithiothreitol or dithioerhythritol analogs may be used as substrates. Similarly, the Todd-Atherton reaction of 6-4 is by no means restricted to benzyl amine, and alternative primary or secondary amines may replace benzylamine.

Scheme 6

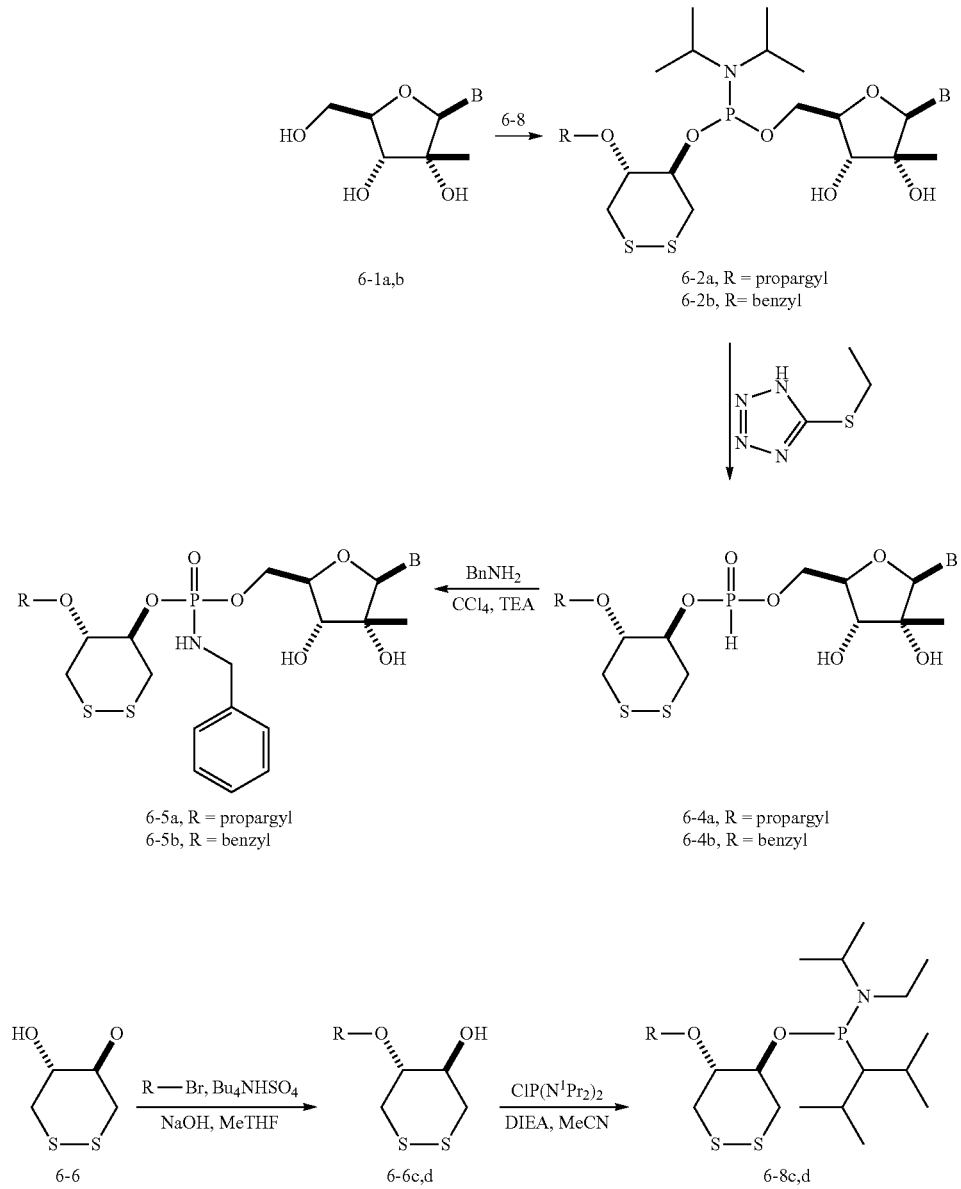

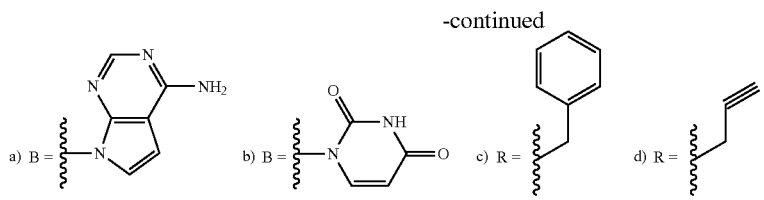

a) B = [7-deazaadenine]    b) B = [uracil]    c) R = benzyl    d) R = butynyl

The 3',5'-cyclic phosphotriester prodrugs were synthesized as depicted in Scheme 7. According to this, the P(III) intermediate 6-2, the preparation of which is described in Scheme 6, was internally cyclized at elevated temperature to yield the cyclic intermediate 7-1. This intermediate was oxidized with tert-butyl hydroperoxide to yield the final prodrug 7-2, or can alternately be oxidized with bis-phenylacetyl disulfide to yield the respective sulfur analog 7-3. Once again, the reaction is not limited to examples shown in Scheme 7, and may be successfully performed with analogs of 6-2, as discussed above.

Compounds such as 7-1 can be also prepared following the procedure described on Scheme 8. According to this, an unprotected nucleoside, such as 6-1a,b is reacted with bis-diisopropylphosphorous chloride in a suitable solvent such as dichloromethane at ambient temperature and cyclization of intermediate 8-1 is induced with DMAP. The cyclic phosphoramidite 8-2 can be isolated and used as a synthetic relay to access final compounds 7-2 more readily. This synthetic sequence was successfully applied to preparation of other cyclic 5'-3'-nucleoside prodrugs, such as those derived from 2'-fluoro-2'-methyl substituted ribose, such as 8-3 and 8-4 and 2-difluoro derivatives 8-5 and 8-6.

Scheme 7

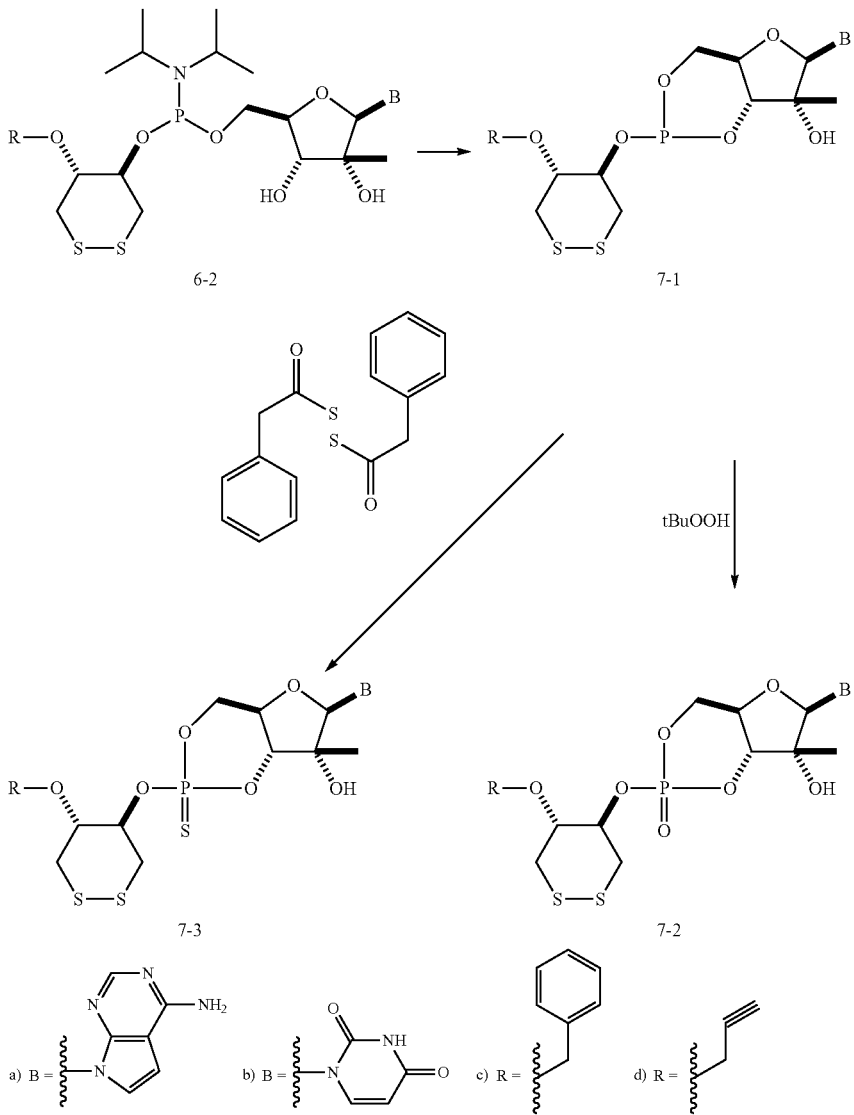

a) B = [7-deazaadenine]    b) B = [uracil]    c) R = benzyl    d) R = butynyl

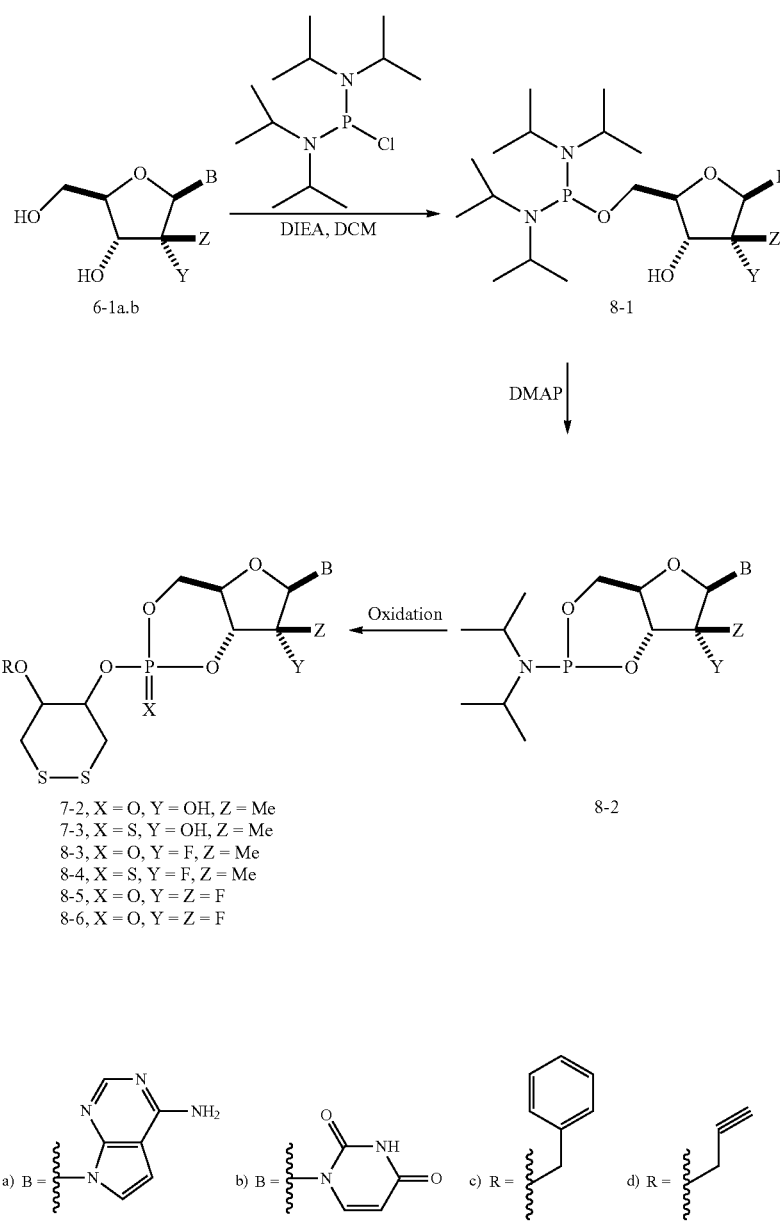

The acetylene group present in prodrugs 6-5a, Scheme 6, or 7-2 and 7-3 (R=propargyl, Scheme 7) may serve as a convenient handle to introduce groups to further enhance the therapeutic potential of these prodrugs, for example targeting ligands. N-acetyl galactosamine, which can bind to the asialoglycoprotein receptor (ASGPR), a membrane protein present in hepatic cells, may be used to mediate uptake of therapeutically relevant molecules to hepatocytes. The relevant chemistry is shown in Scheme 9. The N-acetyl galactosamine derivative 9-1 was exposed to dimethylamine at ambient temperature to induce removal of the acetyl protecting groups. Then, without additional purification, it was subjected to a Huisgen cycloaddition ("click reaction") with the propargyl group containing prodrug 7-2a,b to afford the final, targeting group containing nucleosides 9-2a,b.

Scheme 9

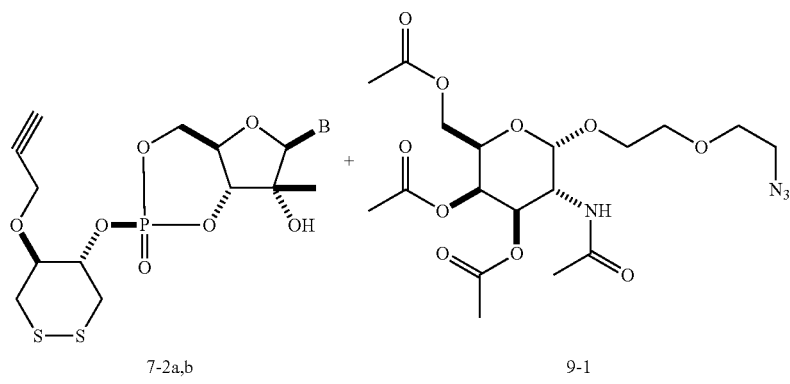

7-2a,b     9-1

1) dimethylar
2) Cu(I)

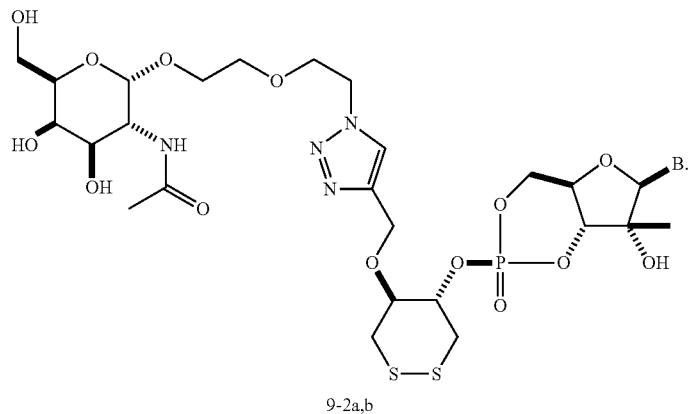

9-2a,b

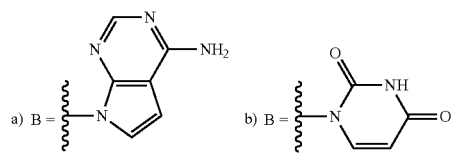

a) B =   b) B =

Phosphonate Prodrugs

Tenofovir (10-1, TFV, Scheme 10) is a truncated nucleoside derivative capable of inhibiting the viral reverse transcriptase (RT) of many viruses, which during their life cycle rely on the RT to transcribe the viral RNA into DNA. Important examples include among others the Human Immunodeficiency virus (HIV) and the virus responsible for hepatitis B (HBV). The compound was first synthesized in the laboratory of Antonin Holy (Institute of Organic Chemistry and Biochemistry, Czechoslovak Academy of Sciences) and its antiviral properties were recognized by Erik De Clercq (Rega Institute for Medicinal Research, University of Leaven, Belgium) (De Clercq, E., Holy, A., Rosenberg, I., Sakuma, T., Balzarini, J., Maudghal, P., "A Novel Selective Broad-Spectrum anti-DNA Virus Agent", Nature, vol. 323, p. 464, 1986).

Scheme 10

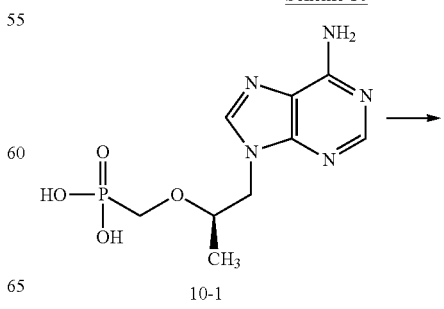

10-1

-continued

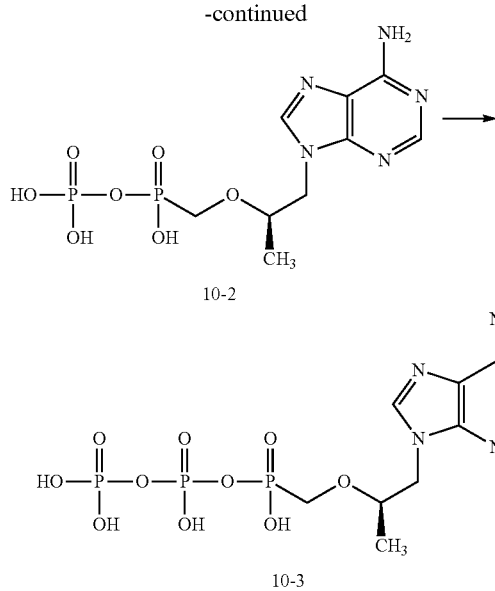

10-2

10-3

From the chemistry point of view, tenofovir is an adenosine derivative which contains a non-hydrolyzable phosphonate group. It mimics the phosphate group found in nucleoside monophosphates and can be converted by the action of nucleoside kinases to the respective phosphate (TFV-P, 10-2) and diphosphate (TFV-PP, 10-3) analogs, Scheme 10. Tenofovir diphosphate (TFV-PP, 10-3) resembles naturally occurring nucleoside triphosphates and can be incorporated into the nascent viral DNA chain during transcription which then leads to chain termination and interruption of the viral life cycle.

Permanent attachment of the phosphonate group to the truncated adenosine residue in TFV alleviates the necessity of the first, often rate limiting, kinase dependent phosphorylation step. On the other hand, the phosphonate group carries a negative charge at physiological pH, and it reduces the propensity of TFV to cross cell membranes. For this reason, the oral bioavailability of tenofovir is quite limited and its in vitro efficacy is quite low ($EC_{50}$=1.2 μM, HIV-1, PBMCs). At the same time, the active species, tenofovir diphosphate (10-3, Scheme 10) has high viral persistence, as its half-life in peripheral blood mononuclear cells (PBMCs) is in excess of 100 hours.

In order to deliver tenofovir to systemic circulation, various tenofovir-derivatives designed to re-convert back to active tenofovir after oral absorption were synthesized. These pro-drugs are typically phosphonate esters designed to release the active tenofovir after an enzymatically induced initial step. An example of this approach is the disoproxyl derivative of tenofovir (Tenofovir Disoproxyl Fumarate, TDF, 11-1, Scheme 11), marketed by Gilead as a one a day anti HIV reverse transcriptase inhibitor (Viread). The activation sequence of TDF is described in Sheme 11. According to this, one of the isopropyl ester groups of TDF is hydrolyzed by a naturally occurring hydrolase to produce an unstable semi-carbonate (11-2), which sequentially ejects carbon dioxide and formaldehyde. Parallel with this, the second ester group undergoes the same decomposition. The systematically released tenofovir (10-1) can then penetrate the cell membrane of PBMCs and be sequentially converted to the respective diphosphate (10-3). Alternatively, the phosphonate diester 11-1 can penetrate the cell membrane of PBMCs intact, and the ester mediated tenofovir release takes place intracellularly. The later event can result in higher TFV-PP levels, as the TFV mono- or di-esters can penetrate the cell membrane of PBMCS more readily than tenofovir itself.

Scheme 11

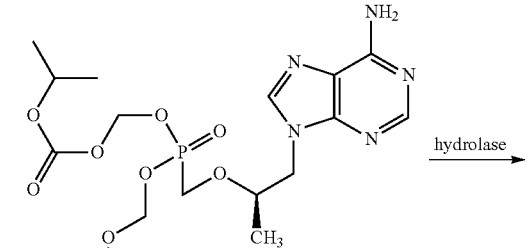

11-1

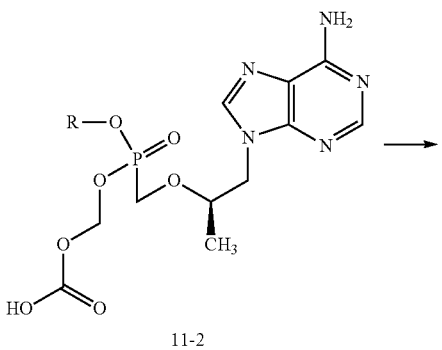

11-2

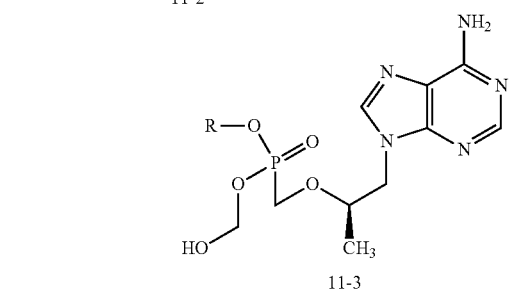

11-3

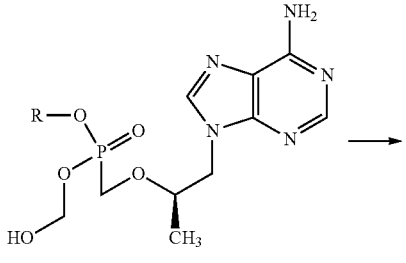

11-3

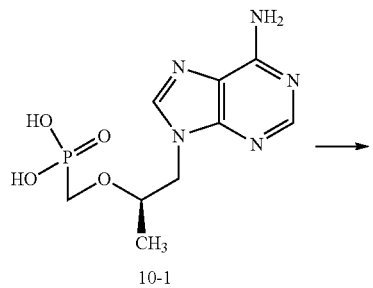

10-1

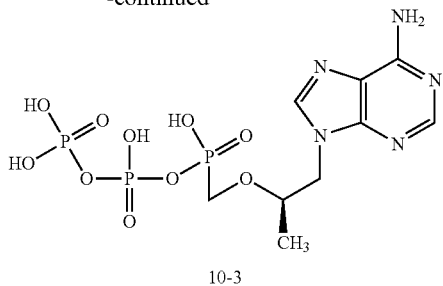

10-3

Alternative prodrugs of tenofovir are shown in Scheme 12. The phosphonoamidate prodrug 12-1 (Tenofovir Alafenamid Fumarate, TAF, Gilead) is also designed to initiate the tenofovir release by an esterase mediated isopropyl ester hydrolysis. This step is also efficiently performed by the action of cathepsin-A, a serine-protease operating the lysosomal compartment of cells. For this reason, most of the tenofovir is released intracellularly, resulting in much lower daily dose compared to TDF (Birkus, G., Kutty, N., He, G. H., Mulato, A., Lee, W., McDermott, M., Cihlar, T., "Activation of 9-[(R)-2-[[(S)-1-(Isopropyloxycarbonyl)ethtyl]amino]phenoxyphosphinyl]-methoxy]adenine (GS-7340) and Other Tenofovir Phosphonoamidate Prodrugs by Human Proteases.", Molecular Pharmacology, 74: 92-100, 2008). The phospholipid analog 12-2 (CMX157, Scheme 12) is also designed to release tenofovir intracellularly (Hostetler, K., "Alkoxyalkyl Prodrugs of Acyclic Nucleoside Phosphonates Enhance Oral Antiviral Activity and Reduce Toxicity: Current State of the Art.", Antiviral Research, 82, A84-A98, 2009). Examples of other nucleoside phosphonate prodrugs used as antivirals can be found in the review by Pertusati, F., Serpi, M., McGuigan, C., "Medicinal Chemistry of Nucleoside Phosphonate Prodrugs for Antiviral Therapy.", Antiviral Chemistry and Chemotherapy, 22: 181-203 (2012).

The universally reducing environment of the cytoplasm can be used as a non-enzymatic release trigger which can be utilized to initiate an intracellular payload release. Attachment of a substituted cyclic disulfide, such as dithiothreitol to the phosphonate group in tenofovir will generate phosphonate ester with the potential of being reductively decoupled with concomitant intracellular release of tenofovir. According to this, the initial glutathione-mediated cyclic disulfide reduction of dithiothreitol in 13-1 will lead to a charge-dissipation driven cyclodeesterification to produce the mono-phosphonic acid 13-4, with concomitant formation of substituted thiirane 13-2. This will spontaneously self-quench (1,5-exo-tet ring closure) to yield the stable tetrahydrothiophene 13-3. Since the capacity of a leaving group to stabilize a charge is reflected in their acidity, one could expect that the ejection process will be more efficient with more acidic groups. Hence the phosphonate group of tenofovir, which is less acidic than the phosphate group present in a typical nucleoside monophosphate will release the payload slower. It will also require a secondary charge shielding group (RX, 13-1, Scheme 3) which will have to be cleaved after the reductively released cyclic disulfide monoester.

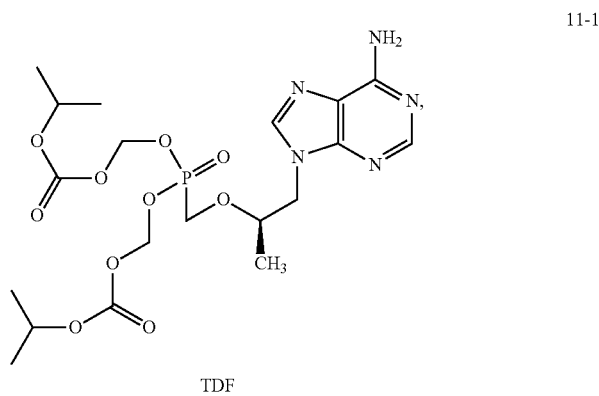

TDF

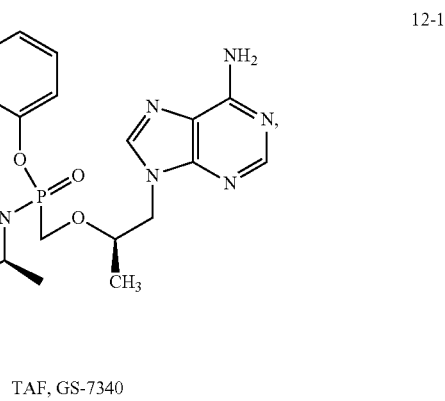

TAF, GS-7340

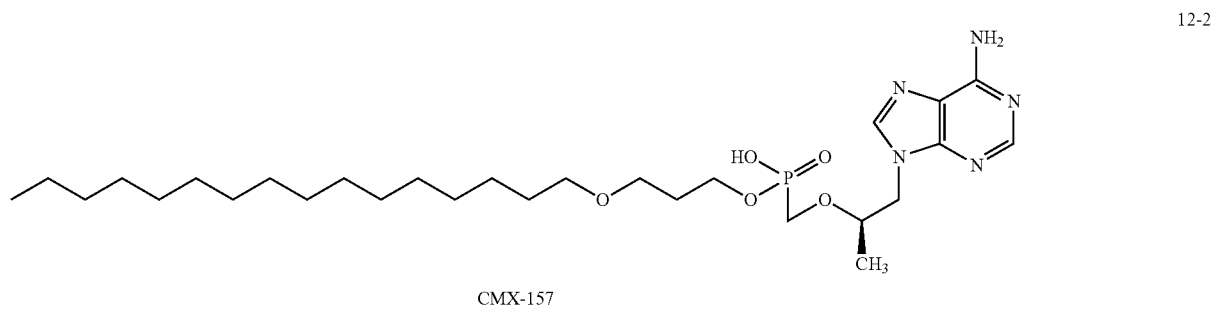

CMX-157

Scheme 13

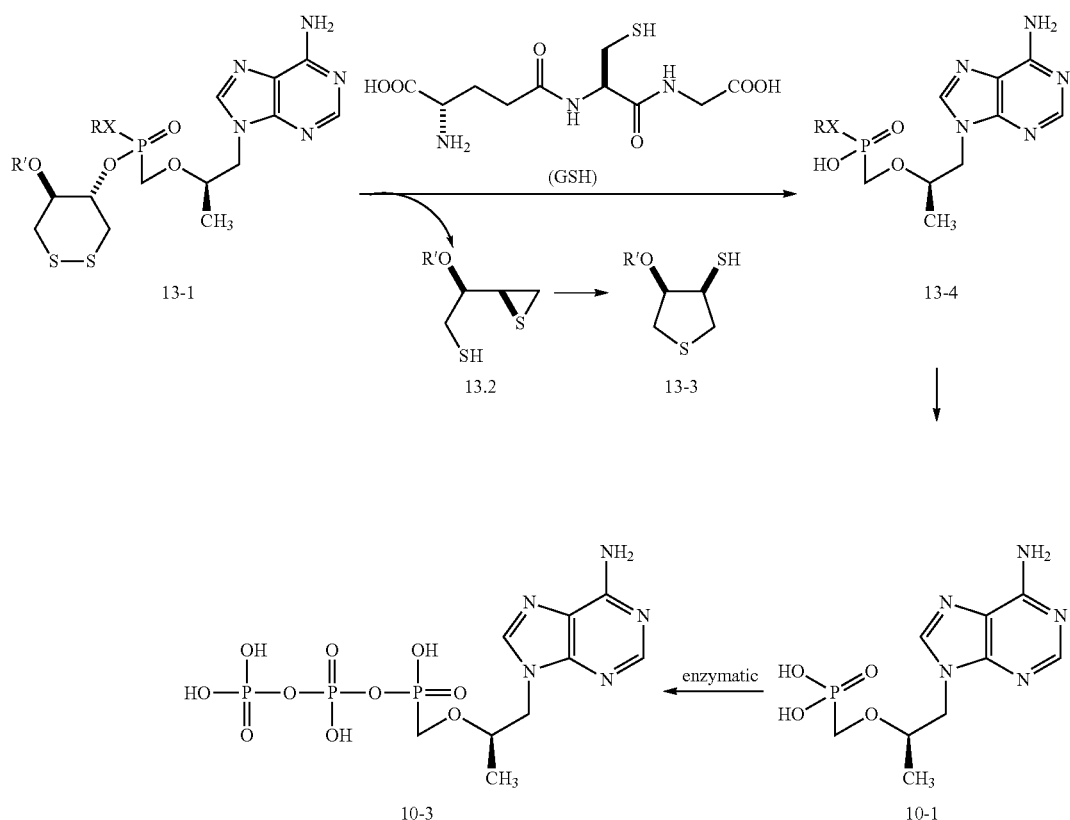

Particular examples are shown in Scheme 14. According to this, a phenyl ester 14-1 is expected to undergo a glutathione-mediated reductive ejection of the cyclic disulfide group, followed by a phosphatase-catalyzed phenyl ester hydrolysis. The second step is expected to take place after the reductive initiation, as the recognition of the phenyl ester by the enzyme (phosphatase) will ideally require the presence of the negative charge present at physiological pH on the phosphonate monoester 14-2. Similarly, a reductively initiated ejection of dithiothreitol from phosphonoamidate 14-3 is followed by an amidase mediated hydrolysis of 14-4. Phosphonoamidate 14-6 is designed to increase the nucleophilicity of the nitrogen in 4-6 after the initial ejection from 14-5, and a spontaneous follow-up hydrolysis (Caren L. Freel Meyers and Richard F. Borch: "Activation Mechanisms of Nucleoside Phosphoramidate Prodrugs.", *J. Med. Chem.* 2000, 43, 4319-4327).

Scheme 14

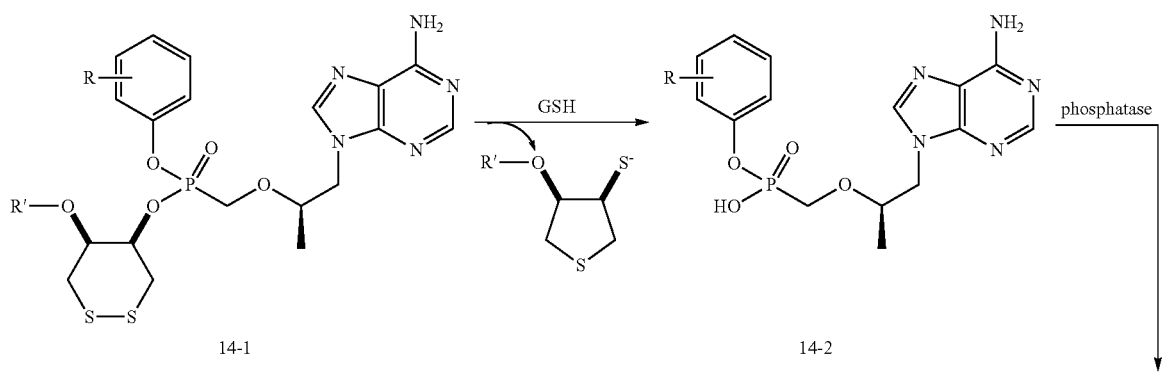

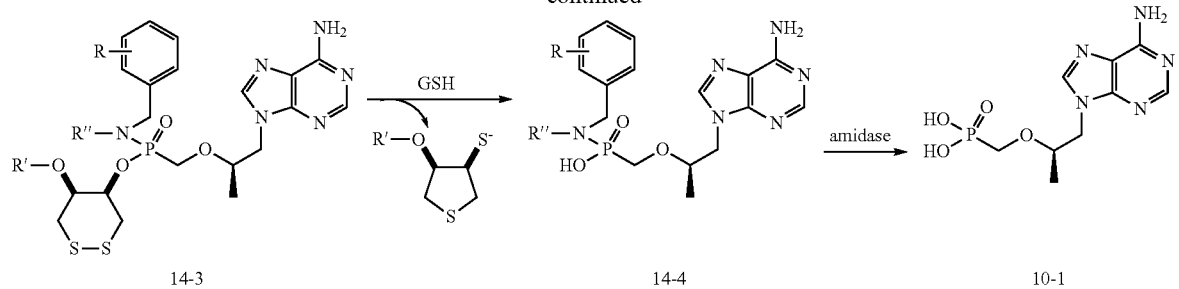

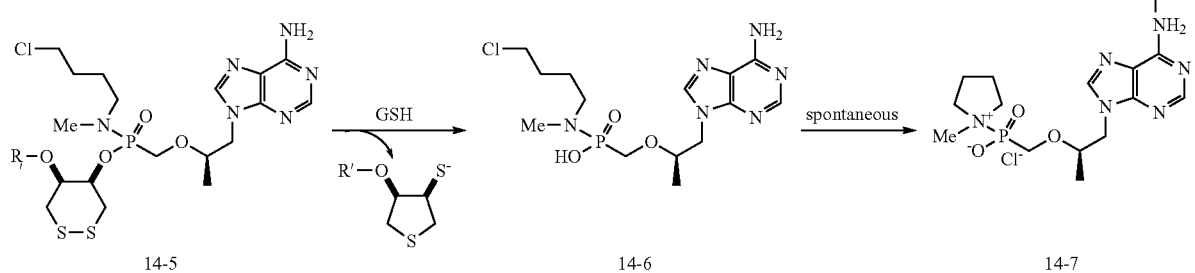

A representative example of preparation of phenyl ester 15-2 is described in Scheme 15. According to this, tenofovir 10-1 is esterified with phenol using DCC to produce the monoester 15-1, which was converted to the final diester 15-2 in a standard, PyBOP mediated esterification.

Scheme 15

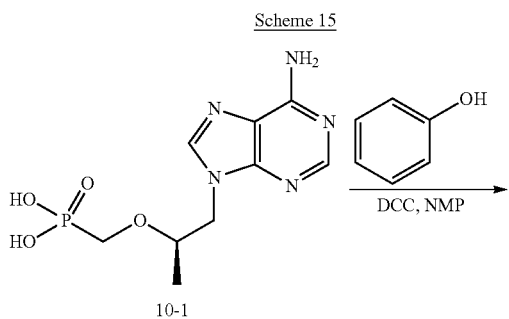

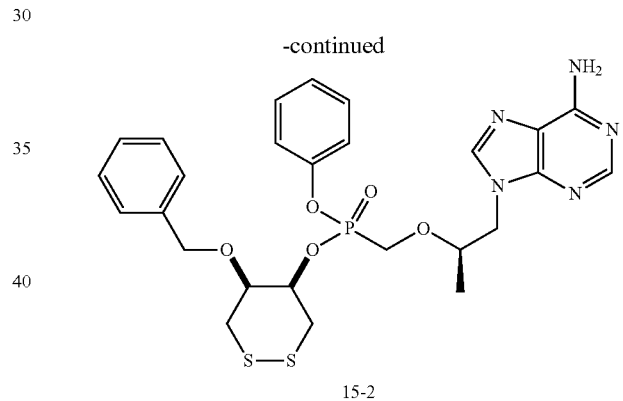

Figure 2:
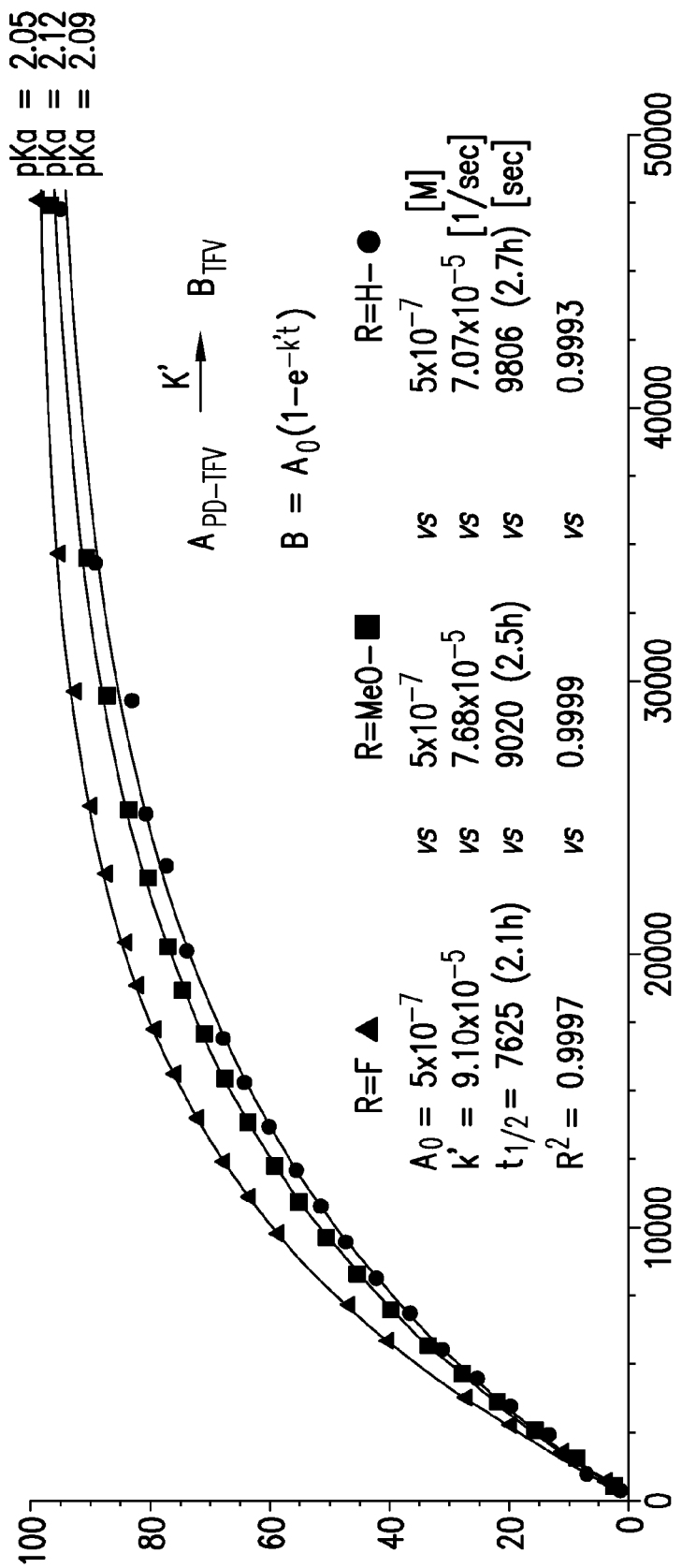
FIG. 2 shows the release of the mono-ester from compounds 16-1 and 16-2 when exposed to glutathione (50 mM) at pH of 7.3 and 40° C. as monitored by LCMS.

In certain embodiments, compounds 16-1 and 16-2 were exposed to glutathione (50 mM) at pH of 7.3 and 40° C., Scheme 16. The release of the mono-ester was monitored by LCMS and the data are summarized in FIG. 2.

Scheme 16

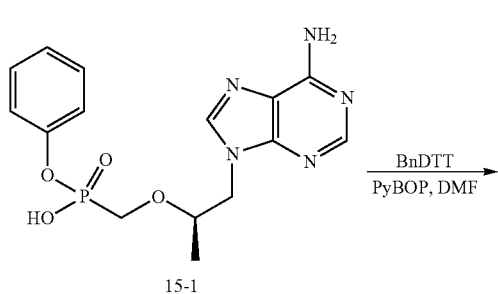

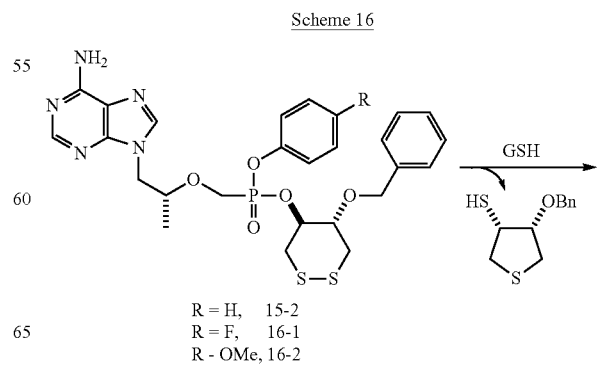

R = H, 15-2
R = F, 16-1
R = OMe, 16-2

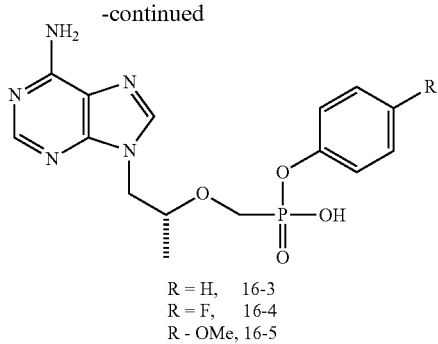

R = H, 16-3
R = F, 16-4
R = OMe, 16-5

EXAMPLES

Intermediates

All non-hydrolytic reactions, unless indicated otherwise were carried out in dry solvents purchased from Aldrich. HPLC analyses, except for the amidites, were performed at 60 C using an Agilent Zorbax Eclipse Plus C18, 2.1×50 mm, 1.8 micron column, at 0.8 mL/min flow rate, eluted with a gradient (5 to 95%) of acetonitrile and water with formic acid (0.1%) as a modifier. The amidites were analyzed using a Supelco Ascentis C18, 100×4.6 mm, 2.7 micron column and ammonium formate (3 mM) as a modifier, under otherwise identical conditions. UV traces were recorded at 220 nm and mass spectra were obtained using an Agilent Technologies 6140 Quadrupole LC/MS mass spectrometer in both positive and negative ion mode. Preparative purifications were performed by gradient chromatography on a Teledyne Isco CombiFlash Rf using pre-packed columns. NMR spectra were recorded on a Varian Unity 600, 500, or 400 spectrometers.

Intermediate 1

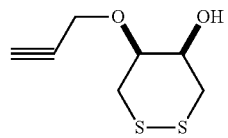

(4S/R,5R/S)-5-(Prop-2-yn-1-yloxy)-1,2-Dithian-4-ol

A 250 mL three neck flask, equipped with a condenser and averhead stirrer was charged with 5N KOH (100 mL, 500 mmol), followed by 80 mL of 2-methyl tetrahydrofurane, (4S/R, 5R/S)-1,2-dithian-4-ol (10 g, 65.7 mmol) and tetrabutylammonium hydrogen sulphate (4.46 g, 13.14 mmol). To this vigorously stirred mixture was added, via syringe pump, during a period of 12 h, a solution of propargyl bromide (9.38 g, 79 mmol) in 2-methyl tetrahydrofuran (20 mL). The stirring at ambient temperature was continued for additional 12 h. The organic layer was separated, and the aqueous was extracted with ethyl acetate (3×100 mL). The combined organic extracts were washed with water (1×100 mL), brine (1×100 mL) and dried over anhydrous sodium sulfate. Filtration and removal of the solvent in vacuo gave 10.4 g of crude product which was further purified by column chromatography (silica gel, 220 g, methanol-dichloromethane: 0% to 5% of methanol) to yield 5.25 g (42%) of the pure product as a colorless solid. $^1$H NMR (600 MHz, CD$_3$CN) δ: 4.27 (d, J=2.3 Hz, 2H), 3.42 (ddd, J=11.9, 8.5, 3.7 Hz, 1H), 3.23 (dd, J=13.6, 3.6 Hz, 1H), 3.07 (bd, J=13.0 Hz, 1H), 2.88 (dd, J=13.0, 10.3 Hz, 1H), 2.80 (dd, J=13.5, 10.2 Hz, 1H), 2.73 (t, J=2.5 Hz, 1H). $^{13}$C NMR (600 MHz, CD$_3$CN) δ: 81.5 (br), 80.3, 75.1, 73.4 (br), 57.2, 40.6 (br), 37.6 (br).

Intermediate 2

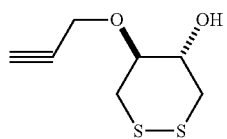

(4S/R, 5S/R)-5-(Prop-2-yn-1-yloxy)-1,2-Dithian-4-ol

This compound was prepared from dithioerhythritol disulfide and propargyl bromide using a procedure analogous to that described for Intermediate 1. $^1$H NMR (600 MHz, DMSO-D$_6$) δ: (bs, 1H), 4.25 (s, 2H), 3.7 (bm, 3H), 3.37 (t, J=2.40 Hz, 1H), 3.13 (m, 1H), 2.96 (dd, J=13.2, 8.1 Hz, 1H). $^{13}$C NMR (600 MHz, DMSO-D$_6$) δ: 81.23, 77.64, 75.92 (br), 70.43 (br), 65.48 (br), 56.33 (br.)

Intermediate 3

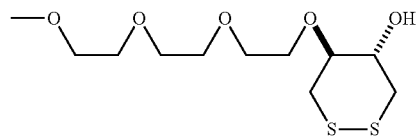 [SMILES: COCCOCCOCCO[C@@H]1CSSC[C@H]1O]

(4S/R,5R/S)-5-{2-[2-(2-Methoxyethoxyl)ethoxy]ethoxy}-1,2-dithian-4-ol

This compound was prepared from dithioerhythritol disulfide and 2-[2-(2-methoxyethoxyl)ethoxy]ethyl 4-methylbenzenesulfonate using a procedure analogous to that described for Intermediate 1. $^1$H NMR (600 MHz, CD$_3$CN) δ: 3.92 (s, 1H), 3.79 (ddd, J=11.3, 6.0, 2.7 Hz, 1H), 3.60 (m, 2H), 3.54 (m, 8H), 3.45 (m, 2H), 3.28 (s, 3H), 3.17 (dd, J=8.5, 4.8 Hz, 1H), 3.05 (dd, J=13.3, 3.6 Hz, 1H), 2.87 (dd, J=13.3, 10.4 Hz, 1H), 2.77 (dd, J=13.3, 10.3 Hz, 1H). $^{13}$C NMR (600 MHz, CD$_3$CN) δ: 83.5, 73.5, 71.8, 70.35, 70.33, 70.30, 70.25, 58.2, 69.3, 40.8, 37.9.

Intermediate 4

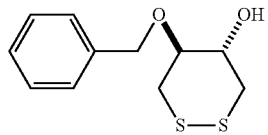 [SMILES: O[C@@H]1CSSC[C@H]1OCc1ccccc1]

(4S,5R)-5-(Benzyloxy)-1,2-dithian-4-ol and (4R,5S)-5-(Benzyloxy)-1,2-dithian-4-ol Trans-4,5-dihydroxy-1,2-dithiane (10 g, 65.7 mmol) and benzyl bromide (12.36 g, 72.3 mmol) were stirred at RT in 2-methyl-THF (100 ml). A solution of KOH (5 M in water) (100 ml, 500 mmol) was added, followed by the addition of tertrabutylammonium hydrogen sulfate (5.58 g, 16.4 mmol). The reaction mixture was stirred vigorously for 18 h. The resulting mixture was partitioned between ethyl acetate (200 mL) and water (200 mL). The aqueous layer was washed with ethyl acetate (3×50 mL). The combined organice phase was dried ($Na_2SO_4$) and concentrated under reduced pressure. The residue was purified by flash chromatography using 10% ethyl acetate in hexane to yield 9.0 g (37.1 mmol, 56%) of the racemic mixture of the product. It was further purified by SFC-HPLC (Diacel Chiralpak AS, 30×250 mm, 30% MeOH/$CO_2$, 70 mL/min) to yield 4.3 g of (4R,5R)-5-(benzyloxy)-1,2-dithian-4-ol (17.7 mmol, 27.0%) and 4.2 g of (4S,5S)-5-(benzyloxy)-1,2-dithian-4-ol (17.3 mmol, 26%). For (4R,5R)-5-(benzyloxy)-1,2-dithian-4-ol, LCMS: for $C_{11}H_{11}O_2S_2$, calculated 242.0. found 243.0 $[M+H]^+$. $^1$H NMR (500 MHz, $CD_3CN$) δ: 7.35 (m, 5H), 4.68 (d, J=11.5 Hz, 1H), 4.59, (d, J=11.6 Hz, 1H), 3.63 (m, 1H), 3.52 (d, J=3.6 Hz, 1H), 3.39 (m, 1H), 3.27 (dd, J=13.5, 3.5 Hz, 1H), 3.10 (dd, J=13.4, 2.9 Hz, 1H), 2.86 (m, 2H). $^{13}$C NMR (500 MHz, $CD_3CN$) δ: 138.66, 128.34, 127.97, 127.66, 71.30. For (4S,5S)-5-(benzyloxy)-1,2-dithian-4-ol, LCMS: for $C_{11}H_{11}O_2S_2$, calculated 242.0. found 243.0 $[M+H]^+$. $^1$H NMR (500 MHz, $CD_3CN$) δ: 7.36 (m, 5H), 4.71 (d, J=11.7 Hz, 1H), 4.66, (d, J=11.7 Hz, 1H), 3.66 (m, 1H), 3.55 (d, J=3.6 Hz, 1H), 3.42 (m, 1H), 3.30 (dd, J=13.5, 3.6 Hz, 1H), 3.13 (dd, J=13.3, 2.9 Hz, 1H), 2.89 (m, 2H). $^{13}$C NMR (500 MHz, $CD_3CN$) δ: 138.66, 128.34, 127.97, 127.66, 71.30.

Intermediate 5

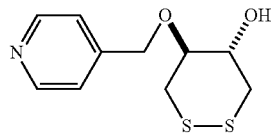 [SMILES: O[C@@H]1CSSC[C@H]1OCc1ccncc1]

(4R/S,5R/S)-5-(pyridin-4-ylmethoxy)-1,2-dithian-4-ol was synthesized using the same procedure described in intermediate 2. LCMS: for $C_{10}H_{13}NO_2S_2$ calculated 243.0. found 244.0 $[M+H]^+$.

Intermediate 6

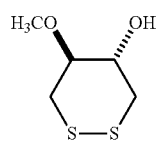

(4S/R,5S/R)-5-Methoxy-1,2-dithian-4-ol was synthesized using dimethyl sulfate as an alkylating agent in 40% yield following the procedure described for Intermediate 2. The final product is a mixture of two enantiomer. Chemical Formula: $C_5H_{10}O_2S_2$. Exact Mass: 166.01. No UV and MS detection of the LCMS analysis. $^1$H NMR (500 MHz, $CD_3CN$) δ: 3.66 (m, 2H), 3.50 (s, 3H), 3.36 (dd, J=13.4 Hz, 3.6 Hz, 1H), 3.25 (m, 1H), 3.17 (dd, J=13.3 Hz, 3.3 Hz, 1H), 2.98 (dd, 13.4 Hz, 10.1 Hz), 2.86 (dd, 13.3 Hz, 10.1 Hz, 1H). $^{13}$C NMR (500 MHz, $CD_3CN$) δ: 83.44, 72.51, 56.66, 40.15, 36.62.

Intermediate 7

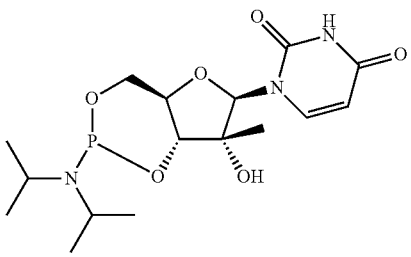

1-((4aR,6R,7R,7aR)-2-(Diisopropylamino)-7-hydroxy-7-methyltetrahydro-4H-furo[3,2-d][1,3,2]dioxaphosphinin-6-yl)pyrimidine-2,4(1H,3H)-dione Under the protection of $N_2$, 1-((2R,3R,4R,5R)-3,4-dihydroxy-5-(hydroxymethyl)-3-methyltetrahydrofuran-2-yl)pyrimidine-2,4(1H,3H)-dione (260 mg, 1.01 mmol) and N,N-diisopropylethylamine (390 mg, 3.02 mmol) were dissolved into 10 mL anhydrous dichloromethane with 3 Å molecular seives (2 g). After the mixture was cooled to 0° C., bis(diisopropylamino)chlorophosphine (322 mg, 1.21 mmol) was added. The reaction mixture was stirred at 0° C. for 30 min and was slowly warmed up to RT and stirred for 3 h. DMAP (61.5 mg, 0.50 mmol) was added to facilitate the cyclization. The reaction was stirred at RT for 16 h. The solid was removed by filtration. The filtrate was concentrated under reduced pressure, and the residue was purified by flash chromatography using 25% acetone in hexane to obtain 163 mg (0.42 mmol, 42%) of the pure product. LCMS: for $C_{16}H_{26}N_3O_6P$ calculated 387.2. found 388.0 $[M+H]^+$. $^1$H NMR (500 MHz, $CD_3CN$) δ: 9.29 (s, br, 1H), 7.40 (m, 1H), 5.94 (s, 1H), 5.68 (dd, J=4.0, 4.0 Hz, 1H), 4.42 (m, 1H), 4.17 (dd, J=10.0, 10.0 Hz, 1H), 3.88 (m, 1H), 3.75 (m, 2H), 3.56 (d, J=9.1 Hz, 1H), 3.47 (s, br, 1H), 1.22 (m, 12H), 1.17 (s, 3H). $^{13}$C NMR (500 MHz, $CD_3CN$) δ: 140.16, 102.29, 93.10, 66.61, 44.44, 44.34, 24.20, 24.15, 19.71, −5.11. $^{31}$P NMR (500 MHz, $CD_3CN$) δ: 150.43.

Intermediate 8

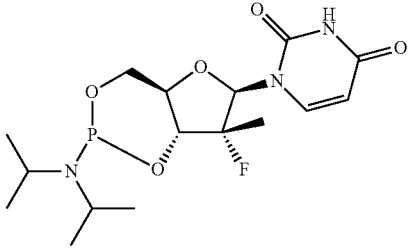

1-((4aR,6R,7R,7aR)-2-(diisopropylamino)-7-fluoro-7-methyltetrahydro-4H-furo[3,2-d][1,3,2]dioxaphosphinin-6- yl)pyrimidine-2,4(1H,3H)-dione was synthesized using the procedure described for intermediate 1. LCMS: for $C_{16}H_{25}FN_3O_5P$ calculated 389.2. found 390.0 [M+H]+. $^{31}P$ NMR (500 MHz, $CD_3OD$) δ: 150.42.

Intermediate 9

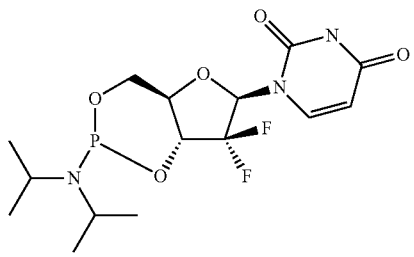

4-amino-1-((4aR,6R,7aR)-2-(diisopropylamino)-7,7-difluorotetrahydro-4H-furo[3,2-d][1,3,2]dioxaphosphinin-6-yl)pyrimidin-2(1H)-one was synthesized using the procedure described for intermediate 1. LCMS: for $C_{15}H_{23}F_2N_4O_4P$ calculated 392.1. found 393.0 [M+H]+. $^{31}P$ NMR (500 MHz, $CD_3OD$) δ: 152.40.

Example 1

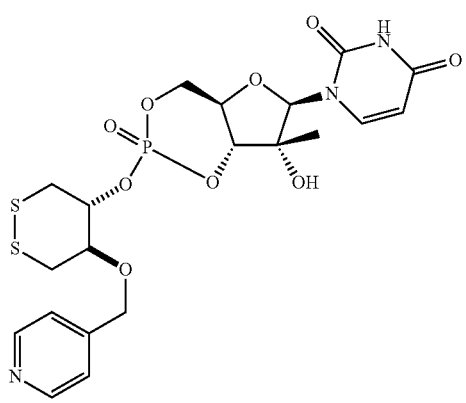

1-((4aR,6R,7R,7aR)-2-(((4R/S,5R/S)-5-(Benzyloxy)-1,2-dithian-4-yl)oxy)-7-hydroxy-7-methyl-2-oxidotetrahydro-4H-furo[3,2-d][1,3,2]dioxaphosphinin-6-yl)pyrimidine-2,4-(1H,3H)-dione To a solution of 1-((4aR,6R,7R,7aR)-2-(diisopropylamino)-7-hydroxy-7-methyltetrahydro-4H-furo[3,2-d][1,3,2]dioxaphosphinin-6-yl)pyrimidine-2,4(1H,3H)-dione (115 mg, 0.30 mmol) in dichloromethane (10 mL) stirring at RT was added 5-(pyridin-4-ylmethoxy)-1,2-dithian-4-ol (108 mg, 0.45 mmol) and 5-(ethylthio)-1H-tetrazole (19.3 mg, 0.15 mmol). The reaction was stirred at RT for 4 h, when tert-butylhydroperoxide (40.1 mg, 0.45 mmol) was added. The reaction was stirred at RT for another 30 min. Solvent was removed under reduced pressure, the residue was purified by flash chromatography using 10% MeOH in dichloromethane to obtain 17 mg (0.03 mmol, 11%) of the pure product. LCMS: for $C_{20}H_{24}N_3O_9PS_2$ calculated 545.1. found 546.0 [M+H]+. $^{31}P$ NMR (500 MHz, $CD_3OD$) δ: −1.49, −4.63, −5.00, −6.91.

Example 2

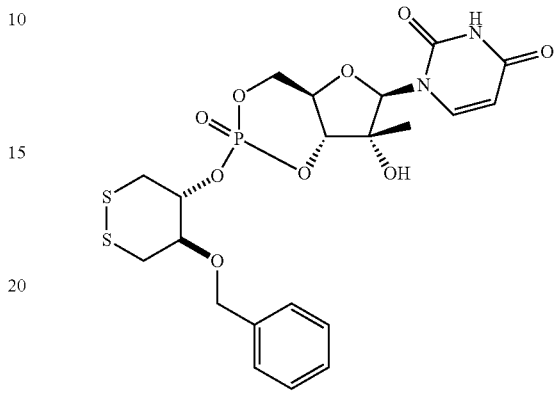

1-((4aR,6R,7R,7aR)-2-(((4R/S,5R/S)-5-(benzyloxy)-1,2-dithian-4-yl)oxy)-7-hydroxy-7-methyl-2-oxidotetrahydro-4H-furo[3,2-d][1,3,2]dioxaphosphinin-6-yl)pyrimidine-2,4 (1H,3H)-dione was synthesized from Intermediates 4 and 7 following the procedure described in Example 1. LCMS: for $C_{21}H_{25}N_2O_9PS_2$ calculated 544.1. found 562.0 [M+H$_2$O]. $^{31}P$ NMR (500 MHz, $CD_3OD$) δ: −4.10, −4.49, −6.44, −6.62.

Example 3

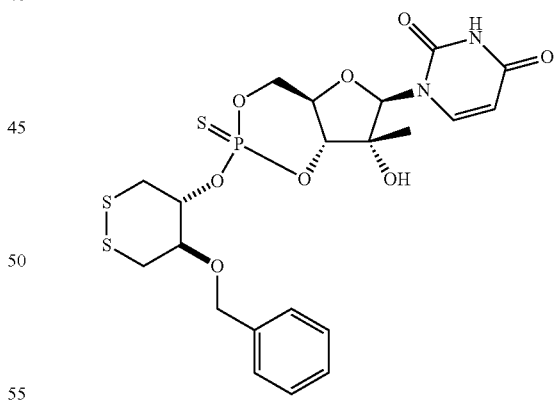

1-((4aR,6R,7R,7aR)-2-(((4R/S,5R/S)-5-(Benzyloxy)-1,2-dithian-4-yl)oxy)-7-hydroxy-7-methyl-2-sulfidotetrahydro-4H-furo[3,2-d][1,3,2]dioxaphosphinin-6-yl)pyrimidine-2,4 (1H,3H)-dione was synthesized from Intermediates 4 and 7 following a procedure analogous to that described in Example 1, except the oxidation was performed with diphenylacetyldisulfide instead of ther-butyl hydroperoxide. LCMS: for $C_{21}H_{25}N_2O_8PS_3$ calculated 560.0. found 583.0 [M+Na]+. $^{31}P$ NMR (500 MHz, $CD_3OD$) δ: 65.79, 62.12, 61.95.

Example 4

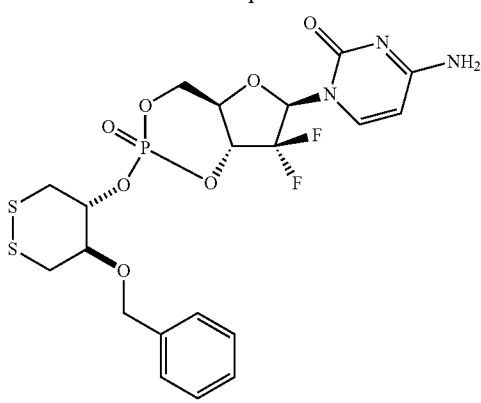

4-amino-1-((4aR,6R,7aR)-2-(((4R/S,5R/S)-5-(benzyloxy)-1,2-dithian-4-yl)oxy)-7,7-difluoro-2-oxidotetrahydro-4H-furo[3,2-d][1,3,2]dioxaphosphinin-6-yl)pyrimidin-2(1H)-one was synthesized from Intermediates 4 and 9 following the procedure described in Example 1. LCMS: for $C_{20}H_{22}F_2N_3O_7PS_2$ calculated 549.1. found 550 [M+H]$^+$. $^{31}$P NMR (500 MHz, CD$_3$OD) δ: −5.14, −5.34, −7.76, −8.02.

Example 5

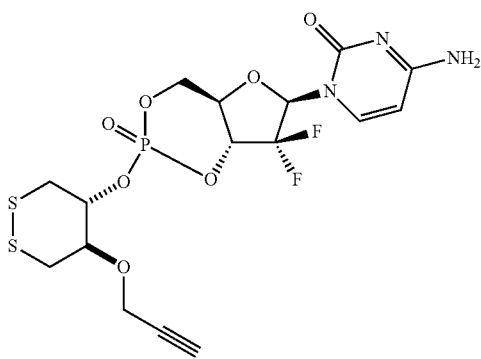

4-Amino-1-((4aR,6R,7aR)-7,7-difluoro-2-oxido-2-(((4R/S,5R/S)-5-(prop-2-yn-1-yloxy)-1,2-dithian-4-yl)oxy)tetrahydro-4H-furo[3,2-d][1,3,2]dioxaphosphinin-6-yl)pyrimidin-2(1H)-one was synthesized from Intermediates 1 and 9 following the procedure described in Example 1. LCMS: for $C_{16}H_{18}F_2N_3O_7PS_2$ calculated 497.0. found 498.0 [M+H]$^+$. $^{31}$P NMR (500 MHz, CD$_3$OD) δ: −5.33, −5.68, −7.91.

Example 6

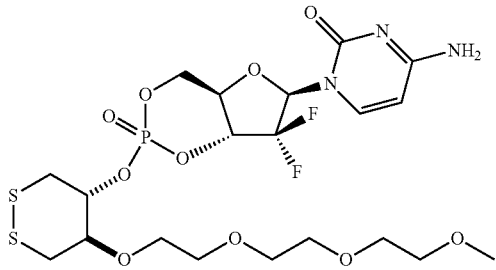

4-Amino-1-((4aR,6R,7aR)-7,7-difluoro-2-(((4R/S,5R/S)-5-(2-(2-(2-methoxyethoxy)ethoxy)ethoxy)-1,2-dithian-4-yl)oxy)-2-oxidotetrahydro-4H-furo[3,2-d][1,3,2]dioxaphosphinin-6-yl)pyrimidin-2(1H)-one was synthesized from Intermediates 3 and 9 following the procedure described in Example 1. LCMS: for $C_{20}H_{30}F_2N_3O_{10}PS_2$ calculated 605.1. found 606.1 [M+H]$^+$. $^{31}$P NMR (500 MHz, CD$_3$OD) δ: −5.01, −5.42, −7.71, −7.93.

Example 7

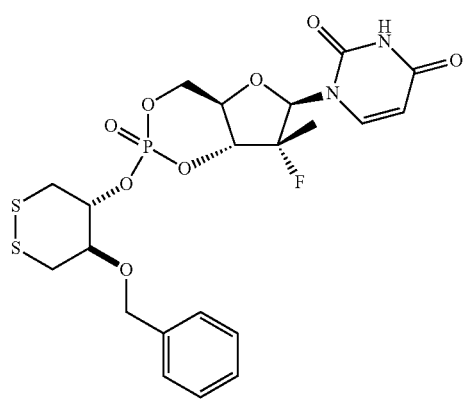

1-((4aR,6R,7R,7aR)-2-(((4R/S,5R/S)-5-(Benzyloxy)-1,2-dithian-4-yl)oxy)-7-fluoro-7-methyl-2-oxidotetrahydro-4H-furo[3,2-d][1,3,2]dioxaphosphinin-6-yl)pyrimidine-2,4(1H,3H)-dione was synthesized from Intermediates 4 and 8 following the procedure described in Example 1. LCMS: for $C_{21}H_{24}FN_2O_8PS_2$ calculated 546.1. found 545.0 [M−H]$^−$. $^{31}$P NMR (500 MHz, CD$_3$OD) δ: −5.55, −5.67, −8.09, −8.36.

Example 8

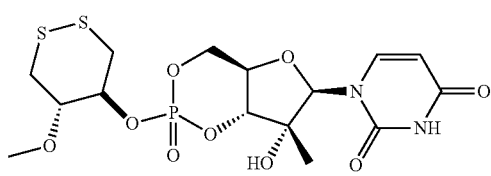

1-((4aR,6R,7R,7aR)-7-Hydroxy-2-(((4S/R,5S/R)-5-methoxy-1,2-dithian-4-yl)oxy)-7-methyl-2-oxidotetrahydro-4H-furo[3,2-d][1,3,2]dioxaphosphinin-6-yl)pyrimidine-2,4(1H,3H)-dione was synthesized from intermediates 6 and 7 using the procedure described in Example 1. The final product was a mixture of the four diastereomers. LCMS: for $C_{15}H_{21}N_2O_9PS_2$ calculated 468.0. found 491.0 [M+Na]$^+$. $^{31}$P NMR (500 MHz, CD$_3$CN) δ: −5.19, −5.68, −7.74, −7.67.

Example 9

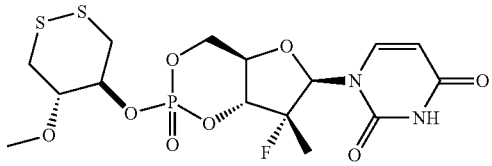

1-((4aR,6R,7R,7aR)-7-Fluoro-2-(((4S/R,5S/R)-5-methoxy-1,2-dithian-4-yl)oxy)-7-methyl-2-oxidotetrahydro-4H-furo[3,2-d][1,3,2]dioxaphosphinin-6-yl)pyrimidine-2,4(1H,3H)-dione was synthesized from intermediates 6 and 8 using the procedure described in Example 1. The final product was a mixture of the four diastereomers. LCMS: for $C_{15}H_{20}FN_2O_8PS_2$ calculated 470. found 493.0 [M+Na]+. $^{31}P$ NMR (500 MHz, $CD_3CN$) δ: −5.54, −5.83, −8.17, −8.29.

Example 10

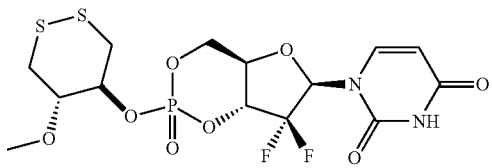

1-((4aR,6R,7aR)-7,7-Difluoro-2-(((4S,5S)-5-methoxy-1,2-dithian-4-yl)oxy)-2-oxidotetrahydro-4H-furo[3,2-d][1,3,2]dioxaphosphinin-6-yl)pyrimidine-2,4(1H,3H)-dione was synthesized from intermediates 6 and 9 using the procedure described in Example 1. The final product was a mixture of the four diastereomers. LCMS: for $C_{14}H_{17}F_2N_2O_8PS_2$ calculated 474. found 475 [M+H]+. $^{31}P$ NMR (500 MHz, $CD_3CN$) δ: −5.81, −6.18, −8.21.

Example 11

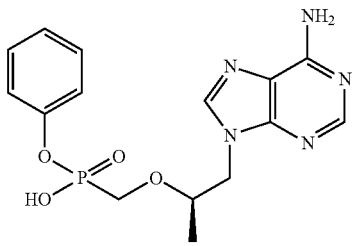 [SMILES: C[C@H](Cn1cnc2c(N)ncnc21)OCP(=O)(O)Oc1ccccc1]

Phenyl hydrogen ((((R)-1-(6-amino-9H-purin-9-yl)propan-2-yl)oxy)methyl)phosphonate To a 100 ml 3 neck flask was charged with Tenofovir (1.25 g, 4.35 mmol), phenol (0.819 g, 8.70 mmol) and NMP (11 mL). The mixture was heated to 85° C. and TEA (0.789 mL, 5.66 mmol) was added. A solution of DCC (1.437 g, 6.96 mmol) in NMP (2.4 mL) was then added slowly at 100° C. Heating is continued for 16 h. The reaction is cooled to 45° C., diluted with water (10 mL) and cooled to 25° C. Solids were removed by filtration and rinsed with water (5 mL). The combined filtrate and rinse was concentrated to a tan slurry under reduced pressure. It was diluted with water. The resulting tan solution was purified by LC-MS (5-65% ACN in Water), yielding 0329531-0138 (350 mg, 0.963 mmol, 22.14% yield) as a white solid. LCMS: for $C_{15}H_{18}N_5O_4P$ calculated 363.11. found 364.20 [M+H]+. $^{31}P$ NMR (500 MHz, $CD_3CN$) δ: 15.09.

Example 12

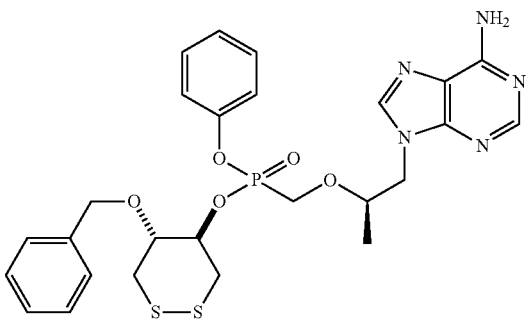

(4R,5R)-5-(Benzyloxy)-1,2-dithian-4-yl phenyl((((R)-1-(6-amino-9H-purin-9-yl)propan-2-yl)oxy)methyl)phosphonate. To a mixture of the monoPhenyl ester, preparation of which was described in example 12 (120 mg, 0.330 mmol), (4R,5R)-5-(benzyloxy)-1,2-dithian-4-ol (120 mg, 0.495 mmol), PyBOP (258 mg, 0.495 mmol) and 1 g molecular sieves in DMF (2 ml) was added DIEA (0.231 ml, 1.321 mmol). After stirred at RT for 18 h, the solid was filtered off. The filtrated was concentrated in vacuo to give an orange gel. The residue was dissolved in 1:1 mixture of ACN/waster and purified by LC-MS (10-70% ACN in water) to give 0329531-0142 (60 mg, 0.102 mmol, 30.9% yield) as a white solid. LCMS: for $C_{26}H_{30}N_5O_5PS_2$ calculated 587.14. found 588.00 [M+H]+. $^{31}P$ NMR (500 MHz, $CD_3CN$) δ: 18.88.

Biology

The therapeutic potential of the prodrugs disclosed herein was demonstrated using nucleosides active against hepatitis virus C (HCV). Table 3 and Table 4 summarize the measured activities of these prodrugs as assessed in a subgenomic replicon assay (RHEPTAQ), against genotypes 1a, 1b and 2a.

TABLE 3

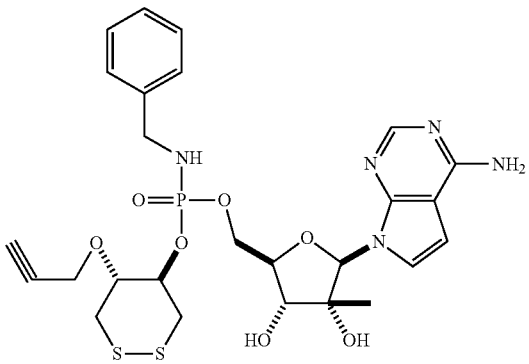

(RHEPTAQ, 4 isomers)
$EC_{50/90}(1a) = 12.8/25.5$ mM
$EC_{50/90}(1b) = 8.5/17.7$ mM
$EC_{50/90}(2a) = 1.9/7.9$ mM TABLE 3-continued

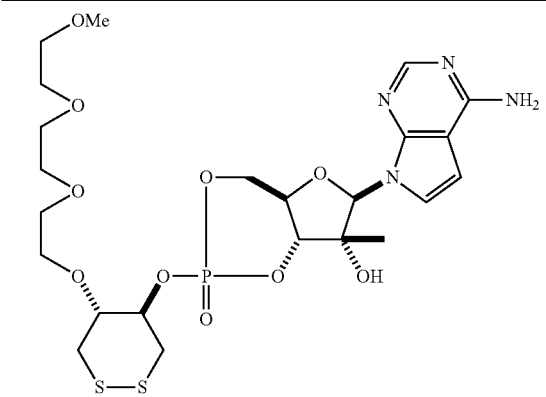

(RHEPTAQ, 4 isomeres))
EC$_{50/90}$(1a) = 1000/3300 nM
EC$_{50/90}$(1b) = 183/448 nM
EC$_{50/90}$(2a) = 249/896 nM

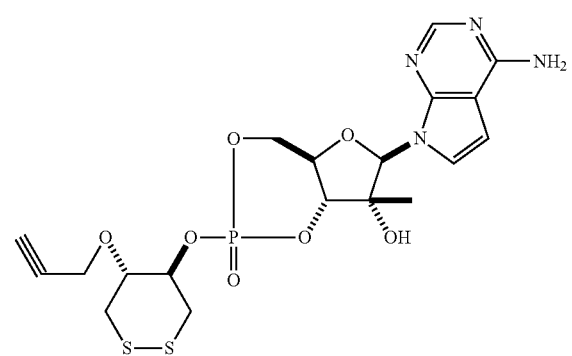

(RHEPTAQ, 4 isomeres)
EC$_{50/90}$(1a) = 159/991 nM
EC$_{50/90}$(1b) = 78/318 nM
EC$_{50/90}$(2a) = 135/115 nM

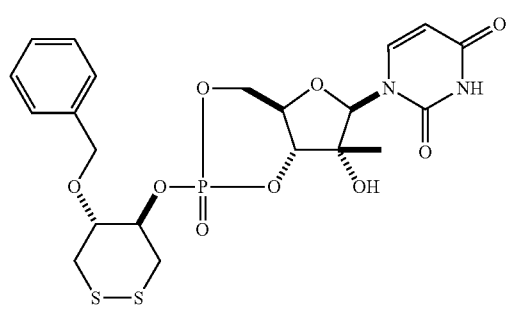

(RHEPTAQ)
isomer 1
EC$_{50/90}$(1a) = 70/233 nM
EC$_{50/90}$(1b) = 110/383 nM
EC$_{50/90}$(2a) = 90/442 nM
isomer 2
EC$_{50/90}$(1a) = 50/154 nM
EC$_{50/90}$(1b) = 37/245 nM
EC$_{50/90}$(2a) = 44/244 nM
isomer 3 and 4
EC$_{50/90}$(1a) = 305/782 nM
EC$_{50/90}$(1b) = 362/783 nM
EC$_{50/90}$(2a) = 315/1071 nM TABLE 3-continued

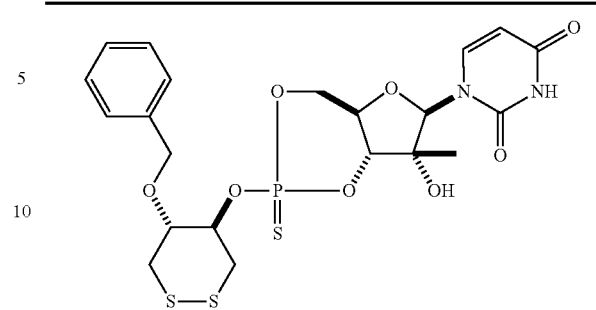

(RHEPTAQ)
isomer 1 and 2
EC$_{50/90}$(1a) = 4/8 μM
isomer 3 and 4
EC$_{50/90}$(1a) = 45/32 μM

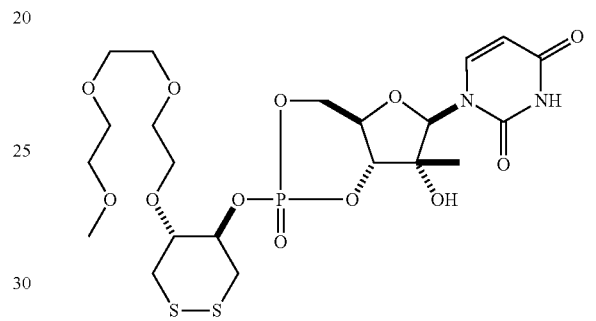

(RHEPTAQ)
isomer 1 and 2
EC$_{50/90}$(1a) = 4/9 μM
EC$_{50/90}$(1b) = 2/8 μM
EC$_{50/90}$(2a) = 6/21 μM
isomer 3 and 4
EC$_{50/90}$(1a) = 7/16 μM
EC$_{50/90}$(1b) = 4/12 μM
EC$_{50/90}$(2a) = 14/37 μM

TABLE 4

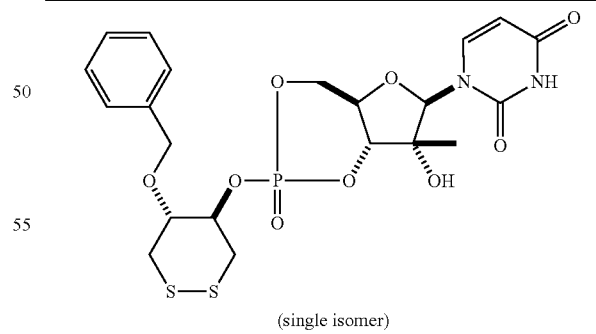

(single isomer)

Replicon:

EC$_{50}$ (1a) = 70 nM
EC$_{50}$ (1b) = 110 nM
EC$_{50}$ (2a) = 90 nM
Tox:

EdU/CellCount: CC$_{50}$ = 4.1/8.5 μM

TABLE 4-continued

In vitro NTP (Hepatocytes):

Hep-CDP time course (10 μM closed)
AUC(0-48 h): 49069 (μM · h)
$C_{max}$: 1410 (μM)
In vivo NTP Rat
Liver NTP: 25 mpk, p.o. (1 h/4 h): 7 μM/12 μM

[Chemical structure]

(single isomer)

Replicon:

$EC_{50}$ (1a) = 92 nM
$EC_{50}$ (1b) = 107 nM
$EC_{50}$ (1c) = 101 nM

Tox:

EdU/CellCount: $CC_{50}$ = 30/85 μM

In vitro NTP (Hepatocytes):

Hep-CDP time course (10 μM dosed)
AUC(0-48 h): 14587 (μM · h)
$C_{max}$: 395 (μM)
In vivo NTP Rat
Liver NTP: 25 mpk, p.o. (1 h/4 h): 20 μM/49 μM Assessing Antiviral Potency in a Multiple Round HIV-1 Infection Assay The antiviral activity of the tenofovir prodrugs was assessed in a Viking assay performed as follows. HIV-1 replication was monitored using MT4-gag-GFP clone D3 (hereafter designate MT4-GFP), which are MT-4 cells modified to harbor a GFP reporter gene, the expression of which is dependent on the HIV-1 expressed proteins tat and rev. Productive infection of an MT4-GFP cell with HIV-1 results in GFP expression approximately 24 h post-infection.

MT4-GFP cells were maintained at 37° C./5% $CO_2$/90% relative humidity in RPMI 1640 supplemented with 10% fetal bovine serum, 100 U/ml penicillin/streptomycin, and 400 μg/ml G418 to maintain the reporter gene. For infections, MT4-GFP cells were placed in the same medium lacking G418 and infected overnight with H9IIIB virus at an approximate multiplicity of infection of 0.01 in the same incubation conditions. Cells were then washed and resuspended in either RPMI 1640 containing 10% normal human serum at $1.6 \times 10^5$ cells/mL (10% NHS conditions) or in 100% normal human serum at $2 \times 10^5$ cells/mL (100% NHS conditions). Compound plates were prepared by dispensing compounds dissolved in DMSO into wells of 384 well poly D lysine-coated plates (0.2 μl/well) using an ECHO acoustic dispenser. Each compound was tested in a 10 point serial 3-fold dilution (typical final concentrations: 4.2 μM-0.21 nM). Controls included no inhibitor (DMSO only) and a combination of three antiviral agents (efavirenz, indinavir, and the integrase strand transfer inhibitor N1-ethyl-N1-((7S, 10R)-2-((4-fluorobenzyl)-carbamoyl)-3-hydroxy-7-methoxy-4-oxo-4,6,7,8,9,10-hexahydropyrimido-[1,2-a]azepin-10-yl)-N2,N2-dimethyloxalamide at final concentrations of 4 μM each). Cells were added (50 μL/well) to compound plates and the infected cells were maintained at 37° C./5% $CO_2$/90% relative humidity.

Infected cells were quantified at two time points, ~48 h and ~72 h post-infection, by counting the number of green cells in each well using an Acumen eX3 scanner. The increase in the number of green cells over ~24 h period gives the reproductive ratio, $R_0$, which is typically 5-15 and has been shown experimentally to be in logarithmic phase (data not shown) Inhibition of $R_0$ is calculated for each well, and $IC_{50}$s determined by non-linear 4-parameter curve fitting. Data are summarized in Table 5.

TABLE 5

| Entry | Structure | Viking IP (nM) | CTG $LD_{50}$ (nM) |
|---|---|---|---|
| 1 | [Chemical structure] | 1265 | >8403 |

TABLE 5-continued

| Entry | Structure | Viking IP (nM) | CTG LD$_{50}$ (nM) |
|---|---|---|---|
| 2 | 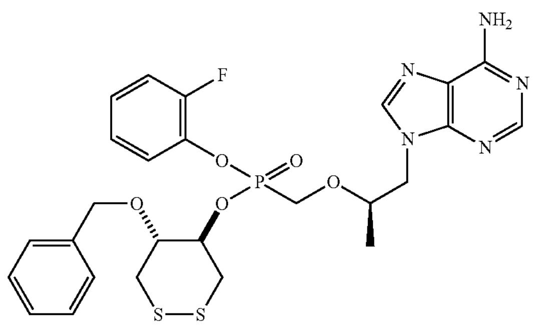 | 605 | >8403 |
| 3 | 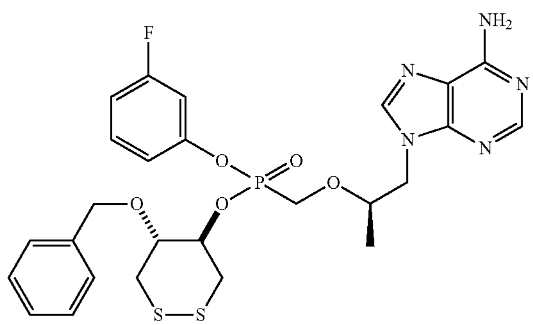 | 620 | >42020 |
| 4 | 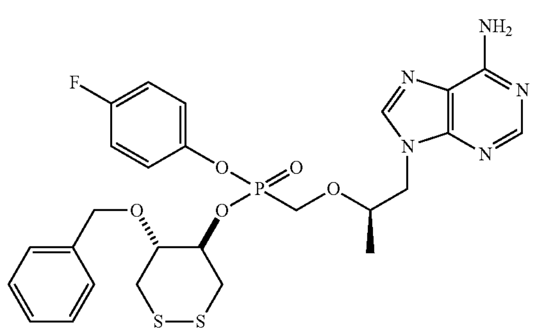 | 2000 | >8403 |
| 5 | 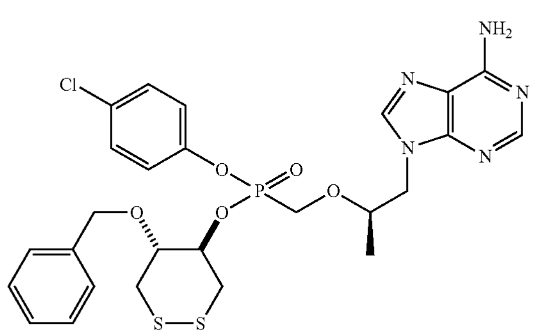 | 1593[a] | >8403 |

TABLE 5-continued

| Entry | Structure | Viking IP (nM) | CTG LD$_{50}$ (nM) |
|---|---|---|---|
| 6 | 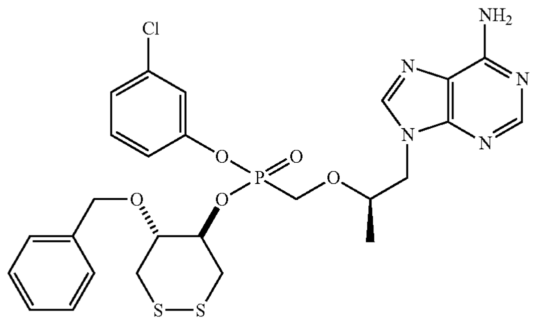 | 1880[a] | >8403 |
| 7 | 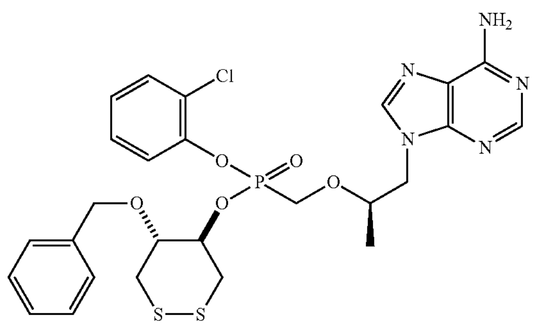 | 1590[a] | >8403 |
| 8 | 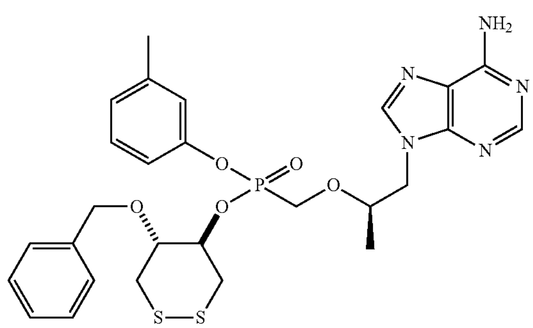 | 1118 | >42020 |
| 9 | 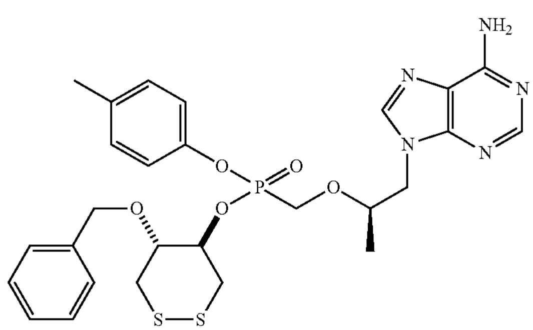 | 1640 | >42020 |

TABLE 5-continued

| Entry | Structure | Viking IP (nM) | CTG LD$_{50}$ (nM) |
|---|---|---|---|
| 10 | 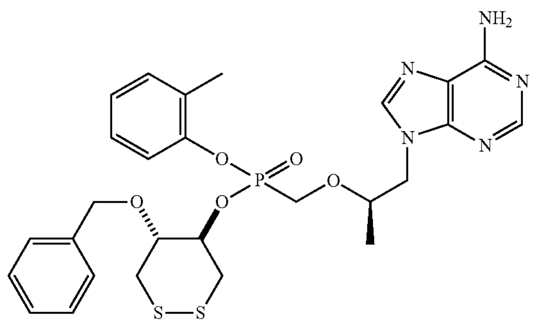 | 2919[a] | >42020 |
| 11 | 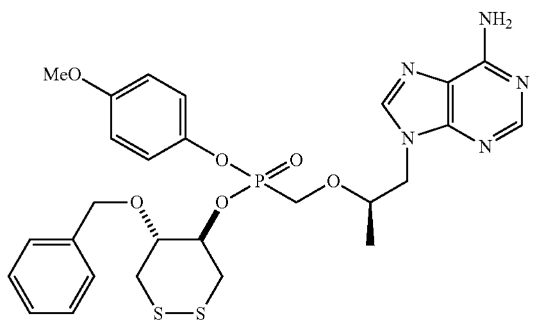 | 2919[a] | >42020 |
| 12 | 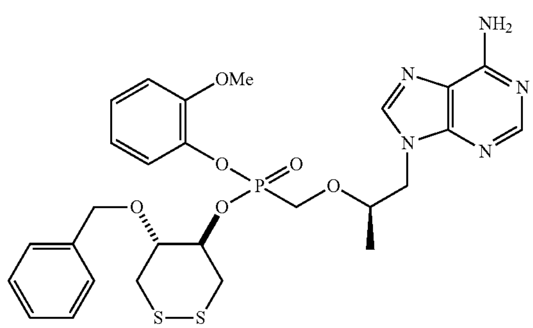 | 1551[a] | >39780 |
| 13 | 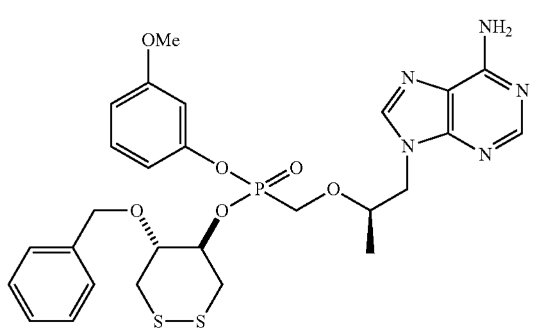 | 1812 | >8403 |

TABLE 5-continued

| Entry | Structure | Viking IP (nM) | CTG LD$_{50}$ (nM) |
|---|---|---|---|
| 14 | 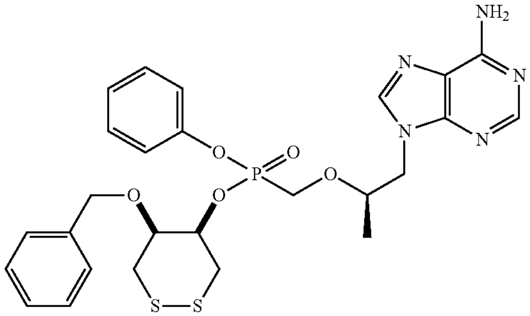 | 1265 | >8403 |
| 15 | 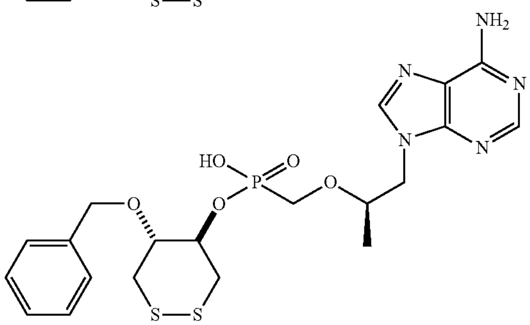 | >8403 | >8403 |
| 16 | 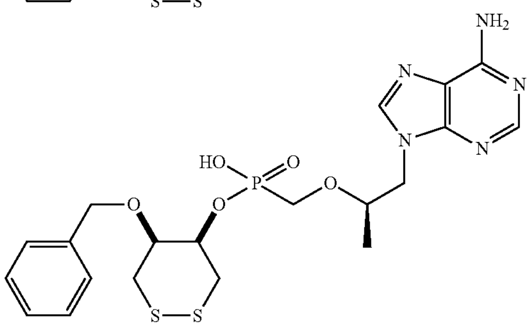 | >8403 | >8403 |

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims.

What is claimed is:

1. A compound having Formula I:

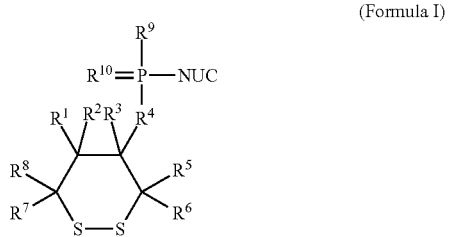

(Formula I)

wherein, $R^1$ is H, OH, $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups, $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NHC$_{1-6}$ alkyl, arylC$_{1-6}$ alkyl, heteroarylC$_{1-6}$ alkyl, heterocyclylC$_{1-6}$ alkyl, guanidinyl, $C_{1-6}$alkylC(O)O—, arylC(O)O—, heterocyclylC(O)O—, O-propargyl, S-propargyl, O-allyl, or S-allyl;

$R^4$ is S or O;

each $R^2$, $R^3$, $R^5$, $R^6$, $R^7$ and $R^8$ is independently halo or $R^1$ as above;

$R^9$ is O-phenyl, O-naphthyl, or O-benzyl any of which can be substituted with one or more halo groups; or NH-benzyl, NHR$^{12}$ or N(R$^{12}$)$_2$, wherein each R$^{12}$ is independently H, $C_{1-10}$ alkyl, or $C_{1-10}$ alkyl substituted with one or more halo groups;

$R^{10}$ is S or O; and

NUC is selected from the group consisting of:
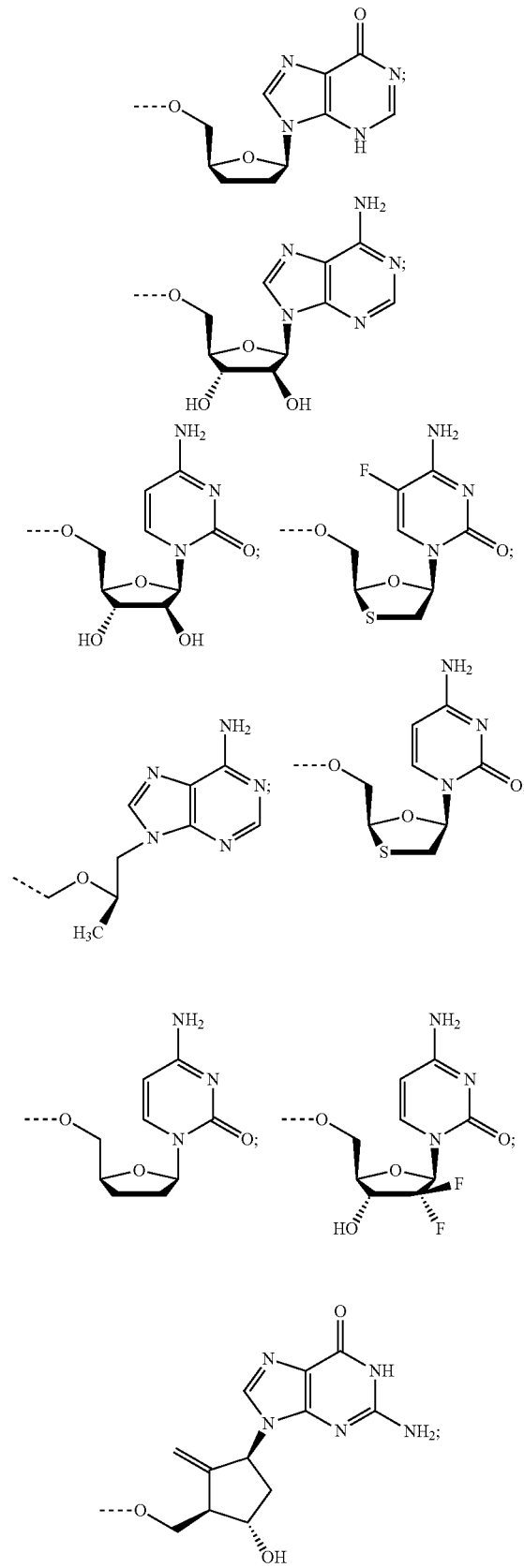
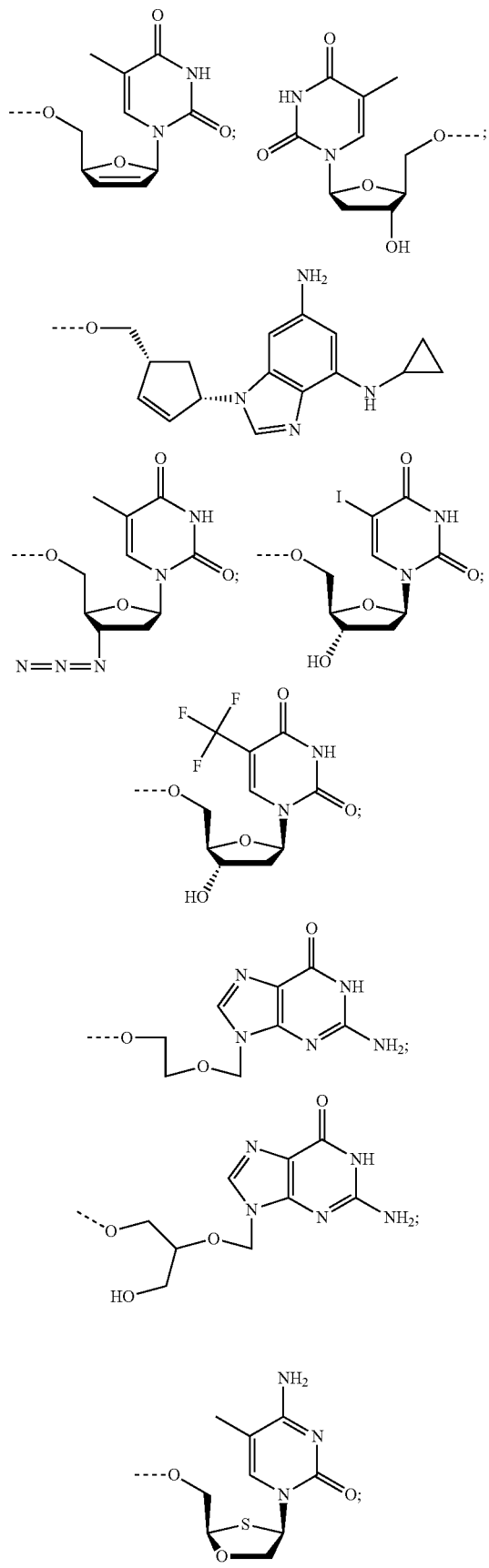

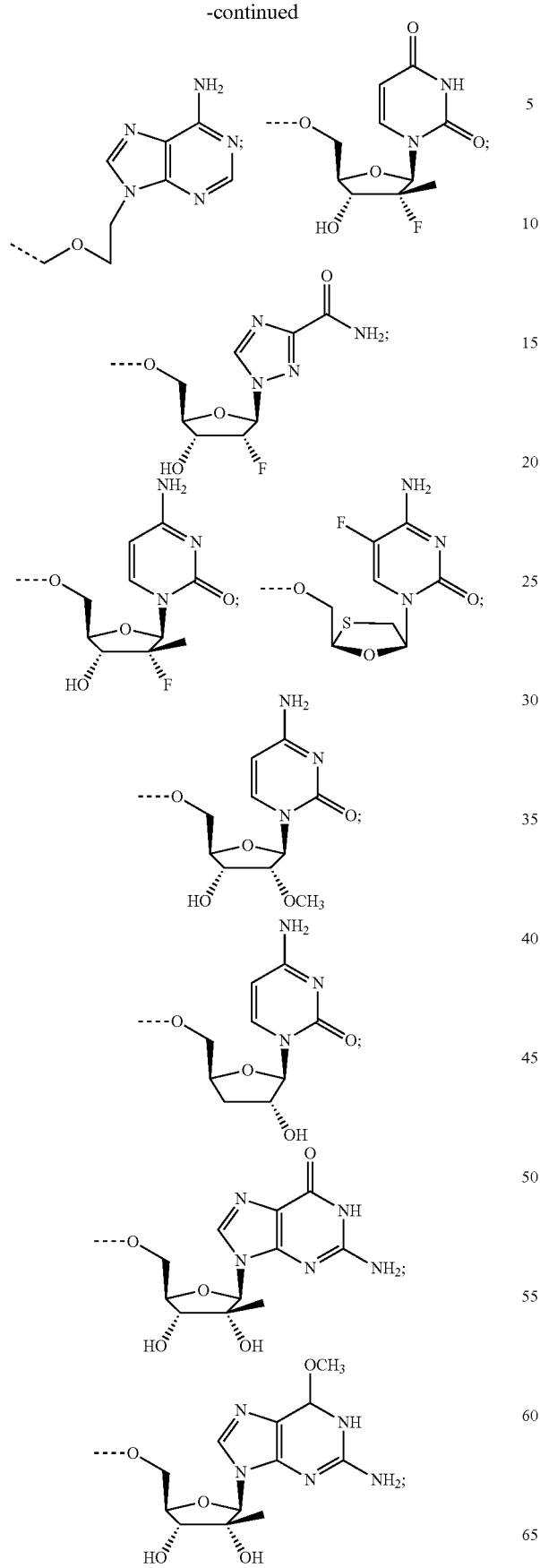
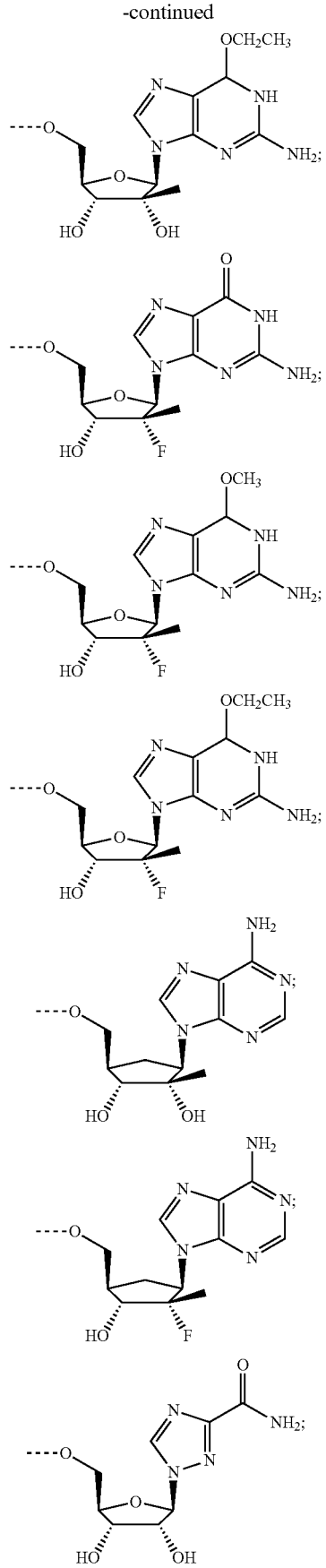

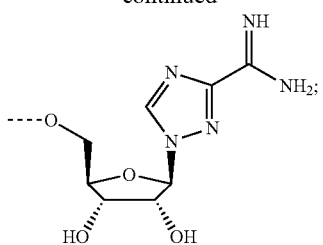
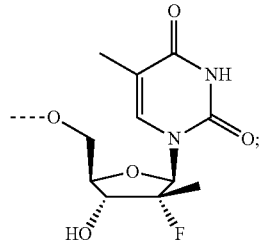
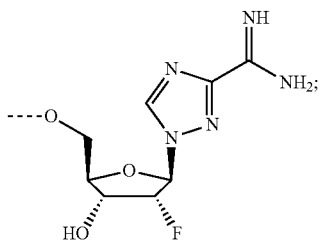
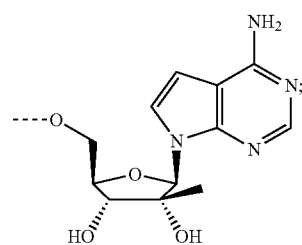
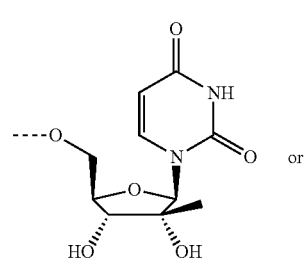
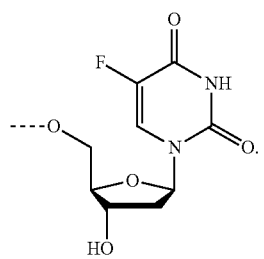
2. The compound of claim 1 having the following formula:
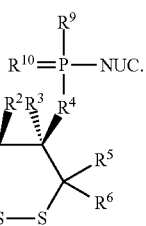
3. The compound of claim 1 having a structure selected from:
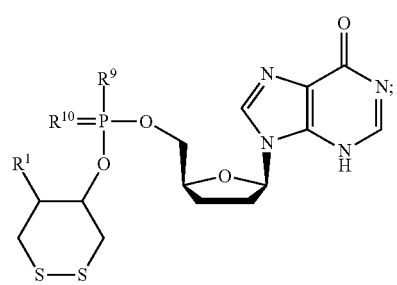
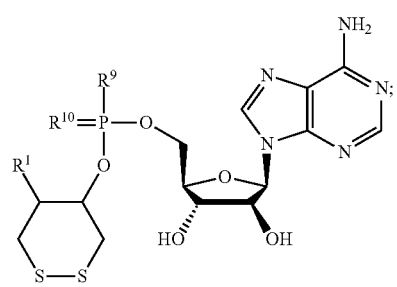
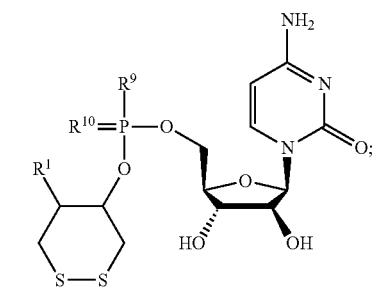
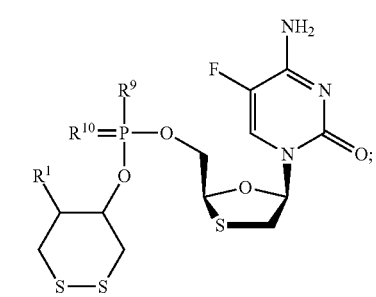

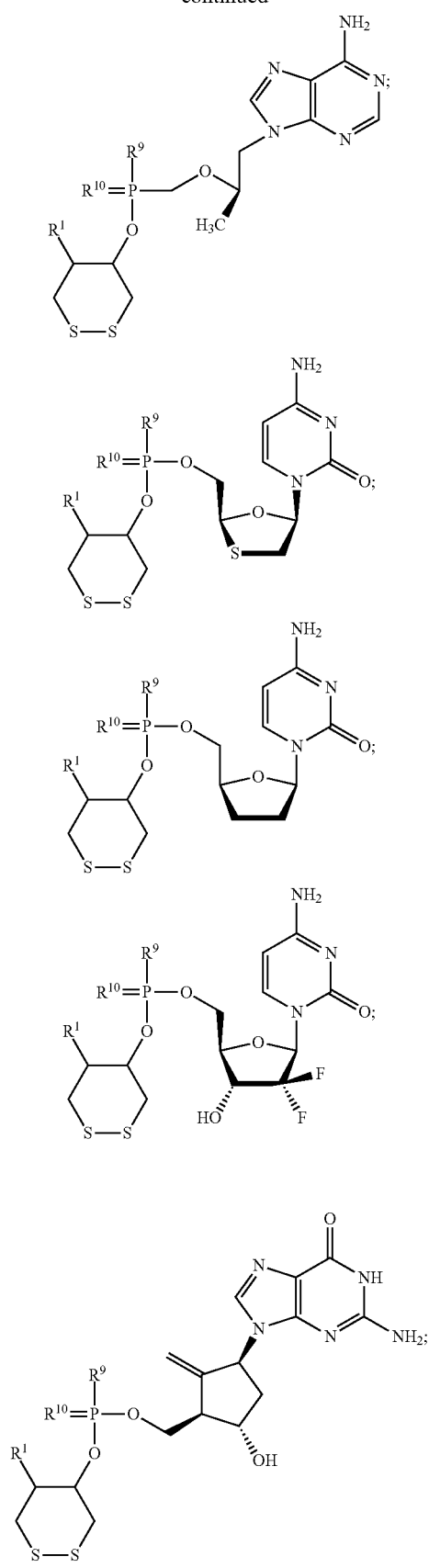
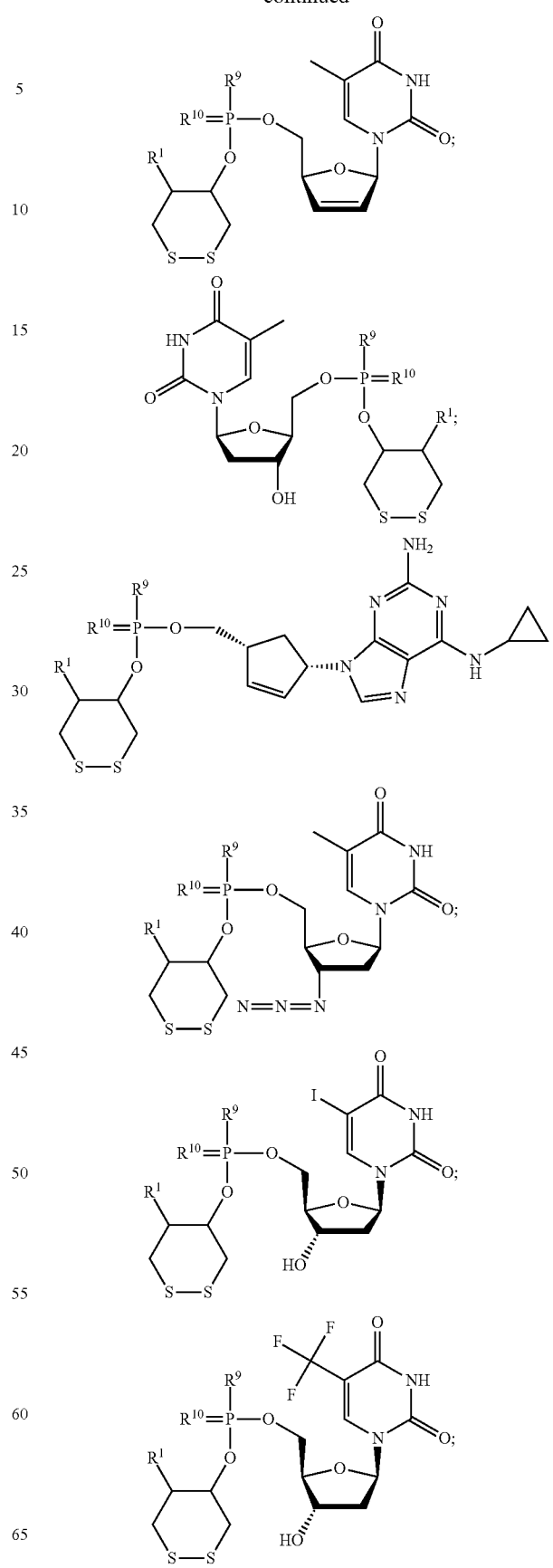

101
-continued
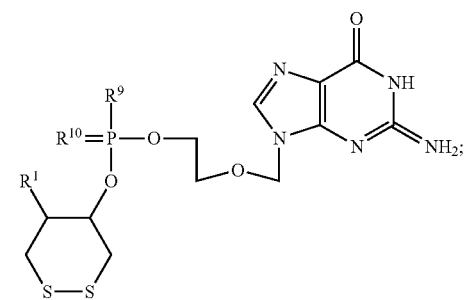
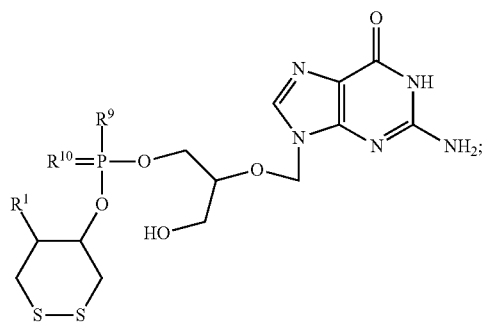
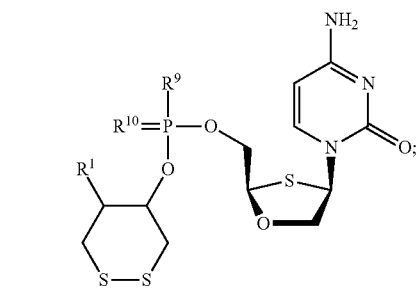
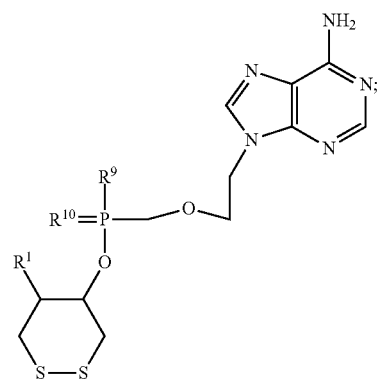
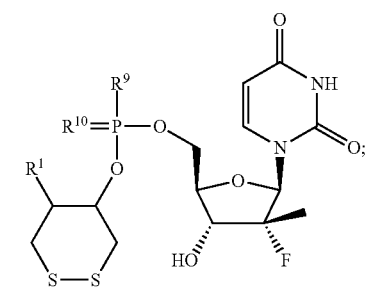
102
-continued
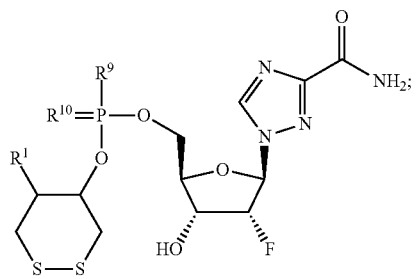
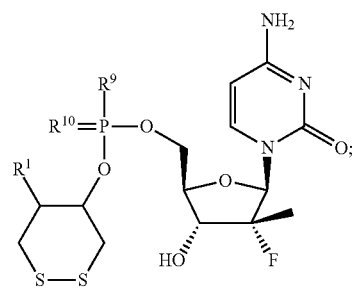
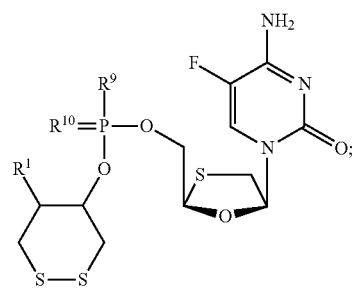
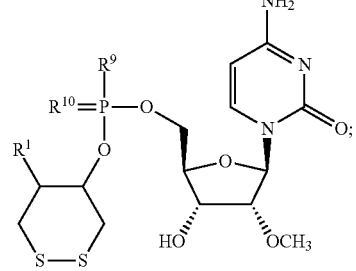
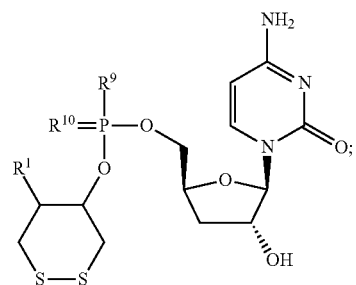
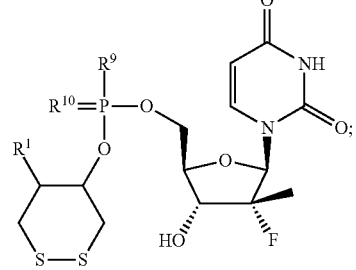

103
-continued
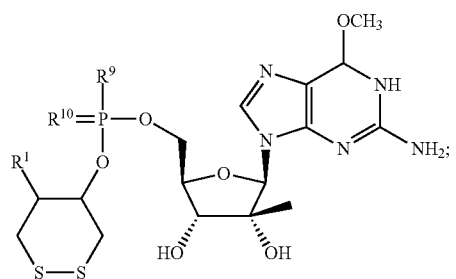
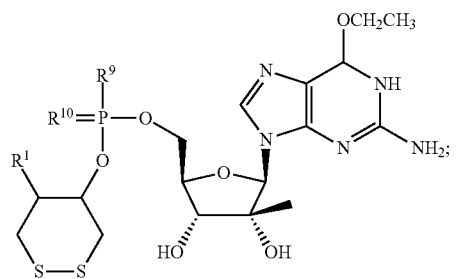
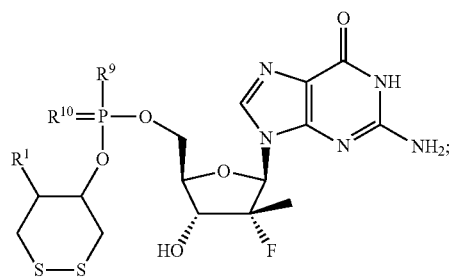
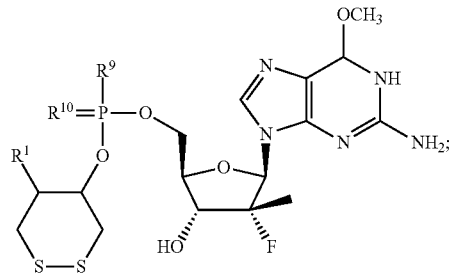
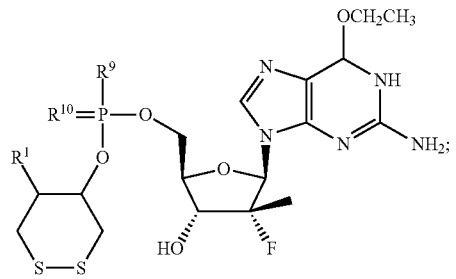
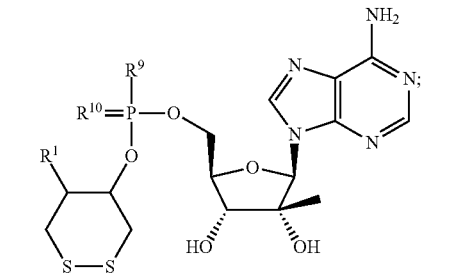
104
-continued
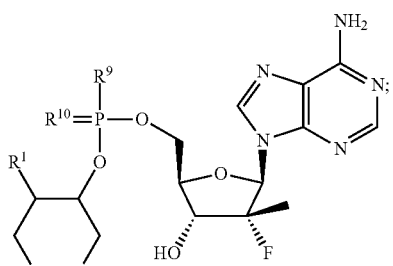
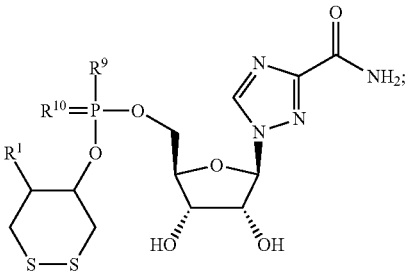
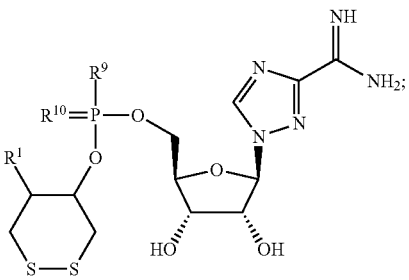
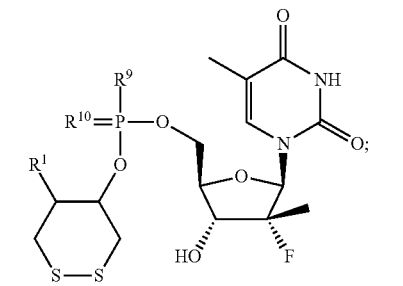
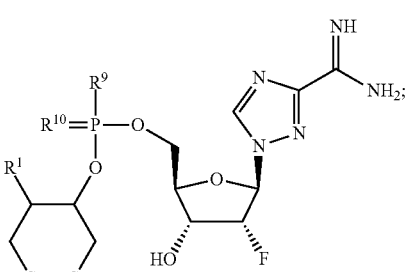
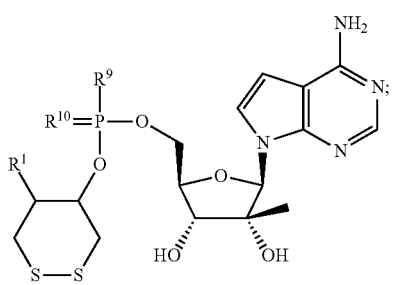

-continued

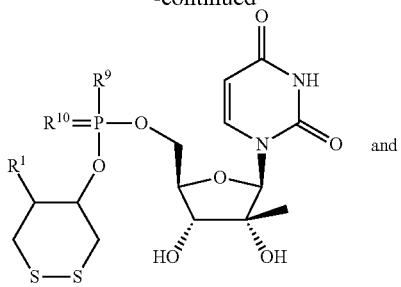

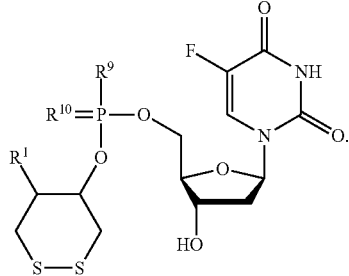

4. The compound of claim 3, wherein $R^{10}$ is O.

5. A compound having Formula II:

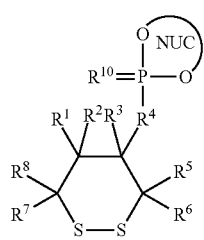
(Formula II)

wherein, $R^1$ is OH, $C_{1-6}$ alkyl, $C_{1-6}$ alkyl substituted with one or more hydroxyl groups, $C_{1-6}$ alkyl substituted with one or more halo groups, $C_{1-6}$ alkenyl, $C_{1-6}$ alkenyl substituted with one or more hydroxyl groups, $C_{1-6}$ alkenyl substituted with one or more halo groups, $C_{1-6}$ alkynyl, $C_{1-6}$ alkynyl substituted with one or more hydroxyl groups; $C_{1-6}$ alkynyl substituted with one or more halo groups, $C_{1-6}$ alkoxyl, $C_{1-6}$ alkoxyl substituted with one or more hydroxyl groups, $C_{1-6}$ alkoxyl substituted with one or more halo groups, aryl, heteroaryl, heterocyclyl, —NH$C_{1-6}$ alkyl, aryl$C_{1-6}$ alkyl; heteroaryl$C_{1-6}$ alkyl, heterocyclyl$C_{1-6}$ alkyl, guanidinyl, $C_{1-6}$alykylC(O)O—; arylC(O)O—, heterocyclylC(O)O—, O-propargyl, S-propargyl, O- or S-allyl;

$R^4$ is S or O;

each $R^2$, $R^3$, $R^5$, $R^6$, $R^7$ and $R^8$ is independently halo or $R^1$ as above;

$R^{10}$ is S or O; and

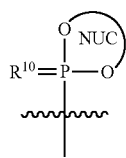

is selected from the group consisting of:

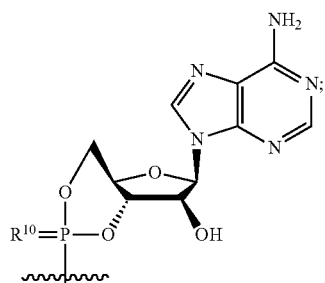

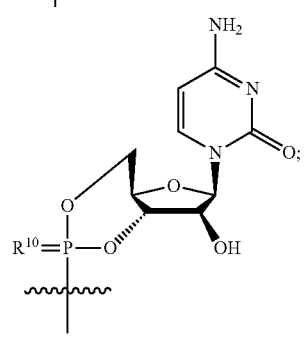

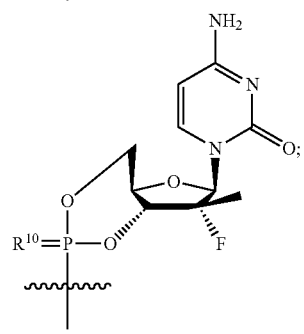

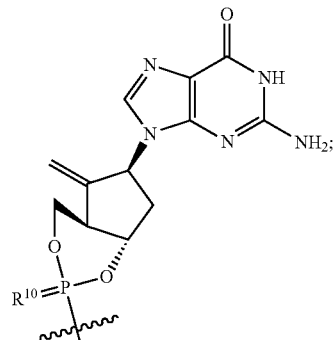

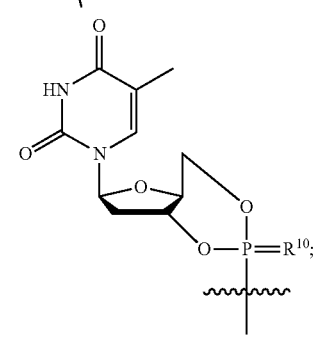

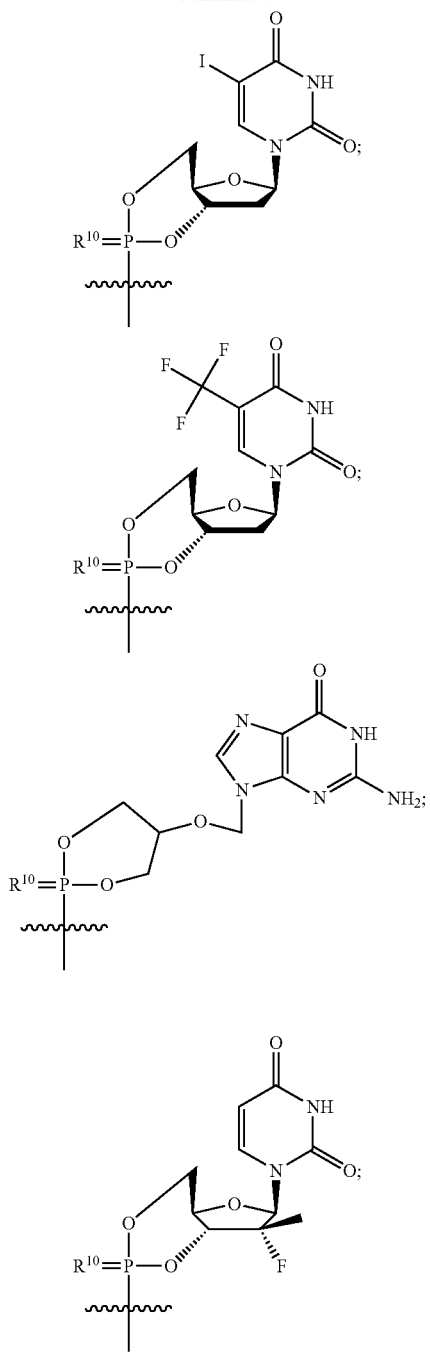
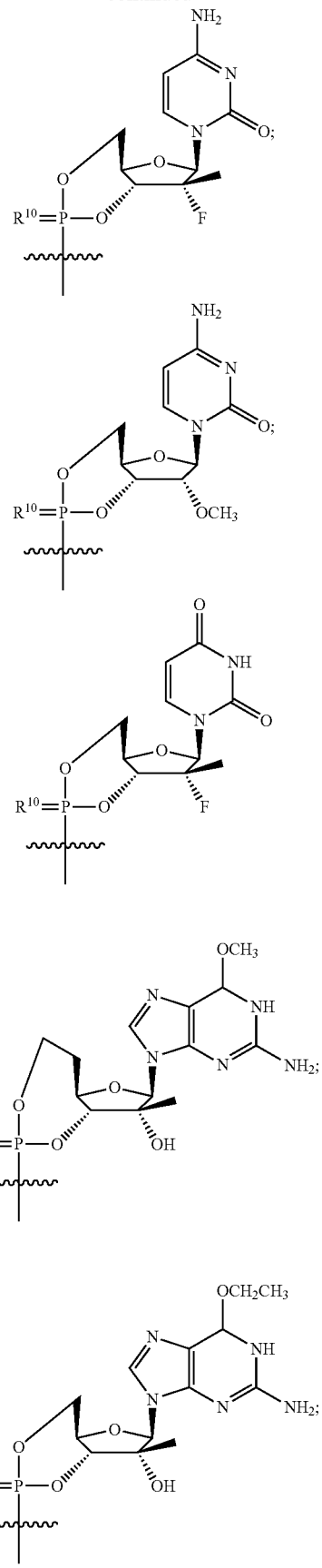

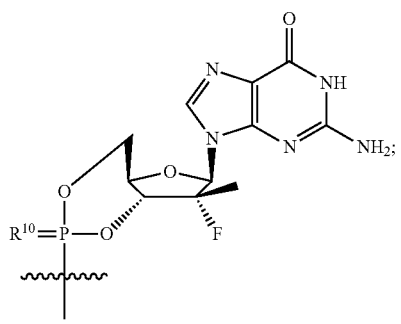
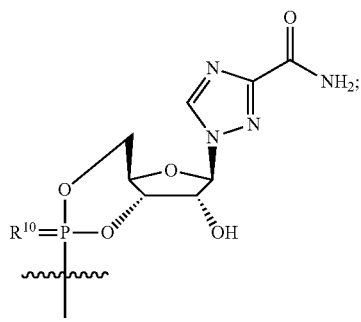
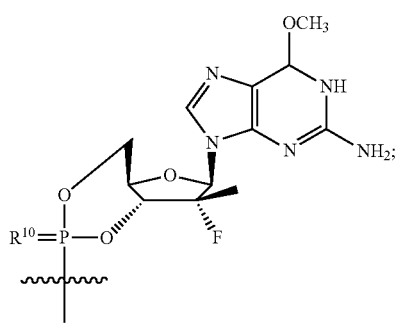
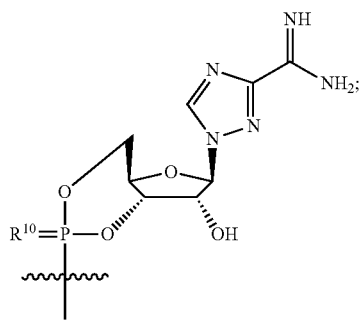
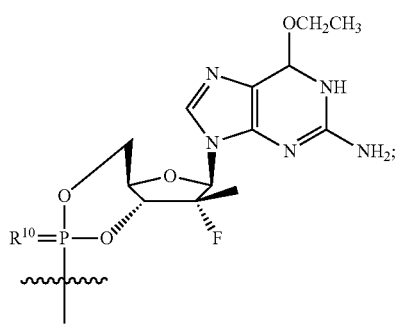
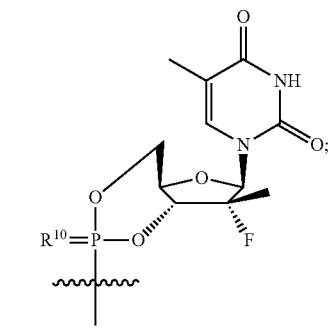
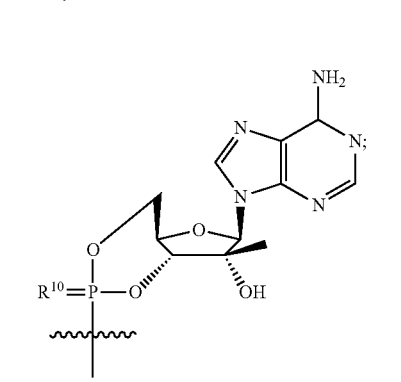
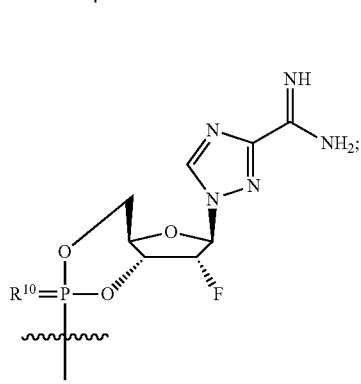
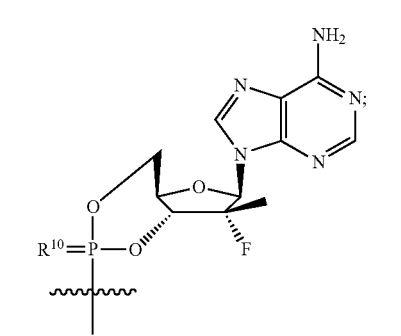
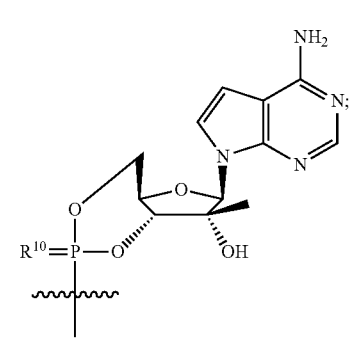

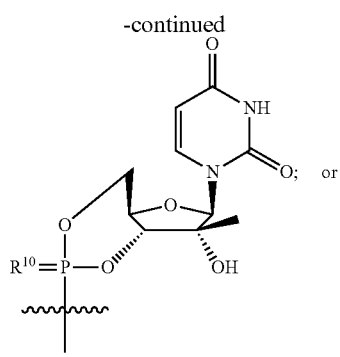
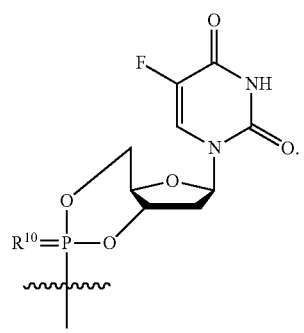
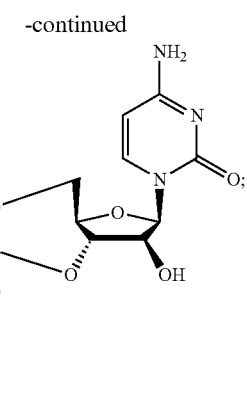
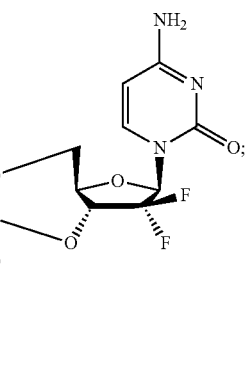
6. The compound of claim 5 having the following formula:
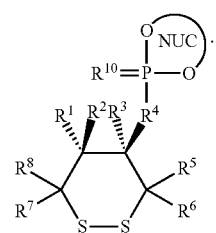
7. The compound of claim 5 having a structure selected from:
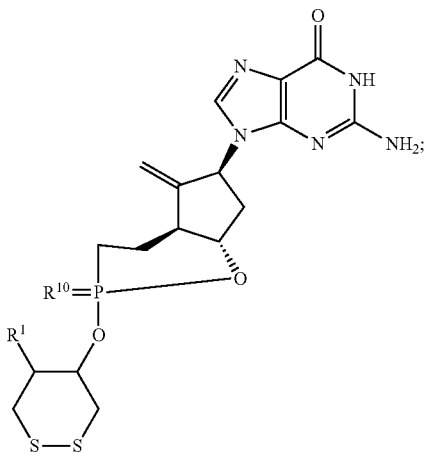
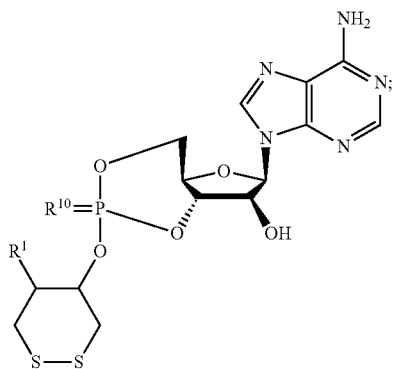
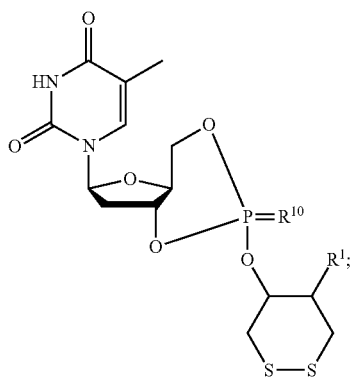

113
-continued
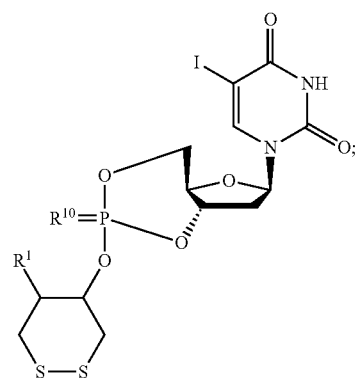
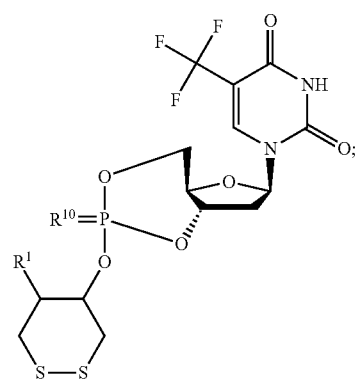
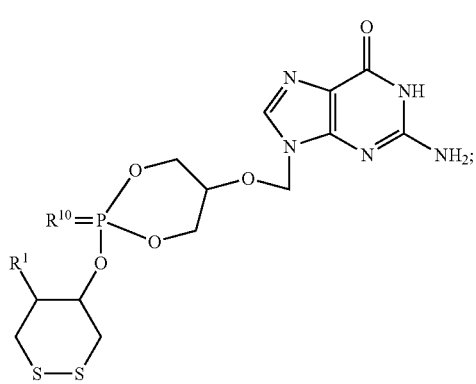
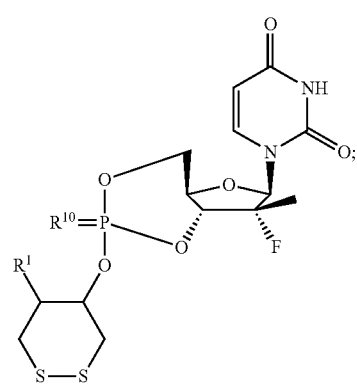
114
-continued
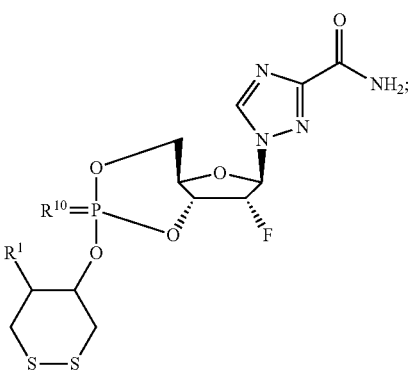
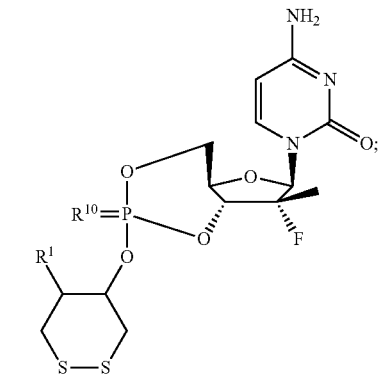
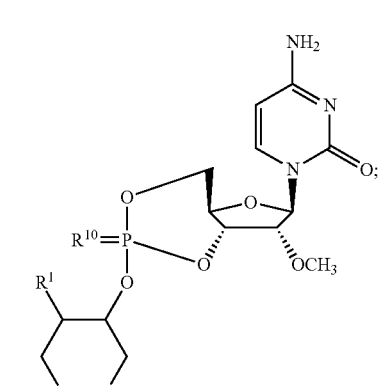
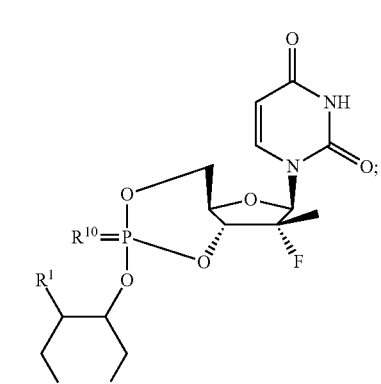

115
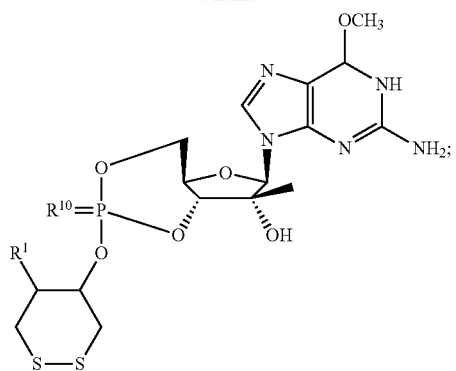
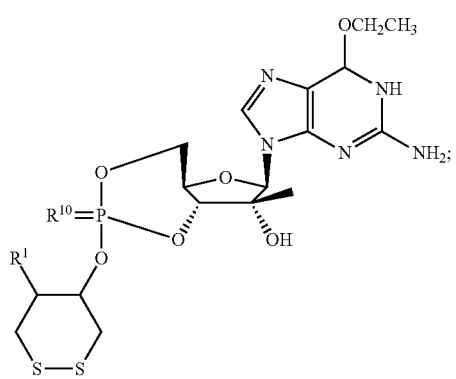
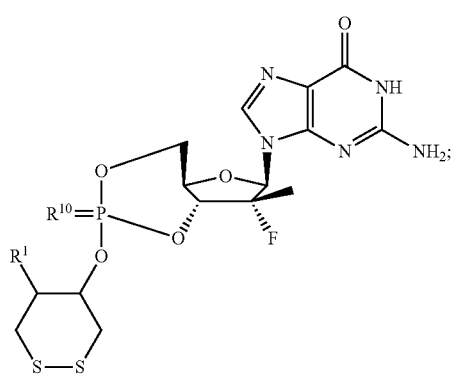
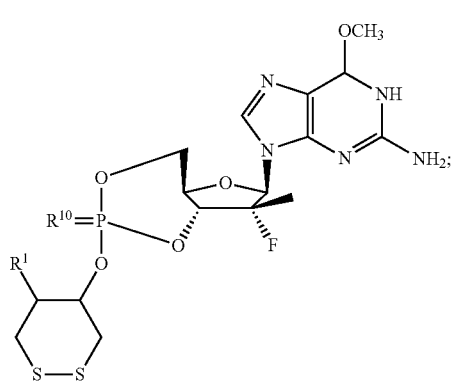
116
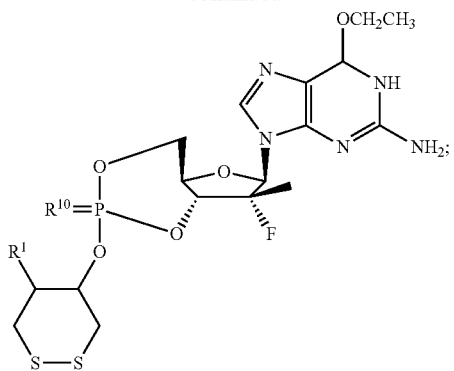
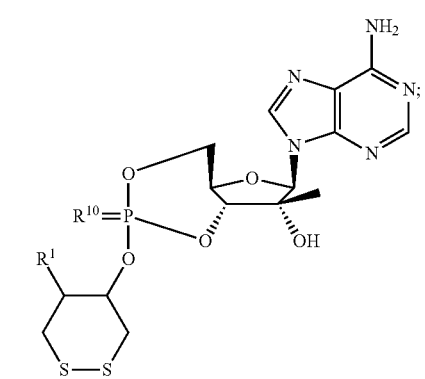
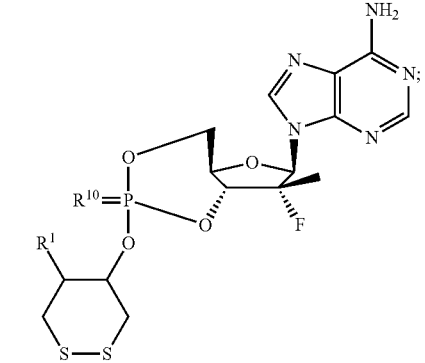
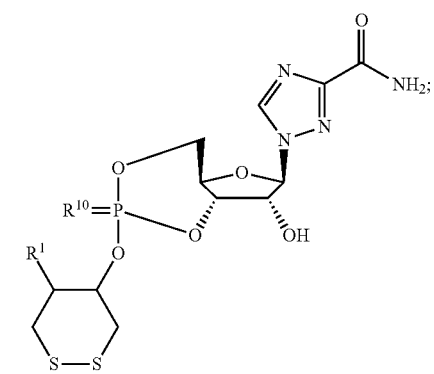

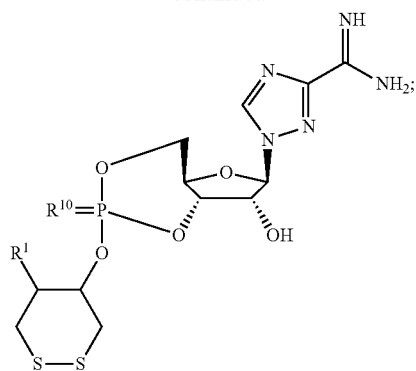

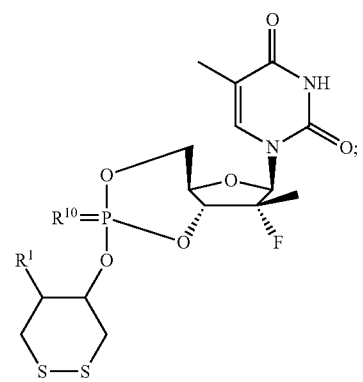

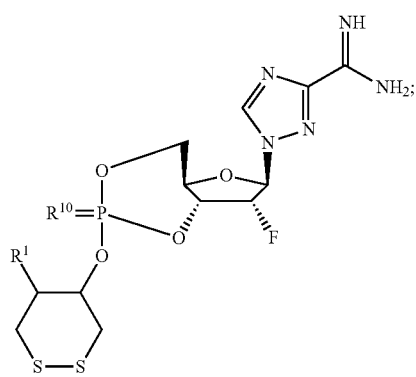

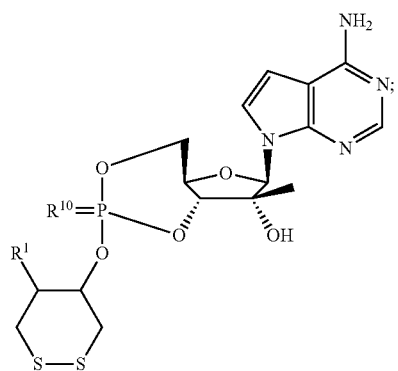

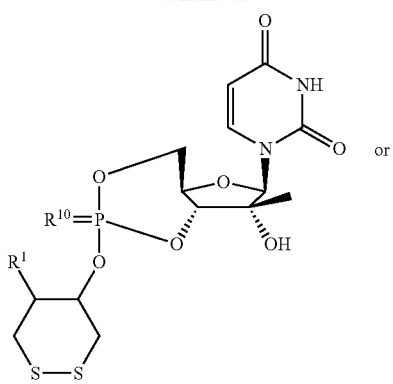

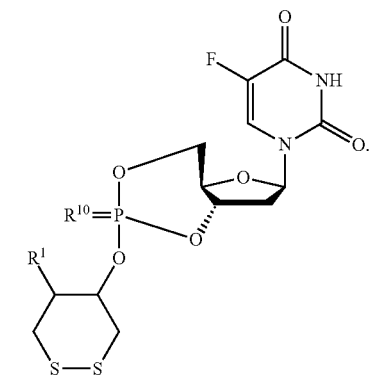

8. The compound of claim 7, wherein $R^{10}$ is O.

9. A composition comprising a compound of claim 1, or a pharmaceutically acceptable salt, solvate, or ester thereof, and a pharmaceutically acceptable carrier or diluent.

10. A method for the treatment of a viral infection in a patient in need thereof, comprising administering an effective amount of a compound of claim 1, or a pharmaceutically acceptable salt, solvate, or ester thereof, to the patient, wherein the viral infection is HCV, HBV or HIV infection.

11. The compound of claim 1, wherein $R^9$ is:

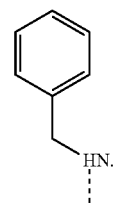

12. The compound of claim 1, wherein $R^9$ is:

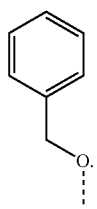

13. The compound of claim 1, wherein R⁹ is:
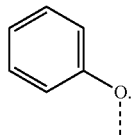
14. The compound of claim 1, wherein R9 is:
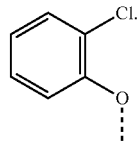
15. The compound of claim 1, wherein R9 is:
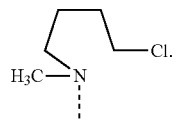
16. The compound of claim 1 having the following formula:
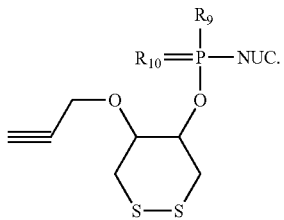
* * * * *